(12) United States Patent
Mohammad

(10) Patent No.: US 11,813,361 B2
(45) Date of Patent: Nov. 14, 2023

(54) DISINTEGRATING MONOLITHIC MODIFIED RELEASE TABLETS CONTAINING QUADRI-LAYER EXTENDED RELEASE GRANULES

(71) Applicant: Pharmaquest International Center, LLC, Flint, MI (US)

(72) Inventor: Mohammad Amin Mohammad, Amman (JO)

(73) Assignee: PHARMAQUEST INTERNATIONAL CENTER, LLP, Flint, MI (US)

(*) Notice: Subject to any disclaimer, the term of this patent is extended or adjusted under 35 U.S.C. 154(b) by 0 days.

(21) Appl. No.: 14/678,546

(22) Filed: Apr. 3, 2015

(65) Prior Publication Data

US 2015/0283084 A1 Oct. 8, 2015

Related U.S. Application Data

(60) Provisional application No. 61/975,540, filed on Apr. 4, 2014.

(51) Int. Cl.

| A61K 9/20 | (2006.01) |
| A61K 9/28 | (2006.01) |
| A61K 9/50 | (2006.01) |
| A61K 31/00 | (2006.01) |
| A61K 9/16 | (2006.01) |
| A61K 31/424 | (2006.01) |
| A61K 31/43 | (2006.01) |

(52) U.S. Cl.
CPC .......... *A61K 9/2081* (2013.01); *A61K 9/1682* (2013.01); *A61K 9/2013* (2013.01); *A61K 9/2027* (2013.01); *A61K 9/2054* (2013.01); *A61K 9/2866* (2013.01); *A61K 9/5084* (2013.01); *A61K 31/00* (2013.01); *A61K 31/424* (2013.01); *A61K 31/43* (2013.01)

(58) Field of Classification Search
None
See application file for complete search history.

(56) References Cited

U.S. PATENT DOCUMENTS

| 4,684,516 A * | 8/1987 | Bhutani ................ A61J 3/10 264/109 |
| 5,051,262 A | 9/1991 | Panoz et al. |
| 6,328,994 B1 | 12/2001 | Shimizu et al. |
| 6,399,086 B1 | 6/2002 | Katzhendler et al. |
| 6,692,769 B1 * | 2/2004 | Ishibashi ............. A61K 9/2081 424/464 |
| 2003/0171343 A1 * | 9/2003 | Furukawa ............ A61K 9/7076 514/169 |
| 2006/0121106 A1 | 6/2006 | Kerc et al. |
| 2008/0139526 A1 | 6/2008 | Treacy et al. |
| 2009/0088415 A1 | 4/2009 | Jain et al. |
| 2009/0111788 A1 | 4/2009 | Jain et al. |
| 2011/0020408 A1 | 1/2011 | Ramaraju et al. |
| 2013/0216624 A1 | 8/2013 | Lee |

FOREIGN PATENT DOCUMENTS

| CN | 101695478 B | 4/2010 |
| CN | 102552165 B | 7/2012 |
| EP | 0630235 B1 | 6/1997 |
| EP | 1596841 A1 | 11/2005 |
| EP | 1701705 A4 | 9/2006 |
| EP | 1715852 A2 | 11/2006 |
| EP | 1830819 | 9/2007 |
| EP | 1937223 A1 | 7/2008 |
| EP | 2001465 A1 | 12/2008 |
| EP | 2214680 A1 | 8/2010 |
| EP | 1838287 B1 | 5/2012 |
| JP | 2007/254342 * | 10/2007 |
| WO | WO 2004/073695 A1 | 9/2004 |
| WO | WO 2005/062898 A2 | 7/2005 |
| WO | WO 2005/065641 A2 | 7/2005 |
| WO | WO 2006/066930 A1 | 6/2006 |

(Continued)

OTHER PUBLICATIONS

Magnesium Stearate, Chemspider [online], (2015), retrieved (Sep. 29, 2016) from URL <http://www.chemspider.com/Chemical-Structure.10704.html>.*
Triacetin Safety Data Sheet of MilliporeSigma, Version 6.3, pp. 1-8, (revised Jun. 16, 2022), accessed Dec. 2, 2022. (Year: 2022).*
A.M. Cooperman and S.A. Cook, "Gastric emptying—physiology and measurements." *Surgical Clinics of North America*, vol. 56, Issue 6, Dec. 1976, pp. 1277-1287.
Amnon Hoffman, Haim D. Danenberg, Ifat Katzhendler, Rivka Shuval, Dalia Gilhar, Michael Friedman, "Pharmacodynamic and pharmacokinetic rationales for the development of an oral controlled-release amoxicillin dosage form." *Journal of Controlled Release*, vol. 54, Issue 1, Jun. 1998, pp. 29-37.

(Continued)

*Primary Examiner* — David J Blanchard
*Assistant Examiner* — Sarah J Chickos
(74) *Attorney, Agent, or Firm* — Crowell & Moring LLP

(57) ABSTRACT

The present invention relates to a modified release pharmaceutical formulation comprising one or more sustained release granules that may be prepared by over-mixing and hot melt granulation. The invention also relates to disintegrating monolithic modified release tablets comprising the sustained release granules as an internal phase and an immediate release formulation of a drug or drugs as an external phase. The drug release profile from either these granules or these tables may be adjusted by adjusting the percentages of the formulation's components. In one application, the disintegrating monolithic modified release tablets comprise amoxicillin and clavulanate and have a dissolution profile similar to brand and generic "Augmentin XR® Bilayered Extended Release Tablets (1000 mg/62.5 mg)". The invention also relates to a method of preparing the foregoing sustained release granules.

20 Claims, 1 Drawing Sheet

(56) References Cited

FOREIGN PATENT DOCUMENTS

| WO | WO 2006/072577 A1 | 7/2006 |
|----|---|---|
| WO | WO 2007/021101 A1 | 2/2007 |
| WO | WO 2007/068948 A2 | 6/2007 |
| WO | WO 2007/110875 A1 | 10/2007 |
| WO | WO 2008/021394 A2 | 2/2008 |
| WO | WO 2008/029351 A2 | 3/2008 |
| WO | WO 2008/109462 A2 | 9/2008 |
| WO | WO 2009/055038 A1 | 4/2009 |

OTHER PUBLICATIONS

Arancibia A., González G., Icarte A., Arancibia M., Arancibia P., "Pharmacokinetics and bioavailability of a controlled release amoxicillin formulation." *Int. J. Clin. Pharmacol Ther Toxicol.*, vol. 25, Issue 2, Feb. 1987, pp. 97-100.

Bertil Abrahamsson, Magne Alpsten, Ulf E. Jonsson, P.J. Lundberg, Anders Sandberg, Mats Sundgren, Agneta Svenheden, Jukka Tölli, "Gastro-intestinal transit of a multiple-unit formulation (metoprolol CR/ZOK) and a non-disintegrating tablet with the emphasis on colon." *International Journal of Pharmaceutics*, vol. 140, Issue 2, Aug. 30, 1996, pp. 229-235.

Carl-Alexander Scheef, Dieter Oelkrug, Peter C. Schmidt, "Surface acidity of solid pharmaceutical excipients III. Excipients for solid dosage forms.", *European Journal of Pharmaceutics and Biopharmaceutics*, vol. 46, Issue 2, Sep. 1998, pp. 209-213.

Chuan-Yu Wu, Serena M. Best, A. Craig Bentham, Bruno C. Hancock, William Bonfield. "A simple predictive model for the tensile strength of binary tablets." *European Journal of Pharmaceutical Sciences*, vol. 25, Issues 2-3, Jun. 2005, pp. 331-336.

Erika Fekete, János Móczó, Béla Pukánszky, "Determination of the surface characteristics of particulate fillers by inverse gas chromatography at infinite dilution: a critical approach." *Journal of Colloid and Interface Science*, vol. 269, Issue 1, Jan. 1, 2004, pp. 143-152.

Fridrun Podczeck: "The determination of fracture mechanics properties of pharmaceutical materials in mode III loading using an anti-clastic plate bending method." *International Journal of Pharmaceutics*, vol. 227, Issues 1-2, 4, Oct. 2001, pp. 39-46.

International Search Report and Written Opinion of the International Searching Authority, International Application No. PCT/US2015/024267 (dated Jan. 21, 2016).

J. N. Hunt and M. T. Knox. "A relation between the chain length of fatty acids and the slowing of gastric emptying." *The Journal of Physiology*, vol. 194, Issue 2, Feb. 1968, pp. 327-336.

Locatelli, N. Nagelj Kovacic, A. Mrhar, M. Bogataj. "Gastric emptying of nondisintegrating solid drug delivery systems in fasted state: relevance to drug dissolution." *Expert Opin. Drug Delivery*, vol. 7, Issue 8, Aug. 2010, pp. 967-976.

M. Štefanič, I. Locatelli, F. Vrečer, T. Sever, A. Mrhar, M. Bogataj. "The influence of gastric emptying kinetics on the drug release from enteric coated pellets in fasted state: An in vitro/in vivo correlation." *European Journal of Pharmaceutics and Biopharmaceutics*, vol. 82, Issue 2, Oct. 2012, pp. 376-382.

Niranjan Kottala, Admassu Abebe, Omar Sprockel, Ilgaz Akseli, Faranak Nikfar, Alberto M. Cuitiño. "Characterization of Interfacial Strength of Layered Powder-Compacted Solids." *Powder Technology*, In Press, Accepted Manuscript, Available Online Feb. 8, 2013.

S. M. Berge, et al., *J. Pharmaceutical Sciences*, 1977, 66, pp. 1-19.

Thomas M. File, Javier Garau, Michael R. Jacobs, Brian Wynne, Monique Twynholm, Elchonon Berkowitz, "Efficacy of a new pharmacokinetically enhanced formulation of amoxicillin/clavulanate (2000/125 mg) in adults with community-acquired pneumonia caused by *Streptococcus pneumoniae*, including penicillin-resistant strains," *International Journal of Antimicrobial Agents*, vol. 25, Issue 2, Feb. 2005, pp. 110-119.

William A. Craig, "Overview of Newer Antimicrobial Formulations for Overcoming Pneumococcal Resistance." *The American Journal of Medicine Supplements*, vol. 117, Issue 3, Aug. 2004, pp. 16-22.

I. Ghebre-Sellassie, Pellets: A general overview, in: I. Ghebre-Sellassie (Ed.), Pharmaceutical Pelletization Technology, Marcel Dekker Inc., New York and Basel, 1989, pp. 1-13.

A. Dukic'-Ott, M. Thommes, J.P. Remon, P. Kleinebudde, C. Vervaet. Production of pellets via extrusion—spheronisation without the incorporation of microcrystalline cellulose: A critical review. European Journal of Pharmaceutics and Biopharmaceutics 71 (2009) 38-46.

Clinical Pharmacology and Biopharmaceutics Review, NDA No. 50-785, Dec. 20, 2000.

International Search Report and Written Opinion of the International Searching Authority, App. No. PCT/US2015/024267, dated Jan. 21, 2016, pp. 1-13, European Patent Office, The Netherlands.

Canada Examination Report for Application No. 2,944,900 (PCT No. U.S. Pat. No. 2015024267), dated May 7, 2021, 3 pp.

* cited by examiner

DISINTEGRATING MONOLITHIC MODIFIED RELEASE TABLETS CONTAINING QUADRI-LAYER EXTENDED RELEASE GRANULES

CROSS-REFERENCE TO RELATED APPLICATIONS

This application claims the benefit of U.S. Provisional Application No. 61/975,540, filed Apr. 4, 2014, the entire contents of which are incorporated herein by reference.

BACKGROUND

1. Technical Field Text

This invention relates to a modified release pharmaceutical formulation comprising one or more sustained release granules and a method of preparing said sustained release granules for use in a modified release pharmaceutical formulation.

2. Background Information

Pharmaceutical formulations designed to release one drug immediately and another drug sustainably, are of considerable interest today.

For example, TARKA® tablets contain trandolapril in an immediate release form and verapamil hydrochloride in an extended release form. Augmentin XR® Extended Release Tablets are designed to provide both immediate and sustained release of amoxicillin and immediate release of clavulanic acid.

Despite the popularity of the foregoing products, improvements may be made to formulations for immediate and sustained release. It is an object of this invention to provide an improved formulation for immediate and sustained release of various drugs. A further object of this invention is to provide an improved method for preparing such formulations.

SUMMARY OF INVENTION

The present invention is directed to a modified release pharmaceutical formulation comprising one or more sustained release granules and a method of preparing said sustained release granules for use in a modified release pharmaceutical formulation.

DETAILED DESCRIPTION

The modified release pharmaceutical formulation of the present invention may comprise one or more sustained release granules. Each sustained release granule comprises (1) an agglomerated drug particle comprising: (a) one or more overlubricated drug particles comprising (i) a core particle comprising a drug; and (ii) a hydrophobic adherent layer comprising a hydrophobic adherent material posited over at least a portion of the core particle; and (b) a hydrophobic binding layer comprising a hydrophobic binding material, wherein the one or more overlubricated drug particles are suspended in the hydrophobic binding material; and (2) a disintegrant layer comprising a disintegrant material posited over at least a portion of the hydrophobic binding layer of the agglomerated drug particle.

Figure 1:
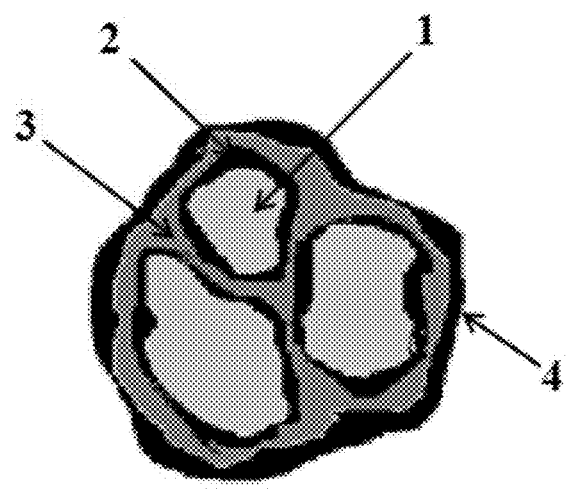
FIG. 1 depicts a sustained release granule in accordance with one embodiment of the present invention.

FIG. 1 depicts a sustained release granule in accordance with one embodiment of the present invention. The sustained release granule shown in FIG. 1 has four layers structure, including a core drug particle 1, a hydrophobic adherent layer 2, a hydrophobic binding layer 3, and a disintegrant layer 4.

Figure 2:
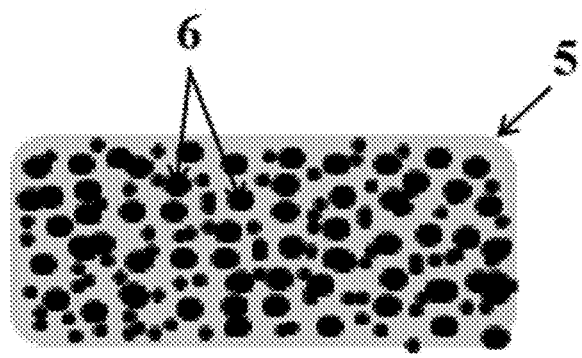
FIG. 2 depicts a disintegrating monolithic sustained release tablet in accordance with one embodiment of the present invention.

FIG. 2 depicts a disintegrating monolithic sustained release tablet in accordance with another embodiment of the present invention. The disintegrating monolithic sustained release tablet shown in FIG. 2 has two phases, including an external phase 5 comprising an immediate release drug formulation and an internal phase comprising sustained release granules 6, which may have the structure shown in FIG. 1.

In some embodiments, the core particle has a substantially isodiametric shape.

In some embodiments, the core particle has a diameter of between about 200 μm and about 600 μm.

In some embodiments, the hydrophobic adherent layer comprises a plurality of hydrophobic adherent particles, the hydrophobic adherent particles comprising the hydrophobic adherent material. In some embodiments, the hydrophobic adherent particles have a projected area diameter of no more than about 5 μm.

In some embodiments, the hydrophobic adherent material has a melting point of at least about 100° C.

In some embodiments, the hydrophobic adherent material is magnesium stearate.

In some embodiments, the hydrophobic binding material has a melting point of no more than about 70° C.

In some embodiments, the hydrophobic binding material is stearic acid.

In some embodiments, the disintegrant material is an amino acid, starch, corn starch, carmellose, carmellose sodium, carmellose calcium, croscarmellose sodium, crospovidone, low-substituted hydroxypropylcellulose, hydroxypropyl starch, or sodium carboxymethyl starch, preferably crospovidone or carmellose, and more preferably crospovidone.

In some embodiments, the disintegrant material is crospovidone.

In some embodiments, the particle size of the crospovidone disintegrant is selected to influence the deaggregation of the sustained release granules. Larger particles provide a faster deaggregation than smaller particles. Many commercial grades of crospovidone are available and are suitable for use as the disintegrant material, including Kollidon CL, Kollidon CL-M, Polyplasdone XL, and Polyplasdone XL-10, preferably, Polyplasdone XL-10.

In some embodiments, the disintegrant layer comprises a wetting agent, such as sodium lauryl sulfate.

In some embodiments, the drug is a hydrophilic drug.

In some embodiments, the drug is a hydrophobic drug.

In some embodiments, the drug is amoxicillin or a pharmaceutically acceptable salt thereof. In some embodiments, the drug is amoxicillin trihydrate. In some embodiments, the amoxicillin trihydrate is Purimox® Compacted Grade P, which has a mean particle size of about 350 μm.

In some embodiments, the modified release pharmaceutical formulation further comprises an external phase, wherein the one or more sustained release granules are suspended in the external phase.

In some embodiments, the formulation is a tablet, such as a tablet for oral administration. In some embodiments, the tablet is a disintegrating monolithic sustained release tablet.

In some embodiments, the formulation contains a first drug in the sustained release granule and a second drug in the external phase. In some embodiments, the first drug and the second drug are the same. In some embodiments, the first drug and the second drug are different. In some embodiments, the first drug is present in both the core and the external phase and a second drug present in the external phase.

In some embodiments, the external phase is an immediate release formulation.

In some embodiments the external phase comprises a pharmaceutically acceptable excipient, such as microcrystalline cellulose.

In some embodiments, the drug is amoxicillin or a pharmaceutically acceptable salt thereof, wherein between about 80% and about 90% of the total amoxicillin content is disposed in the sustained release granules, and wherein between about 10% and about 20% of the total amoxicillin content is disposed in the external phase. In some embodiments, the dissolution percentage of amoxicillin during the first hour of a dissolution test is between about 40% and about 60%.

In some embodiments, the second drug is clavulanic acid or a pharmaceutically acceptable salt thereof. In some embodiments, the second drug is potassium clavulanate. In some embodiments, the dissolution percentage of clavulanic acid during the first hour of a dissolution test is at least about 85%. In some embodiments, the potassium clavulanate is present in 1:1 ratio with microcrystalline cellulose.

In some embodiments, the drug (or first drug) makes up between about 50 and about 95 wt. %, preferably between 65 and about 90 wt. %, and more preferably about 70 wt. % of the formulation.

The method of the present invention may comprise the steps of (1) providing a plurality of agglomerated drug particles; and (2) treating the agglomerated drug particles with a disintegrant material to afford sustained release granules.

In some embodiments of the method, the disintegrant material is crospovidone.

In some embodiments of the method, the ratio of the agglomerated drug particles to the disintegrant material is between about 10:1 and about 17:1.

In some embodiments of the method, the step of providing a plurality of agglomerated drug particles comprises (1) providing overlubricated drug particles; and (2) treating the overlubricated drug particles with a hydrophobic binding material to afford the agglomerated drug particles.

In some embodiments of the method, the hydrophobic binding material is stearic acid.

In some embodiments of the method, the ratio of the overlubricated drug particles to the hydrophobic binding material is between about 3.6:1 and about 6:1.

In some embodiments of the method, the step of treating the overlubricated drug particles with a hydrophobic binding material comprises (1) mixing the overlubricated drug particles with the hydrophobic binding material; (2) granulating the resulting mixture at a temperature of between about 60° C. and about 70° C.; and (3) sieving the resulting granules to afford the agglomerated drug particles, wherein between about 10% and about 80% of the agglomerated drug particles have a diameter of between about 90 μm and about 500 μm, and wherein between about 20% and about 90% of the agglomerated drug particles have a diameter of between about 500 μm and about 1000 μm.

In some embodiments of the method, the step of providing overlubricated drug particles comprises treating a plurality of core particles with a hydrophobic adherent material, the core particles comprising the drug.

In some embodiments of the method, the hydrophobic adherent material is magnesium stearate.

In some embodiments of the method, the drug is amoxicillin or a pharmaceutically acceptable salt thereof.

In some embodiments of the method, the drug is amoxicillin trihydrate.

In some embodiments of the method, the ratio of the drug to the hydrophobic adherent material is between about 12:1 and about 20:1.

In some embodiments of the method, liquids, such as water and/or organic solvents, are not used in any step of manufacturing the sustained release granules.

Alternate embodiments of the formulation and method of the present invention are given below. Each alternative embodiment set forth below is applicable to both the formulation and the method, where appropriate:

(1) formulations and methods wherein the drug (or the first drug) is:
  a. A hydrophilic drug;
  b. A hydrophobic drug;
  c. Amoxicillin or a pharmaceutically acceptable salt thereof;
  d. Amoxicillin trihydrate;
  e. Acetaminophen;
  f. Buproprion hydrochloride;
  g. Cefaclor;
  h. Diazepam;
  i. Disopyramide phosphate;
  j. Isosorbide mononitrate;
  k. Metformin hydrochloride;
  l. Methylphenidate hydrochloride;
  m. Nifedipine;
  n. Orphenadrine citrate;
  o. Oxprenolol hydrochloride;
  p. Oxtriphylline;
  q. Pentoxifylline;
  r. Propanolol hydrochloride;
  s. Pseudoephedrine hydrochloride;
  t. Quinidine;
  u. Zolpidem tartrate; or v. A drug having a melting point of at least 90° C.;

(2) formulations and methods wherein the second drug is:
  a. Clavulanic acid or a pharmaceutically acceptable salt thereof;
  b. Potassium clavulanate;
  c. Fexofenadine hydrochloride; or
  d. Hydrochlorothiazide;

(3) formulations and methods wherein the core particles have a diameter of:
  a. Between about 200 μm and about 600 μm;
  b. Between about 250 μm and about 355 μm;

(4) formulations and methods wherein the core particles have a substantially isodiametric shape;

(5) formulations and methods wherein the hydrophobic adherent material:
  a. Has a melting point of at least about 100° C.;
  b. Is magnesium stearate;
  c. Is aluminum stearate;
  d. Is calcium stearate;
  e. Is zinc stearate;
  f. Is sodium stearate;

g. Is magnesium palmitate;
h. Is a stearic acid salt;
i. Is a palmitic acid salt; or
j. Consists essentially of a pharmaceutically acceptable hydrophobic material, preferably, having a flake like shape;
(6) formulations and methods wherein the hydrophobic binding material:
a. Has a melting point of no more than about 70° C.;
b. Is stearic acid;
c. Is palmitic acid;
d. Is stearyl alcohol;
e. Is palmityl alcohol;
f. Is glyceryl monostearate;
g. Is glyceryl mono and distearate;
h. Is glyceryl tristearate;
i. Is glyceryl tripalmitate;
j. Is glyceryl trimyristate;
k. Is glyceryl tribehenate; or
l. Is glyceryl palmito-stearic ester;
(7) formulations and methods wherein the disintegrant material is:
a. Crospovidone;
b. Carmellose;
c. An amino acid;
d. Starch;
e. Corn starch;
f. Carmellose sodium;
g. Carmellose calcium;
h. Croscarmellose sodium;
i. Low-substituted hydroxypropylcellulose;
j. Hydroxypropyl starch; or
k. Sodium carboxymethyl starch.
(8) formulations and methods wherein the pharmaceutical excipient is:
a. Microcrystalline cellulose;
b. A starch;
c. Lactose;
d. Sucrose;
e. Glucose;
f. Mannitol;
g. Silicic acid;
h. Carboxymethyl cellulose;
i. Alginates;
j. Gelatin;
k. Polyvinylpyrrolidone;
l. Sorbitol;
m. Dextrin;
n. Calcium phosphate;
o. Calcium carbonate;
p. Sodium alginate;
q. Collagen;
r. Agar;
s. Alginic acid;
t. A silicate;
u. Sodium carbonate;
v. Paraffin;
w. A quarternary ammonium compound;
x. Cetyl alcohol;
y. Glycerol monostearate
z. Kaolin;
aa. Bentonite clay;
bb. Talc;
cc. Calcium stearate;
dd. Magnesium stearate;
ee. Solid polyethylene glycol;
ff. Sodium lauryl sulfate; and
gg. Mixtures thereof.

(9) formulations wherein:
a. Between about 80% and about 90% of the drug (or first drug) content is disposed in the sustained release granules, and wherein between about 10% and about 20% of the drug (or first drug) content is disposed in the external phase.
(10) formulations wherein the dissolution percentage of the drug (or first drug) is:
a. Between about 40% and about 60% during the first hour of a dissolution test;
(11) formulations wherein the dissolution percentage of the second drug is:
a. At least about 85% during the first hour of a dissolution test;
(12) formulations and methods wherein the ratio of the agglomerated drug particles to the disintegrant material is:
a. Between about 10:1 and about 17:1;
(13) formulations and methods wherein the ratio of the overlubricated drug particles to the hydrophobic binding material is:
a. Between about 3.6:1 and about 6:1; and
(14) formulations and methods wherein the ratio of the drug to the hydrophobic adherent material is:
a. Between about 12:1 and about 20:1.

It is understood that further embodiments of the formulation and method of the present invention comprise combinations of embodiments (1) through (14) above. For example, alternative embodiments comprise the combination of (1)(a), (5)(a), and (6)(a); (1)(a), (5)(a), and (6)(b); (1)(a), (5)(a), and (6)(c); (1)(a), (5)(a), and (6)(d); (1)(a), (5)(a), and (6)(e); (1)(a), (5)(a), and (6)(f); (1)(a), (5)(a), and (6)(g); (1)(a), (5)(a), and (6)(h); (1)(a), (5)(a), and (6)(i); (1)(a), (5)(a), and (6)(j); (1)(a), (5)(a), and (6)(k); (1)(a), (5)(a), and (6)(l); (1)(a), (5)(b), and (6)(a); (1)(a), (5)(b), and (6)(b); (1)(a), (5)(b), and (6)(c); (1)(a), (5)(b), and (6)(d); (1)(a), (5)(b), and (6)(e); (1)(a), (5)(b), and (6)(f); (1)(a), (5)(b), and (6)(g); (1)(a), (5)(b), and (6)(h); (1)(a), (5)(b), and (6)(i); (1)(a), (5)(b), and (6)(j); (1)(a), (5)(b), and (6)(k); (1)(a), (5)(b), and (6)(l); (1)(a), (5)(c), and (6)(a); (1)(a), (5)(c), and (6)(b); (1)(a), (5)(c), and (6)(c); (1)(a), (5)(c), and (6)(d); (1)(a), (5)(c), and (6)(e); (1)(a), (5)(c), and (6)(f); (1)(a), (5)(c), and (6)(g); (1)(a), (5)(c), and (6)(h); (1)(a), (5)(c), and (6)(i); (1)(a), (5)(c), and (6)(j); (1)(a), (5)(c), and (6)(k); (1)(a), (5)(c), and (6)(l); (1)(a), (5)(d), and (6)(a); (1)(a), (5)(d), and (6)(b); (1)(a), (5)(d), and (6)(c); (1)(a), (5)(d), and (6)(d); (1)(a), (5)(d), and (6)(e); (1)(a), (5)(d), and (6)(f); (1)(a), (5)(d), and (6)(g); (1)(a), (5)(d), and (6)(h); (1)(a), (5)(d), and (6)(i); (1)(a), (5)(d), and (6)(j); (1)(a), (5)(d), and (6)(k); (1)(a), (5)(d), and (6)(l); (1)(a), (5)(e), and (6)(a); (1)(a), (5)(e), and (6)(b); (1)(a), (5)(e), and (6)(c); (1)(a), (5)(e), and (6)(d); (1)(a), (5)(e), and (6)(e); (1)(a), (5)(e), and (6)(f); (1)(a), (5)(e), and (6)(g); (1)(a), (5)(e), and (6)(h); (1)(a), (5)(e), and (6)(i); (1)(a), (5)(e), and (6)(j); (1)(a), (5)(e), and (6)(k); (1)(a), (5)(e), and (6)(l); (1)(a), (5)(f), and (6)(a); (1)(a), (5)(f), and (6)(b); (1)(a), (5)(f), and (6)(c); (1)(a), (5)(f), and (6)(d); (1)(a), (5)(f), and (6)(e); (1)(a), (5)(f), and (6)(f); (1)(a), (5)(f), and (6)(g); (1)(a), (5)(f), and (6)(h); (1)(a), (5)(f), and (6)(i); (1)(a), (5)(f), and (6)(j); (1)(a), (5)(f), and (6)(k); (1)(a), (5)(f), and (6)(l); (1)(a), (5)(g), and (6)(a); (1)(a), (5)(g), and (6)(b); (1)(a), (5)(g), and (6)(c); (1)(a), (5)(g), and (6)(d); (1)(a), (5)(g), and (6)(e); (1)(a), (5)(g), and (6)(f); (1)(a), (5)(g), and (6)(g); (1)(a), (5)(g), and (6)(h); (1)(a), (5)(g), and (6)(i); (1)(a), (5)(g), and (6)(j); (1)(a), (5)(g), and (6)(k); (1)(a), (5)(g), and (6)(l); (1)(a), (5)(h), and (6)(a); (1)(a), (5)(h), and (6)(b); (1)(a), (5)(h), and (6)(c); (1)(a), (5)(h), and (6)(d); (1)(a), (5)(h), and (6)(e); (1)(a), (5)(h), and (6)(f); (1)(a), (5)(h), and (6)(g); (1)(a), (5)(h), and (6)(h); (1)(a), (5)(h), and (6)(i); (1)(a), (5)(h), and (6)(j); (1)(a), (5)(h), and (6)(k); (1)(a), (5)(h), and (6)(l); (1)(a), (5)(i), and (6)(a); (1)(a), (5)(i), and (6)(b); (1)(a), (5)(i), and (6)(c); (1)(a), (5)(i), and (6)(d); (1)(a), (5)(i), and (6)(e); (1)(a), (5)(i), and (6)(f); (1)(a), (5)(i), and (6)(g); (1)(a), (5)(i), and (6)(h); (1)(a), (5)(i), and (6)(i); (1)(a), (5)(i), and (6)(j); (1)(a), (5)(i), and (6)(k); (1)(a), (5)(i), and (6)(l); (1)(a), (5)(j), and (6)(a); (1)(a), (5)(j), and (6)(b); (1)(a), (5)(j), and (6)(c); (1)(a), (5)(j), and (6)(d); (1)(a), (5)(j), and (6)(e); (1)(a), (5)(j), and (6)(f); (1)(a), (5)(j), and (6)(g); (1)(a), (5)(j), and (6)(h); (1)(a), (5)(j), and (6)(i); (1)(a), (5)(j), and (6)(j); (1)(a), (5)(j), and (6)(k); (1)(a), (5)(j), and (6)(l); (1)(b), (5)(a), and (6)(a); (1)(b), (5)(a), and (6)(b); (1)(b), (5)(a), and (6)(c); (1)(b), (5)(a), and (6)(d); (1)(b), (5)(a), and (6)(e); (1)(b), (5)(a), and (6)(f); (1)(b), (5)(a), and (6)(g); (1)(b), (5)(a), and (6)(h); (1)(b), (5)(a), and (6)(i); (1)(b), (5)(a), and (6)(j); (1)(b), (5)(a), and (6)(k); (1)(b), (5)(a), and (6)(l); (1)(b), (5)(b), and (6)(a); (1)(b), (5)(b), and (6)(b); (1)(b), (5)(b), and (6)(c); (1)(b), (5)(b), and (6)(d); (1)(b), (5)(b), and (6)(e); (1)(b), (5)(b), and (6)(f); (1)(b), (5)(b), and (6)(g); (1)(b), (5)(b), and (6)(h); (1)(b), (5)(b), and (6)(i); (1)(b), (5)(b), and (6)(j); (1)(b), (5)(b), and (6)(k); (1)(b), (5)(b), and (6)(l); (1)(b), (5)(c), and (6)(a); (1)(b), (5)(c), and (6)(b); (1)(b), (5)(c), and (6)(c); (1)(b), (5)(c), and (6)(d); (1)(b), (5)(c), and (6)(e); (1)(b), (5)(c), and (6)(f); (1)(b), (5)(c), and (6)(g); (1)(b), (5)(c), and (6)(h); (1)(b), (5)(c), and (6)(i); (1)(b), (5)(c), and (6)(j); (1)(b), (5)(c), and (6)(k); (1)(b), (5)(c), and (6)(l); (1)(b), (5)(d), and (6)(a); (1)(b), (5)(d), and (6)(b); (1)(b), (5)(d), and (6)(c); (1)(b), (5)(d), and (6)(d); (1)(b), (5)(d), and (6)(e); (1)(b), (5)(d), and (6)(f); (1)(b), (5)(d), and (6)(g); (1)(b), (5)(d), and (6)(h); (1)(b), (5)(d), and (6)(i); (1)(b), (5)(d), and (6)(j); (1)(b), (5)(d), and (6)(k); (1)(b), (5)(d), and (6)(l); (1)(b), (5)(e), and (6)(a); (1)(b), (5)(e), and (6)(b); (1)(b), (5)(e), and (6)(c); (1)(b), (5)(e), and (6)(d); (1)(b), (5)(e), and (6)(e); (1)(b), (5)(e), and (6)(f); (1)(b), (5)(e), and (6)(g); (1)(b), (5)(e), and (6)(h); (1)(b), (5)(e), and (6)(i); (1)(b), (5)(e), and (6)(j); (1)(b), (5)(e), and (6)(k); (1)(b), (5)(e), and (6)(l); (1)(b), (5)(f), and (6)(a); (1)(b), (5)(f), and (6)(b); (1)(b), (5)(f), and (6)(c); (1)(b), (5)(f), and (6)(d); (1)(b), (5)(f), and (6)(e); (1)(b), (5)(f), and (6)(f); (1)(b), (5)(f), and (6)(g); (1)(b), (5)(f), and (6)(h); (1)(b), (5)(f), and (6)(i); (1)(b), (5)(f), and (6)(j); (1)(b), (5)(f), and (6)(k); (1)(b), (5)(f), and (6)(l); (1)(b), (5)(g), and (6)(a); (1)(b), (5)(g), and (6)(b); (1)(b), (5)(g), and (6)(c); (1)(b), (5)(g), and (6)(d); (1)(b), (5)(g), and (6)(e); (1)(b), (5)(g), and (6)(f); (1)(b), (5)(g), and (6)(g); (1)(b), (5)(g), and (6)(h); (1)(b), (5)(g), and (6)(i); (1)(b), (5)(g), and (6)(j); (1)(b), (5)(g), and (6)(k); (1)(b), (5)(g), and (6)(l); (1)(b), (5)(h), and (6)(a); (1)(b), (5)(h), and (6)(b); (1)(b), (5)(h), and (6)(c); (1)(b), (5)(h), and (6)(d); (1)(b), (5)(h), and (6)(e); (1)(b), (5)(h), and (6)(f); (1)(b), (5)(h), and (6)(g); (1)(b), (5)(h), and (6)(h); (1)(b), (5)(h), and (6)(i); (1)(b), (5)(h), and (6)(j); (1)(b), (5)(h), and (6)(k); (1)(b), (5)(h), and (6)(l); (1)(b), (5)(i), and (6)(a); (1)(b), (5)(i), and (6)(b); (1)(b), (5)(i), and (6)(c); (1)(b), (5)(i), and (6)(d); (1)(b), (5)(i), and (6)(e); (1)(b), (5)(i), and (6)(f); (1)(b), (5)(i), and (6)(g); (1)(b), (5)(i), and (6)(h); (1)(b), (5)(i), and (6)(i); (1)(b), (5)(i), and (6)(j); (1)(b), (5)(i), and (6)(k); (1)(b), (5)(i), and (6)(l); (1)(b), (5)(j), and (6)(a); (1)(b), (5)(j), and (6)(b); (1)(b), (5)(j), and (6)(c); (1)(b), (5)(j), and (6)(d); (1)(b), (5)(j), and (6)(e); (1)(b), (5)(j), and (6)(f); (1)(b), (5)(j), and (6)(g); (1)(b), (5)(j), and (6)(h); (1)(b), (5)(j), and (6)(i); (1)(b), (5)(j), and (6)(j); (1)(b), (5)(j), and (6)(k); (1)(b), (5)(j), and (6)(l); (1)(c), (5)(a), and (6)(a); (1)(c), (5)(a), and (6)(b); (1)(c), (5)(a), and (6)(c); (1)(c), (5)(a), and (6)(d); (1)(c), (5)(a), and (6)(e); (1)(c), (5)(a), and (6)(f); (1)(c), (5)(a), and (6)(g); (1)(c), (5)(a), and (6)(h); (1)(c), (5)(a), and (6)(i); (1)(c), (5)(a), and (6)(j); (1)(c), (5)(a), and (6)(k); (1)(c), (5)(a), and (6)(l); (1)(c), (5)(b), and (6)(a); (1)(c), (5)(b), and (6)(b); (1)(c), (5)(b), and (6)(c); (1)(c), (5)(b), and (6)(d); (1)(c), (5)(b), and (6)(e); (1)(c), (5)(b), and (6)(f); (1)(c), (5)(b), and (6)(g); (1)(c), (5)(b), and (6)(h); (1)(c), (5)(b), and (6)(i); (1)(c), (5)(b), and (6)(j); (1)(c), (5)(b), and (6)(k); (1)(c), (5)(b), and (6)(l); (1)(c), (5)(c), and (6)(a); (1)(c), (5)(c), and (6)(b); (1)(c), (5)(c), and (6)(c); (1)(c), (5)(c), and (6)(d); (1)(c), (5)(c), and (6)(e); (1)(c), (5)(c), and (6)(f); (1)(c), (5)(c), and (6)(g); (1)(c), (5)(c), and (6)(h); (1)(c), (5)(c), and (6)(i); (1)(c), (5)(c), and (6)(j); (1)(c), (5)(c), and (6)(k); (1)(c), (5)(c), and (6)(l); (1)(c), (5)(d), and (6)(a); (1)(c), (5)(d), and (6)(b); (1)(c), (5)(d), and (6)(c); (1)(c), (5)(d), and (6)(d); (1)(c), (5)(d), and (6)(e); (1)(c), (5)(d), and (6)(f); (1)(c), (5)(d), and (6)(g); (1)(c), (5)(d), and (6)(h); (1)(c), (5)(d), and (6)(i); (1)(c), (5)(d), and (6)(j); (1)(c), (5)(d), and (6)(k); (1)(c), (5)(d), and (6)(l); (1)(c), (5)(e), and (6)(a); (1)(c), (5)(e), and (6)(b); (1)(c), (5)(e), and (6)(c); (1)(c), (5)(e), and (6)(d); (1)(c), (5)(e), and (6)(e); (1)(c), (5)(e), and (6)(f); (1)(c), (5)(e), and (6)(g); (1)(c), (5)(e), and (6)(h); (1)(c), (5)(e), and (6)(i); (1)(c), (5)(e), and (6)(j); (1)(c), (5)(e), and (6)(k); (1)(c), (5)(e), and (6)(l); (1)(c), (5)(f), and (6)(a); (1)(c), (5)(f), and (6)(b); (1)(c), (5)(f), and (6)(c); (1)(c), (5)(f), and (6)(d); (1)(c), (5)(f), and (6)(e); (1)(c), (5)(f), and (6)(f); (1)(c), (5)(f), and (6)(g); (1)(c), (5)(f), and (6)(h); (1)(c), (5)(f), and (6)(i); (1)(c), (5)(f), and (6)(j); (1)(c), (5)(f), and (6)(k); (1)(c), (5)(f), and (6)(l); (1)(c), (5)(g), and (6)(a); (1)(c), (5)(g), and (6)(b); (1)(c), (5)(g), and (6)(c); (1)(c), (5)(g), and (6)(d); (1)(c), (5)(g), and (6)(e); (1)(c), (5)(g), and (6)(f); (1)(c), (5)(g), and (6)(g); (1)(c), (5)(g), and (6)(h); (1)(c), (5)(g), and (6)(i); (1)(c), (5)(g), and (6)(j); (1)(c), (5)(g), and (6)(k); (1)(c), (5)(g), and (6)(l); (1)(c), (5)(h), and (6)(a); (1)(c), (5)(h), and (6)(b); (1)(c), (5)(h), and (6)(c); (1)(c), (5)(h), and (6)(d); (1)(c), (5)(h), and (6)(e); (1)(c), (5)(h), and (6)(f); (1)(c), (5)(h), and (6)(g); (1)(c), (5)(h), and (6)(h); (1)(c), (5)(h), and (6)(i); (1)(c), (5)(h), and (6)(j); (1)(c), (5)(h), and (6)(k); (1)(c), (5)(h), and (6)(l); (1)(c), (5)(i), and (6)(a); (1)(c), (5)(i), and (6)(b); (1)(c), (5)(i), and (6)(c); (1)(c), (5)(i), and (6)(d); (1)(c), (5)(i), and (6)(e); (1)(c), (5)(i), and (6)(f); (1)(c), (5)(i), and (6)(g); (1)(c), (5)(i), and (6)(h); (1)(c), (5)(i), and (6)(i); (1)(c), (5)(i), and (6)(j); (1)(c), (5)(i), and (6)(k); (1)(c), (5)(i), and (6)(l); (1)(c), (5)(j), and (6)(a); (1)(c), (5)(j), and (6)(b); (1)(c), (5)(j), and (6)(c); (1)(c), (5)(j), and (6)(d); (1)(c), (5)(j), and (6)(e); (1)(c), (5)(j), and (6)(f); (1)(c), (5)(j), and (6)(g); (1)(c), (5)(j), and (6)(h); (1)(c), (5)(j), and (6)(i); (1)(c), (5)(j), and (6)(j); (1)(c), (5)(j), and (6)(k); (1)(c), (5)(j), and (6)(l); (1)(d), (5)(a), and (6)(a); (1)(d), (5)(a), and (6)(b); (1)(d), (5)(a), and (6)(c); (1)(d), (5)(a), and (6)(d); (1)(d), (5)(a), and (6)(e); (1)(d), (5)(a), and (6)(f); (1)(d), (5)(a), and (6)(g); (1)(d), (5)(a), and (6)(h); (1)(d), (5)(a), and (6)(i); (1)(d), (5)(a), and (6)(j); (1)(d), (5)(a), and (6)(k); (1)(d), (5)(a), and (6)(l); (1)(d), (5)(b), and (6)(a); (1)(d), (5)(b), and (6)(b); (1)(d), (5)(b), and (6)(c); (1)(d), (5)(b), and (6)(d); (1)(d), (5)(b), and (6)(e); (1)(d), (5)(b), and (6)(f); (1)(d), (5)(b), and (6)(g); (1)(d), (5)(b), and (6)(h); (1)(d), (5)(b), and (6)(i); (1)(d), (5)(b), and (6)(j); (1)(d), (5)(b), and (6)(k); (1)(d), (5)(b), and (6)(l); (1)(d), (5)(c), and (6)(a); (1)(d), (5)(c), and (6)(b); (1)(d), (5)(c), and (6)(c); (1)(d), (5)(c), and (6)(d); (1)(d), (5)(c), and (6)(e); (1)(d), (5)(c), and (6)(f); (1)(d), (5)(c), and (6)(g); (1)(d), (5)(c), and (6)(h); (1)(d), (5)(c), and (6)(i); (1)(d), (5)(c), and (6)(j); (1)(d), (5)(c), and (6)(k); (1)(d), (5)(c), and (6)(l); (1)(d), (5)(d), and (6)(a); (1)(d), (5)(d), and (6)(b); (1)(d), (5)(d), and (6)(c); (1)(d), (5)(d), and (6)(d); (1)(d), (5)(d), and (6)(e); (1)(d), (5)(d), and (6)(f); (1)(d), (5)(d), and (6)(g); (1)(d), (5)(d), and (6)(h); (1)(d), (5)(d), and (6)(i); (1)(d), (5)(d), and (6)(j); (1)(d), (5)(d), and (6)(k); (1)(d), (5)(d), and (6)(l); (1)(d), (5)(e), and (6)(a); (1)(d), (5)(e), and (6)(b); (1)(d), (5)(e), and (6)(c); (1)(d), (5)(e), and (6)(d); (1)(d), (5)(e), and (6)(e); (1)(d), (5)(e), and (6)(f); (1)(d), (5)(e), and (6)(g); (1)(d), (5)(e), and (6)(h); (1)(d), (5)(e), and (6)(i); (1)(d), (5)(e), and (6)(j); (1)(d), (5)(e), and (6)(k); (1)(d), (5)(e), and (6)(l); (1)(d), (5)(f), and (6)(a); (1)(d), (5)(f), and (6)(b); (1)(d), (5)(f), and (6)(c); (1)(d), (5)(f), and (6)(d); (1)(d), (5)(f), and (6)(e); (1)(d), (5)(f), and (6)(f); (1)(d), (5)(f), and (6)(g); (1)(d), (5)(f), and (6)(h); (1)(d), (5)(f), and (6)(i); (1)(d), (5)(f), and (6)(j); (1)(d), (5)(f), and (6)(k); (1)(d), (5)(f), and (6)(l); (1)(d), (5)(g), and (6)(a); (1)(d), (5)(g), and (6)(b); (1)(d), (5)(g), and (6)(c); (1)(d), (5)(g), and (6)(d); (1)(d), (5)(g), and (6)(e); (1)(d), (5)(g), and (6)(f); (1)(d), (5)(g), and (6)(g); (1)(d), (5)(g), and (6)(h); (1)(d), (5)(g), and (6)(i); (1)(d), (5)(g), and (6)(j); (1)(d), (5)(g), and (6)(k); (1)(d), (5)(g), and (6)(l); (1)(d), (5)(h), and (6)(a); (1)(d), (5)(h), and (6)(b); (1)(d), (5)(h), and (6)(c); (1)(d), (5)(h), and (6)(d); (1)(d), (5)(h), and (6)(e); (1)(d), (5)(h), and (6)(f); (1)(d), (5)(h), and (6)(g); (1)(d), (5)(h), and (6)(h); (1)(d), (5)(h), and (6)(i); (1)(d), (5)(h), and (6)(j); (1)(d), (5)(h), and (6)(k); (1)(d), (5)(h), and (6)(l); (1)(d), (5)(i), and (6)(a); (1)(d), (5)(i), and (6)(b); (1)(d), (5)(i), and (6)(c); (1)(d), (5)(i), and (6)(d); (1)(d), (5)(i), and (6)(e); (1)(d), (5)(i), and (6)(f); (1)(d), (5)(i), and (6)(g); (1)(d), (5)(i), and (6)(h); (1)(d), (5)(i), and (6)(i); (1)(d), (5)(i), and (6)(j); (1)(d), (5)(i), and (6)(k); (1)(d), (5)(i), and (6)(l); (1)(d), (5)(j), and (6)(a); (1)(d), (5)(j), and (6)(b); (1)(d), (5)(j), and (6)(c); (1)(d), (5)(j), and (6)(d); (1)(d), (5)(j), and (6)(e); (1)(d), (5)(j), and (6)(f); (1)(d), (5)(j), and (6)(g); (1)(d), (5)(j), and (6)(h); (1)(d), (5)(j), and (6)(i); (1)(d), (5)(j), and (6)(j); (1)(d), (5)(j), and (6)(k); (1)(d), (5)(j), and (6)(l); (1)(e), (5)(a), and (6)(a); (1)(e), (5)(a), and (6)(b); (1)(e), (5)(a), and (6)(c); (1)(e), (5)(a), and (6)(d); (1)(e), (5)(a), and (6)(e); (1)(e), (5)(a), and (6)(f); (1)(e), (5)(a), and (6)(g); (1)(e), (5)(a), and (6)(h); (1)(e), (5)(a), and (6)(i); (1)(e), (5)(a), and (6)(j); (1)(e), (5)(a), and (6)(k); (1)(e), (5)(a), and (6)(l); (1)(e), (5)(b), and (6)(a); (1)(e), (5)(b), and (6)(b); (1)(e), (5)(b), and (6)(c); (1)(e), (5)(b), and (6)(d); (1)(e), (5)(b), and (6)(e); (1)(e), (5)(b), and (6)(f); (1)(e), (5)(b), and (6)(g); (1)(e), (5)(b), and (6)(h); (1)(e), (5)(b), and (6)(i); (1)(e), (5)(b), and (6)(j); (1)(e), (5)(b), and (6)(k); (1)(e), (5)(b), and (6)(l); (1)(e), (5)(c), and (6)(a); (1)(e), (5)(c), and (6)(b); (1)(e), (5)(c), and (6)(c); (1)(e), (5)(c), and (6)(d); (1)(e), (5)(c), and (6)(e); (1)(e), (5)(c), and (6)(f); (1)(e), (5)(c), and (6)(g); (1)(e), (5)(c), and (6)(h); (1)(e), (5)(c), and (6)(i); (1)(e), (5)(c), and (6)(j); (1)(e), (5)(c), and (6)(k); (1)(e), (5)(c), and (6)(l); (1)(e), (5)(d), and (6)(a); (1)(e), (5)(d), and (6)(b); (1)(e), (5)(d), and (6)(c); (1)(e), (5)(d), and (6)(d); (1)(e), (5)(d), and (6)(e); (1)(e), (5)(d), and (6)(f); (1)(e), (5)(d), and (6)(g); (1)(e), (5)(d), and (6)(h); (1)(e), (5)(d), and (6)(i); (1)(e), (5)(d), and (6)(j); (1)(e), (5)(d), and (6)(k); (1)(e), (5)(d), and (6)(l); (1)(e), (5)(e), and (6)(a); (1)(e), (5)(e), and (6)(b); (1)(e), (5)(e), and (6)(c); (1)(e), (5)(e), and (6)(d); (1)(e), (5)(e), and (6)(e); (1)(e), (5)(e), and (6)(f); (1)(e), (5)(e), and (6)(g); (1)(e), (5)(e), and (6)(h); (1)(e), (5)(e), and (6)(i); (1)(e), (5)(e), and (6)(j); (1)(e), (5)(e), and (6)(k); (1)(e), (5)(e), and (6)(l); (1)(e), (5)(f), and (6)(a); (1)(e), (5)(f), and (6)(b); (1)(e), (5)(f), and (6)(c); (1)(e), (5)(f), and (6)(d); (1)(e), (5)(f), and (6)(e); (1)(e), (5)(f), and (6)(f); (1)(e), (5)(f), and (6)(g); (1)(e), (5)(f), and (6)(h); (1)(e), (5)(f), and (6)(i); (1)(e), (5)(f), and (6)(j); (1)(e), (5)(f), and (6)(k); (1)(e), (5)(f), and (6)(l); (1)(e), (5)(g), and (6)(a); (1)(e), (5)(g), and (6)(b); (1)(e), (5)(g), and (6)(c); (1)(e), (5)(g), and (6)(d); (1)(e), (5)(g), and (6)(e); (1)(e), (5)(g), and (6)(f); (1)(e), (5)(g), and (6)(g); (1)(e), (5)(g), and (6)(h); (1)(e), (5)(g), and (6)(i); (1)(e), (5)(g), and (6)(j); (1)(e), (5)(g), and (6)(k); (1)(e), (5)(g), and (6)(l); (1)(e), (5)(h), and (6)(a); (1)(e), (5)(h), and (6)(b); (1)(e), (5)(h), and (6)(c); (1)(e), (5)(h), and (6)(d); (1)(e), (5)(h), and (6)(e); (1)(e), (5)(h), and (6)(f); (1)(e), (5)(h), and (6)(g); (1)(e), (5)(h), and (6)(h); (1)(e), (5)(h), and (6)(i); (1)(e), (5)(h), and (6)(j); (1)(e), (5)(h), and (6)(k); (1)(e), (5)(h), and (6)(l); (1)(e), (5)(i), and (6)(a); (1)(e), (5)(i), and (6)(b); (1)(e), (5)(i), and (6)(c); (1)(e), (5)(i), and (6)(d); (1)(e), (5)(i), and (6)(e); (1)(e), (5)(i), and (6)(f); (1)(e), (5)(i), and (6)(g); (1)(e), (5)(i), and (6)(h); (1)(e), (5)(i), and (6)(i); (1)(e), (5)(i), and (6)(j); (1)(e), (5)(i), and (6)(k); (1)(e), (5)(i), and (6)(l); (1)(e), (5)(j), and (6)(a); (1)(e), (5)(j), and (6)(b); (1)(e), (5)(j), and (6)(c); (1)(e), (5)(j), and (6)(d); (1)(e), (5)(j), and (6)(e); (1)(e), (5)(j), and (6)(f); (1)(e), (5)(j), and (6)(g); (1)(e), (5)(j), and (6)(h); (1)(e), (5)(j), and (6)(i); (1)(e), (5)(j), and (6)(j); (1)(e), (5)(j), and (6)(k); (1)(e), (5)(j), and (6)(l); (1)(f), (5)(a), and (6)(a); (1)(f), (5)(a), and (6)(b); (1)(f), (5)(a), and (6)(c); (1)(f), (5)(a), and (6)(d); (1)(f), (5)(a), and (6)(e); (1)(f), (5)(a), and (6)(f); (1)(f), (5)(a), and (6)(g); (1)(f), (5)(a), and (6)(h); (1)(f), (5)(a), and (6)(i); (1)(f), (5)(a), and (6)(j); (1)(f), (5)(a), and (6)(k); (1)(f), (5)(a), and (6)(l); (1)(f), (5)(b), and (6)(a); (1)(f), (5)(b), and (6)(b); (1)(f), (5)(b), and (6)(c); (1)(f), (5)(b), and (6)(d); (1)(f), (5)(b), and (6)(e); (1)(f), (5)(b), and (6)(f); (1)(f), (5)(b), and (6)(g); (1)(f), (5)(b), and (6)(h); (1)(f), (5)(b), and (6)(i); (1)(f), (5)(b), and (6)(j); (1)(f), (5)(b), and (6)(k); (1)(f), (5)(b), and (6)(l); (1)(f), (5)(c), and (6)(a); (1)(f), (5)(c), and (6)(b); (1)(f), (5)(c), and (6)(c); (1)(f), (5)(c), and (6)(d); (1)(f), (5)(c), and (6)(e); (1)(f), (5)(c), and (6)(f); (1)(f), (5)(c), and (6)(g); (1)(f), (5)(c), and (6)(h); (1)(f), (5)(c), and (6)(i); (1)(f), (5)(c), and (6)(j); (1)(f), (5)(c), and (6)(k); (1)(f), (5)(c), and (6)(l); (1)(f), (5)(d), and (6)(a); (1)(f), (5)(d), and (6)(b); (1)(f), (5)(d), and (6)(c); (1)(f), (5)(d), and (6)(d); (1)(f), (5)(d), and (6)(e); (1)(f), (5)(d), and (6)(f); (1)(f), (5)(d), and (6)(g); (1)(f), (5)(d), and (6)(h); (1)(f), (5)(d), and (6)(i); (1)(f), (5)(d), and (6)(j); (1)(f), (5)(d), and (6)(k); (1)(f), (5)(d), and (6)(l); (1)(f), (5)(e), and (6)(a); (1)(f), (5)(e), and (6)(b); (1)(f), (5)(e), and (6)(c); (1)(f), (5)(e), and (6)(d); (1)(f), (5)(e), and (6)(e); (1)(f), (5)(e), and (6)(f); (1)(f), (5)(e), and (6)(g); (1)(f), (5)(e), and (6)(h); (1)(f), (5)(e), and (6)(i); (1)(f), (5)(e), and (6)(j); (1)(f), (5)(e), and (6)(k); (1)(f), (5)(e), and (6)(l); (1)(f), (5)(f), and (6)(a); (1)(f), (5)(f), and (6)(b); (1)(f), (5)(f), and (6)(c); (1)(f), (5)(f), and (6)(d); (1)(f), (5)(f), and (6)(e); (1)(f), (5)(f), and (6)(f); (1)(f), (5)(f), and (6)(g); (1)(f), (5)(f), and (6)(h); (1)(f), (5)(f), and (6)(i); (1)(f), (5)(f), and (6)(j); (1)(f), (5)(f), and (6)(k); (1)(f), (5)(f), and (6)(l); (1)(f), (5)(g), and (6)(a); (1)(f), (5)(g), and (6)(b); (1)(f), (5)(g), and (6)(c); (1)(f), (5)(g), and (6)(d); (1)(f), (5)(g), and (6)(e); (1)(f), (5)(g), and (6)(f); (1)(f), (5)(g), and (6)(g); (1)(f), (5)(g), and (6)(h); (1)(f), (5)(g), and (6)(i); (1)(f), (5)(g), and (6)(j); (1)(f), (5)(g), and (6)(k); (1)(f), (5)(g), and (6)(l); (1)(f), (5)(h), and (6)(a); (1)(f), (5)(h), and (6)(b); (1)(f), (5)(h), and (6)(c); (1)(f), (5)(h), and (6)(d); (1)(f), (5)(h), and (6)(e); (1)(f), (5)(h), and (6)(f); (1)(f), (5)(h), and (6)(g); (1)(f), (5)(h), and (6)(h); (1)(f), (5)(h), and (6)(i); (1)(f), (5)(h), and (6)(j); (1)(f), (5)(h), and (6)(k); (1)(f), (5)(h), and (6)(l); (1)(f), (5)(i), and (6)(a); (1)(f), (5)(i), and (6)(b); (1)(f), (5)(i), and (6)(c); (1)(f), (5)(i), and (6)(d); (1)(f), (5)(i), and (6)(e); (1)(f), (5)(i), and (6)(f); (1)(f), (5)(i), and (6)(g); (1)(f), (5)(i), and (6)(h); (1)(f), (5)(i), and (6)(i); (1)(f), (5)(i), and (6)(j); (1)(f), (5)(i), and (6)(k); (1)(f), (5)(i), and (6)(l); (1)(f), (5)(j), and (6)(a); (1)(f), (5)(j), and (6)(b); (1)(f), (5)(j), and (6)(c); (1)(f), (5)(j), and (6)(d); (1)(f), (5)(j), and (6)(e); (1)(f), (5)(j), and (6)(f); (1)(f), (5)(j), and (6)(g); (1)(f), (5)(j), and (6)(h); (1)(f), (5)(j), and (6)(i); (1)(f), (5)(j), and (6)(j); (1)(f), (5)(j), and (6)(k); (1)(f), (5)(j), and (6)(l); (1)(g), (5)(a), and (6)(a); (1)(g), (5)(a), and (6)(b); (1)(g), (5)(a), and (6)(c); (1)(g), (5)(a), and (6)(d); (1)(g), (5)(a), and (6)(e); (1)(g), (5)(a), and (6)(f); (1)(g), (5)(a), and (6)(g); (1)(g), (5)(a), and (6)(h); (1)(g), (5)(a), and (6)(i); (1)(g), (5)(a), and (6)(j); (1)(g), (5)(a), and (6)(k); (1)(g), (5)(a), and (6)(l); (1)(g), (5)(b), and (6)(a); (1)(g), (5)(b), and (6)(b); (1)(g), (5)(b), and (6)(c); (1)(g), (5)(b), and (6)(d); (1)(g), (5)(b), and (6)(e); (1)(g), (5)(b), and (6)(f); (1)(g), (5)(b), and (6)(g); (1)(g), (5)(b), and (6)(h); (1)(g), (5)(b), and (6)(i); (1)(g), (5)(b), and (6)(j); (1)(g), (5)(b), and (6)(k); (1)(g), (5)(b), and (6)(l); (1)(g), (5)(c), and (6)(a); (1)(g), (5)(c), and (6)(b); (1)(g), (5)(c), and (6)(c); (1)(g), (5)(c), and (6)(d); (1)(g), (5)(c), and (6)(e); (1)(g), (5)(c), and (6)(f); (1)(g), (5)(c), and (6)(g); (1)(g), (5)(c), and (6)(h); (1)(g), (5)(c), and (6)(i); (1)(g), (5)(c), and (6)(j); (1)(g), (5)(c), and (6)(k); (1)(g), (5)(c), and (6)(l); (1)(g), (5)(d), and (6)(a); (1)(g), (5)(d), and (6)(b); (1)(g), (5)(d), and (6)(c); (1)(g), (5)(d), and (6)(d); (1)(g), (5)(d), and (6)(e); (1)(g), (5)(d), and (6)(f); (1)(g), (5)(d), and (6)(g); (1)(g), (5)(d), and (6)(h); (1)(g), (5)(d), and (6)(i); (1)(g), (5)(d), and (6)(j); (1)(g), (5)(d), and (6)(k); (1)(g), (5)(d), and (6)(l); (1)(g), (5)(e), and (6)(a); (1)(g), (5)(e), and (6)(b); (1)(g), (5)(e), and (6)(c); (1)(g), (5)(e), and (6)(d); (1)(g), (5)(e), and (6)(e); (1)(g), (5)(e), and (6)(f); (1)(g), (5)(e), and (6)(g); (1)(g), (5)(e), and (6)(h); (1)(g), (5)(e), and (6)(i); (1)(g), (5)(e), and (6)(j); (1)(g), (5)(e), and (6)(k); (1)(g), (5)(e), and (6)(l); (1)(g), (5)(f), and (6)(a); (1)(g), (5)(f), and (6)(b); (1)(g), (5)(f), and (6)(c); (1)(g), (5)(f), and (6)(d); (1)(g), (5)(f), and (6)(e); (1)(g), (5)(f), and (6)(f); (1)(g), (5)(f), and (6)(g); (1)(g), (5)(f), and (6)(h); (1)(g), (5)(f), and (6)(i); (1)(g), (5)(f), and (6)(j); (1)(g), (5)(f), and (6)(k); (1)(g), (5)(f), and (6)(l); (1)(g), (5)(g), and (6)(a); (1)(g), (5)(g), and (6)(b); (1)(g), (5)(g), and (6)(c); (1)(g), (5)(g), and (6)(d); (1)(g), (5)(g), and (6)(e); (1)(g), (5)(g), and (6)(f); (1)(g), (5)(g), and (6)(g); (1)(g), (5)(g), and (6)(h); (1)(g), (5)(g), and (6)(i); (1)(g), (5)(g), and (6)(j); (1)(g), (5)(g), and (6)(k); (1)(g), (5)(g), and (6)(l); (1)(g), (5)(h), and (6)(a); (1)(g), (5)(h), and (6)(b); (1)(g), (5)(h), and (6)(c); (1)(g), (5)(h), and (6)(d); (1)(g), (5)(h), and (6)(e); (1)(g), (5)(h), and (6)(f); (1)(g), (5)(h), and (6)(g); (1)(g), (5)(h), and (6)(h); (1)(g), (5)(h), and (6)(i); (1)(g), (5)(h), and (6)(j); (1)(g), (5)(h), and (6)(k); (1)(g), (5)(h), and (6)(l); (1)(g), (5)(i), and (6)(a); (1)(g), (5)(i), and (6)(b); (1)(g), (5)(i), and (6)(c); (1)(g), (5)(i), and (6)(d); (1)(g), (5)(i), and (6)(e); (1)(g), (5)(i), and (6)(f); (1)(g), (5)(i), and (6)(g); (1)(g), (5)(i), and (6)(h); (1)(g), (5)(i), and (6)(i); (1)(g), (5)(i), and (6)(j); (1)(g), (5)(i), and (6)(k); (1)(g), (5)(i), and (6)(l); (1)(g), (5)(j), and (6)(a); (1)(g), (5)(j), and (6)(b); (1)(g), (5)(j), and (6)(c); (1)(g), (5)(j), and (6)(d); (1)(g), (5)(j), and (6)(e); (1)(g), (5)(j), and (6)(f); (1)(g), (5)(j), and (6)(g); (1)(g), (5)(j), and (6)(h); (1)(g), (5)(j), and (6)(i); (1)(g), (5)(j), and (6)(j); (1)(g), (5)(j), and (6)(k); (1)(g), (5)(j), and (6)(l); (1)(h), (5)(a), and (6)(a); (1)(h), (5)(a), and (6)(b); (1)(h), (5)(a), and (6)(c); (1)(h), (5)(a), and (6)(d); (1)(h), (5)(a), and (6)(e); (1)(h), (5)(a), and (6)(f); (1)(h), (5)(a), and (6)(g); (1)(h), (5)(a), and (6)(h); (1)(h), (5)(a), and (6)(i); (1)(h), (5)(a), and (6)(j); (1)(h), (5)(a), and (6)(k); (1)(h), (5)(a), and (6)(l); (1)(h), (5)(b), and (6)(a); (1)(h), (5)(b), and (6)(b); (1)(h), (5)(b), and (6)(c); (1)(h), (5)(b), and (6)(d); (1)(h), (5)(b), and (6)(e); (1)(h), (5)(b), and (6)(f); (1)(h), (5)(b), and (6)(g); (1)(h), (5)(b), and (6)(h); (1)(h), (5)(b), and (6)(i); (1)(h), (5)(b), and (6)(j); (1)(h), (5)(b), and (6)(k); (1)(h), (5)(b), and (6)(l); (1)(h), (5)(c), and (6)(a); (1)(h), (5)(c), and (6)(b); (1)(h), (5)(c), and (6)(c); (1)(h), (5)(c), and (6)(d); (1)(h), (5)(c), and (6)(e); (1)(h), (5)(c), and (6)(f); (1)(h), (5)(c), and (6)(g); (1)(h), (5)(c), and (6)(h); (1)(h), (5)(c), and (6)(i); (1)(h), (5)(c), and (6)(j); (1)(h), (5)(c), and (6)(k); (1)(h), (5)(c), and (6)(l); (1)(h), (5)(d), and (6)(a); (1)(h), (5)(d), and (6)(b); (1)(h), (5)(d), and (6)(c); (1)(h), (5)(d), and (6)(d); (1)(h), (5)(d), and (6)(e); (1)(h), (5)(d), and (6)(f); (1)(h), (5)(d), and (6)(g); (1)(h), (5)(d), and (6)(h); (1)(h), (5)(d), and (6)(i); (1)(h), (5)(d), and (6)(j); (1)(h), (5)(d), and (6)(k); (1)(h), (5)(d), and (6)(l); (1)(h), (5)(e), and (6)(a); (1)(h), (5)(e), and (6)(b); (1)(h), (5)(e), and (6)(c); (1)(h), (5)(e), and (6)(d); (1)(h), (5)(e), and (6)(e); (1)(h), (5)(e), and (6)(f); (1)(h), (5)(e), and (6)(g); (1)(h), (5)(e), and (6)(h); (1)(h), (5)(e), and (6)(i); (1)(h), (5)(e), and (6)(j); (1)(h), (5)(e), and (6)(k); (1)(h), (5)(e), and (6)(l); (1)(h), (5)(f), and (6)(a); (1)(h), (5)(f), and (6)(b); (1)(h), (5)(f), and (6)(c); (1)(h), (5)(f), and (6)(d); (1)(h), (5)(f), and (6)(e); (1)(h), (5)(f), and (6)(f); (1)(h), (5)(f), and (6)(g); (1)(h), (5)(f), and (6)(h); (1)(h), (5)(f), and (6)(i); (1)(h), (5)(f), and (6)(j); (1)(h), (5)(f), and (6)(k); (1)(h), (5)(f), and (6)(l); (1)(h), (5)(g), and (6)(a); (1)(h), (5)(g), and (6)(b); (1)(h), (5)(g), and (6)(c); (1)(h), (5)(g), and (6)(d); (1)(h), (5)(g), and (6)(e); (1)(h), (5)(g), and (6)(f); (1)(h), (5)(g), and (6)(g); (1)(h), (5)(g), and (6)(h); (1)(h), (5)(g), and (6)(i); (1)(h), (5)(g), and (6)(j); (1)(h), (5)(g), and (6)(k); (1)(h), (5)(g), and (6)(l); (1)(h), (5)(h), and (6)(a); (1)(h), (5)(h), and (6)(b); (1)(h), (5)(h), and (6)(c); (1)(h), (5)(h), and (6)(d); (1)(h), (5)(h), and (6)(e); (1)(h), (5)(h), and (6)(f); (1)(h), (5)(h), and (6)(g); (1)(h), (5)(h), and (6)(h); (1)(h), (5)(h), and (6)(i); (1)(h), (5)(h), and (6)(j); (1)(h), (5)(h), and (6)(k); (1)(h), (5)(h), and (6)(l); (1)(h), (5)(i), and (6)(a); (1)(h), (5)(i), and (6)(b); (1)(h), (5)(i), and (6)(c); (1)(h), (5)(i), and (6)(d); (1)(h), (5)(i), and (6)(e); (1)(h), (5)(i), and (6)(f); (1)(h), (5)(i), and (6)(g); (1)(h), (5)(i), and (6)(h); (1)(h), (5)(i), and (6)(i); (1)(h), (5)(i), and (6)(j); (1)(h), (5)(i), and (6)(k); (1)(h), (5)(i), and (6)(l); (1)(h), (5)(j), and (6)(a); (1)(h), (5)(j), and (6)(b); (1)(h), (5)(j), and (6)(c); (1)(h), (5)(j), and (6)(d); (1)(h), (5)(j), and (6)(e); (1)(h), (5)(j), and (6)(f); (1)(h), (5)(j), and (6)(g); (1)(h), (5)(j), and (6)(h); (1)(h), (5)(j), and (6)(i); (1)(h), (5)(j), and (6)(j); (1)(h), (5)(j), and (6)(k); (1)(h), (5)(j), and (6)(l); (1)(i), (5)(a), and (6)(a); (1)(i), (5)(a), and (6)(b); (1)(i), (5)(a), and (6)(c); (1)(i), (5)(a), and (6)(d); (1)(i), (5)(a), and (6)(e); (1)(i), (5)(a), and (6)(f); (1)(i), (5)(a), and (6)(g); (1)(i), (5)(a), and (6)(h); (1)(i), (5)(a), and (6)(i); (1)(i), (5)(a), and (6)(j); (1)(i), (5)(a), and (6)(k); (1)(i), (5)(a), and (6)(l); (1)(i), (5)(b), and (6)(a); (1)(i), (5)(b), and (6)(b); (1)(i), (5)(b), and (6)(c); (1)(i), (5)(b), and (6)(d); (1)(i), (5)(b), and (6)(e); (1)(i), (5)(b), and (6)(f); (1)(i), (5)(b), and (6)(g); (1)(i), (5)(b), and (6)(h); (1)(i), (5)(b), and (6)(i); (1)(i), (5)(b), and (6)(j); (1)(i), (5)(b), and (6)(k); (1)(i), (5)(b), and (6)(l); (1)(i), (5)(c), and (6)(a); (1)(i), (5)(c), and (6)(b); (1)(i), (5)(c), and (6)(c); (1)(i), (5)(c), and (6)(d); (1)(i), (5)(c), and (6)(e); (1)(i), (5)(c), and (6)(f); (1)(i), (5)(c), and (6)(g); (1)(i), (5)(c), and (6)(h); (1)(i), (5)(c), and (6)(i); (1)(i), (5)(c), and (6)(j); (1)(i), (5)(c), and (6)(k); (1)(i), (5)(c), and (6)(l); (1)(i), (5)(d), and (6)(a); (1)(i), (5)(d), and (6)(b); (1)(i), (5)(d), and (6)(c); (1)(i), (5)(d), and (6)(d); (1)(i), (5)(d), and (6)(e); (1)(i), (5)(d), and (6)(f); (1)(i), (5)(d), and (6)(g); (1)(i), (5)(d), and (6)(h); (1)(i), (5)(d), and (6)(i); (1)(i), (5)(d), and (6)(j); (1)(i), (5)(d), and (6)(k); (1)(i), (5)(d), and (6)(l); (1)(i), (5)(e), and (6)(a); (1)(i), (5)(e), and (6)(b); (1)(i), (5)(e), and (6)(c); (1)(i), (5)(e), and (6)(d); (1)(i), (5)(e), and (6)(e); (1)(i), (5)(e), and (6)(f); (1)(i), (5)(e), and (6)(g); (1)(i), (5)(e), and (6)(h); (1)(i), (5)(e), and (6)(i); (1)(i), (5)(e), and (6)(j); (1)(i), (5)(e), and (6)(k); (1)(i), (5)(e), and (6)(l); (1)(i), (5)(f), and (6)(a); (1)(i), (5)(f), and (6)(b); (1)(i), (5)(f), and (6)(c);

(1)(i), (5)(f), and (6)(d); (1)(i), (5)(f), and (6)(e); (1)(i), (5)(f), and (6)(f); (1)(i), (5)(f), and (6)(g); (1)(i), (5)(f), and (6)(h); (1)(i), (5)(f), and (6)(i); (1)(i), (5)(f), and (6)(j); (1)(i), (5)(f), and (6)(k); (1)(i), (5)(f), and (6)(l); (1)(i), (5)(g), and (6)(a); (1)(i), (5)(g), and (6)(b); (1)(i), (5)(g), and (6)(c); (1)(i), (5)(g), and (6)(d); (1)(i), (5)(g), and (6)(e); (1)(i), (5)(g), and (6)(f); (1)(i), (5)(g), and (6)(g); (1)(i), (5)(g), and (6)(h); (1)(i), (5)(g), and (6)(i); (1)(i), (5)(g), and (6)(j); (1)(i), (5)(g), and (6)(k); (1)(i), (5)(g), and (6)(l); (1)(i), (5)(h), and (6)(a); (1)(i), (5)(h), and (6)(b); (1)(i), (5)(h), and (6)(c); (1)(i), (5)(h), and (6)(d); (1)(i), (5)(h), and (6)(e); (1)(i), (5)(h), and (6)(f); (1)(i), (5)(h), and (6)(g); (1)(i), (5)(h), and (6)(h); (1)(i), (5)(h), and (6)(i); (1)(i), (5)(h), and (6)(j); (1)(i), (5)(h), and (6)(k); (1)(i), (5)(h), and (6)(l); (1)(i), (5)(i), and (6)(a); (1)(i), (5)(i), and (6)(b); (1)(i), (5)(i), and (6)(c); (1)(i), (5)(i), and (6)(d); (1)(i), (5)(i), and (6)(e); (1)(i), (5)(i), and (6)(f); (1)(i), (5)(i), and (6)(g); (1)(i), (5)(i), and (6)(h); (1)(i), (5)(i), and (6)(i); (1)(i), (5)(i), and (6)(j); (1)(i), (5)(i), and (6)(k); (1)(i), (5)(i), and (6)(l); (1)(i), (5)(j), and (6)(a); (1)(i), (5)(j), and (6)(b); (1)(i), (5)(j), and (6)(c); (1)(i), (5)(j), and (6)(d); (1)(i), (5)(j), and (6)(e); (1)(i), (5)(j), and (6)(f); (1)(i), (5)(j), and (6)(g); (1)(i), (5)(j), and (6)(h); (1)(i), (5)(j), and (6)(i); (1)(i), (5)(j), and (6)(j); (1)(i), (5)(j), and (6)(k); (1)(i), (5)(j), and (6)(l); (1)(j), (5)(a), and (6)(a); (1)(j), (5)(a), and (6)(b); (1)(j), (5)(a), and (6)(c); (1)(j), (5)(a), and (6)(d); (1)(j), (5)(a), and (6)(e); (1)(j), (5)(a), and (6)(f); (1)(j), (5)(a), and (6)(g); (1)(j), (5)(a), and (6)(h); (1)(j), (5)(a), and (6)(i); (1)(j), (5)(a), and (6)(j); (1)(j), (5)(a), and (6)(k); (1)(j), (5)(a), and (6)(l); (1)(j), (5)(b), and (6)(a); (1)(j), (5)(b), and (6)(b); (1)(j), (5)(b), and (6)(c); (1)(j), (5)(b), and (6)(d); (1)(j), (5)(b), and (6)(e); (1)(j), (5)(b), and (6)(f); (1)(j), (5)(b), and (6)(g); (1)(j), (5)(b), and (6)(h); (1)(j), (5)(b), and (6)(i); (1)(j), (5)(b), and (6)(j); (1)(j), (5)(b), and (6)(k); (1)(j), (5)(b), and (6)(l); (1)(j), (5)(c), and (6)(a); (1)(j), (5)(c), and (6)(b); (1)(j), (5)(c), and (6)(c); (1)(j), (5)(c), and (6)(d); (1)(j), (5)(c), and (6)(e); (1)(j), (5)(c), and (6)(f); (1)(j), (5)(c), and (6)(g); (1)(j), (5)(c), and (6)(h); (1)(j), (5)(c), and (6)(i); (1)(j), (5)(c), and (6)(j); (1)(j), (5)(c), and (6)(k); (1)(j), (5)(c), and (6)(l); (1)(j), (5)(d), and (6)(a); (1)(j), (5)(d), and (6)(b); (1)(j), (5)(d), and (6)(c); (1)(j), (5)(d), and (6)(d); (1)(j), (5)(d), and (6)(e); (1)(j), (5)(d), and (6)(f); (1)(j), (5)(d), and (6)(g); (1)(j), (5)(d), and (6)(h); (1)(j), (5)(d), and (6)(i); (1)(j), (5)(d), and (6)(j); (1)(j), (5)(d), and (6)(k); (1)(j), (5)(d), and (6)(l); (1)(j), (5)(e), and (6)(a); (1)(j), (5)(e), and (6)(b); (1)(j), (5)(e), and (6)(c); (1)(j), (5)(e), and (6)(d); (1)(j), (5)(e), and (6)(e); (1)(j), (5)(e), and (6)(f); (1)(j), (5)(e), and (6)(g); (1)(j), (5)(e), and (6)(h); (1)(j), (5)(e), and (6)(i); (1)(j), (5)(e), and (6)(j); (1)(j), (5)(e), and (6)(k); (1)(j), (5)(e), and (6)(l); (1)(j), (5)(f), and (6)(a); (1)(j), (5)(f), and (6)(b); (1)(j), (5)(f), and (6)(c); (1)(j), (5)(f), and (6)(d); (1)(j), (5)(f), and (6)(e); (1)(j), (5)(f), and (6)(f); (1)(j), (5)(f), and (6)(g); (1)(j), (5)(f), and (6)(h); (1)(j), (5)(f), and (6)(i); (1)(j), (5)(f), and (6)(j); (1)(j), (5)(f), and (6)(k); (1)(j), (5)(f), and (6)(l); (1)(j), (5)(g), and (6)(a); (1)(j), (5)(g), and (6)(b); (1)(j), (5)(g), and (6)(c); (1)(j), (5)(g), and (6)(d); (1)(j), (5)(g), and (6)(e); (1)(j), (5)(g), and (6)(f); (1)(j), (5)(g), and (6)(g); (1)(j), (5)(g), and (6)(h); (1)(j), (5)(g), and (6)(i); (1)(j), (5)(g), and (6)(j); (1)(j), (5)(g), and (6)(k); (1)(j), (5)(g), and (6)(l); (1)(j), (5)(h), and (6)(a); (1)(j), (5)(h), and (6)(b); (1)(j), (5)(h), and (6)(c); (1)(j), (5)(h), and (6)(d); (1)(j), (5)(h), and (6)(e); (1)(j), (5)(h), and (6)(f); (1)(j), (5)(h), and (6)(g); (1)(j), (5)(h), and (6)(h); (1)(j), (5)(h), and (6)(i); (1)(j), (5)(h), and (6)(j); (1)(j), (5)(h), and (6)(k); (1)(j), (5)(h), and (6)(l); (1)(j), (5)(i), and (6)(a); (1)(j), (5)(i), and (6)(b); (1)(j), (5)(i), and (6)(c); (1)(j), (5)(i), and (6)(d); (1)(j), (5)(i), and (6)(e); (1)(j), (5)(i), and (6)(f); (1)(j), (5)(i), and (6)(g); (1)(j), (5)(i), and (6)(h); (1)(j), (5)(i), and (6)(i); (1)(j), (5)(i), and (6)(j); (1)(j), (5)(i), and (6)(k); (1)(j), (5)(i), and (6)(l); (1)(j), (5)(j), and (6)(a); (1)(j), (5)(j), and (6)(b); (1)(j), (5)(j), and (6)(c); (1)(j), (5)(j), and (6)(d); (1)(j), (5)(j), and (6)(e); (1)(j), (5)(j), and (6)(f); (1)(j), (5)(j), and (6)(g); (1)(j), (5)(j), and (6)(h); (1)(j), (5)(j), and (6)(i); (1)(j), (5)(j), and (6)(j); (1)(j), (5)(j), and (6)(k); (1)(j), (5)(j), and (6)(l); (1)(k), (5)(a), and (6)(a); (1)(k), (5)(a), and (6)(b); (1)(k), (5)(a), and (6)(c); (1)(k), (5)(a), and (6)(d); (1)(k), (5)(a), and (6)(e); (1)(k), (5)(a), and (6)(f); (1)(k), (5)(a), and (6)(g); (1)(k), (5)(a), and (6)(h); (1)(k), (5)(a), and (6)(i); (1)(k), (5)(a), and (6)(j); (1)(k), (5)(a), and (6)(k); (1)(k), (5)(a), and (6)(l); (1)(k), (5)(b), and (6)(a); (1)(k), (5)(b), and (6)(b); (1)(k), (5)(b), and (6)(c); (1)(k), (5)(b), and (6)(d); (1)(k), (5)(b), and (6)(e); (1)(k), (5)(b), and (6)(f); (1)(k), (5)(b), and (6)(g); (1)(k), (5)(b), and (6)(h); (1)(k), (5)(b), and (6)(i); (1)(k), (5)(b), and (6)(j); (1)(k), (5)(b), and (6)(k); (1)(k), (5)(b), and (6)(l); (1)(k), (5)(c), and (6)(a); (1)(k), (5)(c), and (6)(b); (1)(k), (5)(c), and (6)(c); (1)(k), (5)(c), and (6)(d); (1)(k), (5)(c), and (6)(e); (1)(k), (5)(c), and (6)(f); (1)(k), (5)(c), and (6)(g); (1)(k), (5)(c), and (6)(h); (1)(k), (5)(c), and (6)(i); (1)(k), (5)(c), and (6)(j); (1)(k), (5)(c), and (6)(k); (1)(k), (5)(c), and (6)(l); (1)(k), (5)(d), and (6)(a); (1)(k), (5)(d), and (6)(b); (1)(k), (5)(d), and (6)(c); (1)(k), (5)(d), and (6)(d); (1)(k), (5)(d), and (6)(e); (1)(k), (5)(d), and (6)(f); (1)(k), (5)(d), and (6)(g); (1)(k), (5)(d), and (6)(h); (1)(k), (5)(d), and (6)(i); (1)(k), (5)(d), and (6)(j); (1)(k), (5)(d), and (6)(k); (1)(k), (5)(d), and (6)(l); (1)(k), (5)(e), and (6)(a); (1)(k), (5)(e), and (6)(b); (1)(k), (5)(e), and (6)(c); (1)(k), (5)(e), and (6)(d); (1)(k), (5)(e), and (6)(e); (1)(k), (5)(e), and (6)(f); (1)(k), (5)(e), and (6)(g); (1)(k), (5)(e), and (6)(h); (1)(k), (5)(e), and (6)(i); (1)(k), (5)(e), and (6)(j); (1)(k), (5)(e), and (6)(k); (1)(k), (5)(e), and (6)(l); (1)(k), (5)(f), and (6)(a); (1)(k), (5)(f), and (6)(b); (1)(k), (5)(f), and (6)(c); (1)(k), (5)(f), and (6)(d); (1)(k), (5)(f), and (6)(e); (1)(k), (5)(f), and (6)(f); (1)(k), (5)(f), and (6)(g); (1)(k), (5)(f), and (6)(h); (1)(k), (5)(f), and (6)(i); (1)(k), (5)(f), and (6)(j); (1)(k), (5)(f), and (6)(k); (1)(k), (5)(f), and (6)(l); (1)(k), (5)(g), and (6)(a); (1)(k), (5)(g), and (6)(b); (1)(k), (5)(g), and (6)(c); (1)(k), (5)(g), and (6)(d); (1)(k), (5)(g), and (6)(e); (1)(k), (5)(g), and (6)(f); (1)(k), (5)(g), and (6)(g); (1)(k), (5)(g), and (6)(h); (1)(k), (5)(g), and (6)(i); (1)(k), (5)(g), and (6)(j); (1)(k), (5)(g), and (6)(k); (1)(k), (5)(g), and (6)(l); (1)(k), (5)(h), and (6)(a); (1)(k), (5)(h), and (6)(b); (1)(k), (5)(h), and (6)(c); (1)(k), (5)(h), and (6)(d); (1)(k), (5)(h), and (6)(e); (1)(k), (5)(h), and (6)(f); (1)(k), (5)(h), and (6)(g); (1)(k), (5)(h), and (6)(h); (1)(k), (5)(h), and (6)(i); (1)(k), (5)(h), and (6)(j); (1)(k), (5)(h), and (6)(k); (1)(k), (5)(h), and (6)(l); (1)(k), (5)(i), and (6)(a); (1)(k), (5)(i), and (6)(b); (1)(k), (5)(i), and (6)(c); (1)(k), (5)(i), and (6)(d); (1)(k), (5)(i), and (6)(e); (1)(k), (5)(i), and (6)(f); (1)(k), (5)(i), and (6)(g); (1)(k), (5)(i), and (6)(h); (1)(k), (5)(i), and (6)(i); (1)(k), (5)(i), and (6)(j); (1)(k), (5)(i), and (6)(k); (1)(k), (5)(i), and (6)(l); (1)(k), (5)(j), and (6)(a); (1)(k), (5)(j), and (6)(b); (1)(k), (5)(j), and (6)(c); (1)(k), (5)(j), and (6)(d); (1)(k), (5)(j), and (6)(e); (1)(k), (5)(j), and (6)(f); (1)(k), (5)(j), and (6)(g); (1)(k), (5)(j), and (6)(h); (1)(k), (5)(j), and (6)(i); (1)(k), (5)(j), and (6)(j); (1)(k), (5)(j), and (6)(k); (1)(k), (5)(j), and (6)(l); (1)(l), (5)(a), and (6)(a); (1)(l), (5)(a), and (6)(b); (1)(l), (5)(a), and (6)(c); (1)(l), (5)(a), and (6)(d); (1)(l), (5)(a), and (6)(e); (1)(l), (5)(a), and (6)(f); (1)(l), (5)(a), and (6)(g); (1)(l), (5)(a), and (6)(h); (1)(l), (5)(a), and (6)(i); (1)(l), (5)(a), and (6)(j); (1)(l), (5)(a), and (6)(k); (1)(l), (5)(a), and (6)(l); (1)(l), (5)(b), and (6)(a); (1)(l), (5)(b), and (6)(b); (1)(l), (5)(b), and (6)(c); (1)(l), (5)(b), and (6)(d); (1)(l), (5)(b), and (6)(e); (1)(l), (5)(b), and (6)(f); (1)(l), (5)(b), and (6)(g); (1)(l), (5)(b), and (6)(h); (1)(l), (5)(b), and (6)(i); (1)(l), (5)(b), and (6)(j); (1)(l), (5)(b), and (6)(k); (1)(l), (5)(b), and (6)(l); (1)(l), (5)(c), and (6)(a); (1)(l), (5)(c), and (6)(b); (1)(l), (5)(c), and (6)(c); (1)(l), (5)(c), and (6)(d); (1)(l), (5)(c), and (6)(e); (1)(l), (5)(c), and (6)(f); (1)(l), (5)(c), and (6)(g); (1)(l), (5)(c), and (6)(h); (1)(l), (5)(c), and (6)(i); (1)(l), (5)(c), and (6)(j); (1)(l), (5)(c), and (6)(k); (1)(l), (5)(c), and (6)(l); (1)(l), (5)(d), and (6)(a); (1)(l), (5)(d), and (6)(b); (1)(l), (5)(d), and (6)(c); (1)(l), (5)(d), and (6)(d); (1)(l), (5)(d), and (6)(e); (1)(l), (5)(d), and (6)(f); (1)(l), (5)(d), and (6)(g); (1)(l), (5)(d), and (6)(h); (1)(l), (5)(d), and (6)(i); (1)(l), (5)(d), and (6)(j); (1)(l), (5)(d), and (6)(k); (1)(l), (5)(d), and (6)(l); (1)(l), (5)(e), and (6)(a); (1)(l), (5)(e), and (6)(b); (1)(l), (5)(e), and (6)(c); (1)(l), (5)(e), and (6)(d); (1)(l), (5)(e), and (6)(e); (1)(l), (5)(e), and (6)(f); (1)(l), (5)(e), and (6)(g); (1)(l), (5)(e), and (6)(h); (1)(l), (5)(e), and (6)(i); (1)(l), (5)(e), and (6)(j); (1)(l), (5)(e), and (6)(k); (1)(l), (5)(e), and (6)(l); (1)(l), (5)(f), and (6)(a); (1)(l), (5)(f), and (6)(b); (1)(l), (5)(f), and (6)(c); (1)(l), (5)(f), and (6)(d); (1)(l), (5)(f), and (6)(e); (1)(l), (5)(f), and (6)(f); (1)(l), (5)(f), and (6)(g); (1)(l), (5)(f), and (6)(h); (1)(l), (5)(f), and (6)(i); (1)(l), (5)(f), and (6)(j); (1)(l), (5)(f), and (6)(k); (1)(l), (5)(f), and (6)(l); (1)(l), (5)(g), and (6)(a); (1)(l), (5)(g), and (6)(b); (1)(l), (5)(g), and (6)(c); (1)(l), (5)(g), and (6)(d); (1)(l), (5)(g), and (6)(e); (1)(l), (5)(g), and (6)(f); (1)(l), (5)(g), and (6)(g); (1)(l), (5)(g), and (6)(h); (1)(l), (5)(g), and (6)(i); (1)(l), (5)(g), and (6)(j); (1)(l), (5)(g), and (6)(k); (1)(l), (5)(g), and (6)(l); (1)(l), (5)(h), and (6)(a); (1)(l), (5)(h), and (6)(b); (1)(l), (5)(h), and (6)(c); (1)(l), (5)(h), and (6)(d); (1)(l), (5)(h), and (6)(e); (1)(l), (5)(h), and (6)(f); (1)(l), (5)(h), and (6)(g); (1)(l), (5)(h), and (6)(h); (1)(l), (5)(h), and (6)(i); (1)(l), (5)(h), and (6)(j); (1)(l), (5)(h), and (6)(k); (1)(l), (5)(h), and (6)(l); (1)(l), (5)(i), and (6)(a); (1)(l), (5)(i), and (6)(b); (1)(l), (5)(i), and (6)(c); (1)(l), (5)(i), and (6)(d); (1)(l), (5)(i), and (6)(e); (1)(l), (5)(i), and (6)(f); (1)(l), (5)(i), and (6)(g); (1)(l), (5)(i), and (6)(h); (1)(l), (5)(i), and (6)(i); (1)(l), (5)(i), and (6)(j); (1)(l), (5)(i), and (6)(k); (1)(l), (5)(i), and (6)(l); (1)(l), (5)(j), and (6)(a); (1)(l), (5)(j), and (6)(b); (1)(l), (5)(j), and (6)(c); (1)(l), (5)(j), and (6)(d); (1)(l), (5)(j), and (6)(e); (1)(l), (5)(j), and (6)(f); (1)(l), (5)(j), and (6)(g); (1)(l), (5)(j), and (6)(h); (1)(l), (5)(j), and (6)(i); (1)(l), (5)(j), and (6)(j); (1)(l), (5)(j), and (6)(k); (1)(l), (5)(j), and (6)(l); (1)(m), (5)(a), and (6)(a); (1)(m), (5)(a), and (6)(b); (1)(m), (5)(a), and (6)(c); (1)(m), (5)(a), and (6)(d); (1)(m), (5)(a), and (6)(e); (1)(m), (5)(a), and (6)(f); (1)(m), (5)(a), and (6)(g); (1)(m), (5)(a), and (6)(h); (1)(m), (5)(a), and (6)(i); (1)(m), (5)(a), and (6)(j); (1)(m), (5)(a), and (6)(k); (1)(m), (5)(a), and (6)(l); (1)(m), (5)(b), and (6)(a); (1)(m), (5)(b), and (6)(b); (1)(m), (5)(b), and (6)(c); (1)(m), (5)(b), and (6)(d); (1)(m), (5)(b), and (6)(e); (1)(m), (5)(b), and (6)(f); (1)(m), (5)(b), and (6)(g); (1)(m), (5)(b), and (6)(h); (1)(m), (5)(b), and (6)(i); (1)(m), (5)(b), and (6)(j); (1)(m), (5)(b), and (6)(k); (1)(m), (5)(b), and (6)(l); (1)(m), (5)(c), and (6)(a); (1)(m), (5)(c), and (6)(b); (1)(m), (5)(c), and (6)(c); (1)(m), (5)(c), and (6)(d); (1)(m), (5)(c), and (6)(e); (1)(m), (5)(c), and (6)(f); (1)(m), (5)(c), and (6)(g); (1)(m), (5)(c), and (6)(h); (1)(m), (5)(c), and (6)(i); (1)(m), (5)(c), and (6)(j); (1)(m), (5)(c), and (6)(k); (1)(m), (5)(c), and (6)(l); (1)(m), (5)(d), and (6)(a); (1)(m), (5)(d), and (6)(b); (1)(m), (5)(d), and (6)(c); (1)(m), (5)(d), and (6)(d); (1)(m), (5)(d), and (6)(e); (1)(m), (5)(d), and (6)(f); (1)(m), (5)(d), and (6)(g); (1)(m), (5)(d), and (6)(h); (1)(m), (5)(d), and (6)(i); (1)(m), (5)(d), and (6)(j); (1)(m), (5)(d), and (6)(k); (1)(m), (5)(d), and (6)(l); (1)(m), (5)(e), and (6)(a); (1)(m), (5)(e), and (6)(b); (1)(m), (5)(e), and (6)(c); (1)(m), (5)(e), and (6)(d); (1)(m), (5)(e), and (6)(e); (1)(m), (5)(e), and (6)(f); (1)(m), (5)(e), and (6)(g); (1)(m), (5)(e), and (6)(h); (1)(m), (5)(e), and (6)(i); (1)(m), (5)(e), and (6)(j); (1)(m), (5)(e), and (6)(k); (1)(m), (5)(e), and (6)(l); (1)(m), (5)(f), and (6)(a); (1)(m), (5)(f), and (6)(b); (1)(m), (5)(f), and (6)(c); (1)(m), (5)(f), and (6)(d); (1)(m), (5)(f), and (6)(e); (1)(m), (5)(f), and (6)(f); (1)(m), (5)(f), and (6)(g); (1)(m), (5)(f), and (6)(h); (1)(m), (5)(f), and (6)(i); (1)(m), (5)(f), and (6)(j); (1)(m), (5)(f), and (6)(k); (1)(m), (5)(f), and (6)(l); (1)(m), (5)(g), and (6)(a); (1)(m), (5)(g), and (6)(b); (1)(m), (5)(g), and (6)(c); (1)(m), (5)(g), and (6)(d); (1)(m), (5)(g), and (6)(e); (1)(m), (5)(g), and (6)(f); (1)(m), (5)(g), and (6)(g); (1)(m), (5)(g), and (6)(h); (1)(m), (5)(g), and (6)(i); (1)(m), (5)(g), and (6)(j); (1)(m), (5)(g), and (6)(k); (1)(m), (5)(g), and (6)(l); (1)(m), (5)(h), and (6)(a); (1)(m), (5)(h), and (6)(b); (1)(m), (5)(h), and (6)(c); (1)(m), (5)(h), and (6)(d); (1)(m), (5)(h), and (6)(e); (1)(m), (5)(h), and (6)(f); (1)(m), (5)(h), and (6)(g); (1)(m), (5)(h), and (6)(h); (1)(m), (5)(h), and (6)(i); (1)(m), (5)(h), and (6)(j); (1)(m), (5)(h), and (6)(k); (1)(m), (5)(h), and (6)(l); (1)(m), (5)(i), and (6)(a); (1)(m), (5)(i), and (6)(b); (1)(m), (5)(i), and (6)(c); (1)(m), (5)(i), and (6)(d); (1)(m), (5)(i), and (6)(e); (1)(m), (5)(i), and (6)(f); (1)(m), (5)(i), and (6)(g); (1)(m), (5)(i), and (6)(h); (1)(m), (5)(i), and (6)(i); (1)(m), (5)(i), and (6)(j); (1)(m), (5)(i), and (6)(k); (1)(m), (5)(i), and (6)(l); (1)(m), (5)(j), and (6)(a); (1)(m), (5)(j), and (6)(b); (1)(m), (5)(j), and (6)(c); (1)(m), (5)(j), and (6)(d); (1)(m), (5)(j), and (6)(e); (1)(m), (5)(j), and (6)(f); (1)(m), (5)(j), and (6)(g); (1)(m), (5)(j), and (6)(h); (1)(m), (5)(j), and (6)(i); (1)(m), (5)(j), and (6)(j); (1)(m), (5)(j), and (6)(k); (1)(m), (5)(j), and (6)(l); (1)(n), (5)(a), and (6)(a); (1)(n), (5)(a), and (6)(b); (1)(n), (5)(a), and (6)(c); (1)(n), (5)(a), and (6)(d); (1)(n), (5)(a), and (6)(e); (1)(n), (5)(a), and (6)(f); (1)(n), (5)(a), and (6)(g); (1)(n), (5)(a), and (6)(h); (1)(n), (5)(a), and (6)(i); (1)(n), (5)(a), and (6)(j); (1)(n), (5)(a), and (6)(k); (1)(n), (5)(a), and (6)(l); (1)(n), (5)(b), and (6)(a); (1)(n), (5)(b), and (6)(b); (1)(n), (5)(b), and (6)(c); (1)(n), (5)(b), and (6)(d); (1)(n), (5)(b), and (6)(e); (1)(n), (5)(b), and (6)(f); (1)(n), (5)(b), and (6)(g); (1)(n), (5)(b), and (6)(h); (1)(n), (5)(b), and (6)(i); (1)(n), (5)(b), and (6)(j); (1)(n), (5)(b), and (6)(k); (1)(n), (5)(b), and (6)(l); (1)(n), (5)(c), and (6)(a); (1)(n), (5)(c), and (6)(b); (1)(n), (5)(c), and (6)(c); (1)(n), (5)(c), and (6)(d); (1)(n), (5)(c), and (6)(e); (1)(n), (5)(c), and (6)(f); (1)(n), (5)(c), and (6)(g); (1)(n), (5)(c), and (6)(h); (1)(n), (5)(c), and (6)(i); (1)(n), (5)(c), and (6)(j); (1)(n), (5)(c), and (6)(k); (1)(n), (5)(c), and (6)(l); (1)(n), (5)(d), and (6)(a); (1)(n), (5)(d), and (6)(b); (1)(n), (5)(d), and (6)(c); (1)(n), (5)(d), and (6)(d); (1)(n), (5)(d), and (6)(e); (1)(n), (5)(d), and (6)(f); (1)(n), (5)(d), and (6)(g); (1)(n), (5)(d), and (6)(h); (1)(n), (5)(d), and (6)(i); (1)(n), (5)(d), and (6)(j); (1)(n), (5)(d), and (6)(k); (1)(n), (5)(d), and (6)(l); (1)(n), (5)(e), and (6)(a); (1)(n), (5)(e), and (6)(b); (1)(n), (5)(e), and (6)(c); (1)(n), (5)(e), and (6)(d); (1)(n), (5)(e), and (6)(e); (1)(n), (5)(e), and (6)(f); (1)(n), (5)(e), and (6)(g); (1)(n), (5)(e), and (6)(h); (1)(n), (5)(e), and (6)(i); (1)(n), (5)(e), and (6)(j); (1)(n), (5)(e), and (6)(k); (1)(n), (5)(e), and (6)(l); (1)(n), (5)(f), and (6)(a); (1)(n), (5)(f), and (6)(b); (1)(n), (5)(f), and (6)(c); (1)(n), (5)(f), and (6)(d); (1)(n), (5)(f), and (6)(e); (1)(n), (5)(f), and (6)(f); (1)(n), (5)(f), and (6)(g); (1)(n), (5)(f), and (6)(h); (1)(n), (5)(f), and (6)(i); (1)(n), (5)(f), and (6)(j); (1)(n), (5)(f), and (6)(k); (1)(n), (5)(f), and (6)(l); (1)(n), (5)(g), and (6)(a); (1)(n), (5)(g), and (6)(b); (1)(n), (5)(g), and (6)(c); (1)(n), (5)(g), and (6)(d); (1)(n), (5)(g), and (6)(e); (1)(n), (5)(g), and (6)(f); (1)(n), (5)(g), and (6)(g); (1)(n), (5)(g), and (6)(h); (1)(n), (5)(g), and (6)(i); (1)(n), (5)(g), and (6)(j); (1)(n), (5)(g), and (6)(k); (1)(n), (5)(g), and (6)(l); (1)(n), (5)(h), and (6)(a); (1)(n), (5)(h), and (6)(b); (1)(n), (5)(h), and (6)(c); (1)(n), (5)(h), and (6)(d); (1)(n), (5)(h), and (6)(e); (1)(n), (5)(h), and (6)(f); (1)(n), (5)(h), and (6)(g); (1)(n), (5)(h), and (6)(h); (1)(n), (5)(h), and (6)(i); (1)(n), (5)(h), and (6)(j); (1)(n), (5)(h), and (6)(k); (1)(n), (5)(h), and (6)(l); (1)(n), (5)(i), and (6)(a); (1)(n), (5)(i), and (6)(b); (1)(n), (5)(i), and (6)(c); (1)(n), (5)(i), and (6)(d); (1)(n), (5)(i), and (6)(e); (1)(n), (5)(i), and (6)(f); (1)(n), (5)(i), and (6)(g); (1)(n), (5)(i), and (6)(h); (1)(n), (5)(i), and (6)(i); (1)(n), (5)(i), and (6)(j); (1)(n), (5)(i), and (6)(k); (1)(n), (5)(i), and (6)(l); (1)(n), (5)(j), and (6)(a); (1)(n), (5)(j), and (6)(b); (1)(n), (5)(j), and (6)(c); (1)(n), (5)(j), and (6)(d); (1)(n), (5)(j), and (6)(e); (1)(n), (5)(j), and (6)(f); (1)(n), (5)(j), and (6)(g); (1)(n), (5)(j), and (6)(h); (1)(n), (5)(j), and (6)(i); (1)(n), (5)(j), and (6)(j); (1)(n), (5)(j), and (6)(k); (1)(n), (5)(j), and (6)(l); (1)(o), (5)(a), and (6)(a); (1)(o), (5)(a), and (6)(b); (1)(o), (5)(a), and (6)(c); (1)(o), (5)(a), and (6)(d); (1)(o), (5)(a), and (6)(e); (1)(o), (5)(a), and (6)(f); (1)(o), (5)(a), and (6)(g); (1)(o), (5)(a), and (6)(h); (1)(o), (5)(a), and (6)(i); (1)(o), (5)(a), and (6)(j); (1)(o), (5)(a), and (6)(k); (1)(o), (5)(a), and (6)(l); (1)(o), (5)(b), and (6)(a); (1)(o), (5)(b), and (6)(b); (1)(o), (5)(b), and (6)(c); (1)(o), (5)(b), and (6)(d); (1)(o), (5)(b), and (6)(e); (1)(o), (5)(b), and (6)(f); (1)(o), (5)(b), and (6)(g); (1)(o), (5)(b), and (6)(h); (1)(o), (5)(b), and (6)(i); (1)(o), (5)(b), and (6)(j); (1)(o), (5)(b), and (6)(k); (1)(o), (5)(b), and (6)(l); (1)(o), (5)(c), and (6)(a); (1)(o), (5)(c), and (6)(b); (1)(o), (5)(c), and (6)(c); (1)(o), (5)(c), and (6)(d); (1)(o), (5)(c), and (6)(e); (1)(o), (5)(c), and (6)(f); (1)(o), (5)(c), and (6)(g); (1)(o), (5)(c), and (6)(h); (1)(o), (5)(c), and (6)(i); (1)(o), (5)(c), and (6)(j); (1)(o), (5)(c), and (6)(k); (1)(o), (5)(c), and (6)(l); (1)(o), (5)(d), and (6)(a); (1)(o), (5)(d), and (6)(b); (1)(o), (5)(d), and (6)(c); (1)(o), (5)(d), and (6)(d); (1)(o), (5)(d), and (6)(e); (1)(o), (5)(d), and (6)(f); (1)(o), (5)(d), and (6)(g); (1)(o), (5)(d), and (6)(h); (1)(o), (5)(d), and (6)(i); (1)(o), (5)(d), and (6)(j); (1)(o), (5)(d), and (6)(k); (1)(o), (5)(d), and (6)(l); (1)(o), (5)(e), and (6)(a); (1)(o), (5)(e), and (6)(b); (1)(o), (5)(e), and (6)(c); (1)(o), (5)(e), and (6)(d); (1)(o), (5)(e), and (6)(e); (1)(o), (5)(e), and (6)(f); (1)(o), (5)(e), and (6)(g); (1)(o), (5)(e), and (6)(h); (1)(o), (5)(e), and (6)(i); (1)(o), (5)(e), and (6)(j); (1)(o), (5)(e), and (6)(k); (1)(o), (5)(e), and (6)(l); (1)(o), (5)(f), and (6)(a); (1)(o), (5)(f), and (6)(b); (1)(o), (5)(f), and (6)(c); (1)(o), (5)(f), and (6)(d); (1)(o), (5)(f), and (6)(e); (1)(o), (5)(f), and (6)(f); (1)(o), (5)(f), and (6)(g); (1)(o), (5)(f), and (6)(h); (1)(o), (5)(f), and (6)(i); (1)(o), (5)(f), and (6)(j); (1)(o), (5)(f), and (6)(k); (1)(o), (5)(f), and (6)(l); (1)(o), (5)(g), and (6)(a); (1)(o), (5)(g), and (6)(b); (1)(o), (5)(g), and (6)(c); (1)(o), (5)(g), and (6)(d); (1)(o), (5)(g), and (6)(e); (1)(o), (5)(g), and (6)(f); (1)(o), (5)(g), and (6)(g); (1)(o), (5)(g), and (6)(h); (1)(o), (5)(g), and (6)(i); (1)(o), (5)(g), and (6)(j); (1)(o), (5)(g), and (6)(k); (1)(o), (5)(g), and (6)(l); (1)(o), (5)(h), and (6)(a); (1)(o), (5)(h), and (6)(b); (1)(o), (5)(h), and (6)(c); (1)(o), (5)(h), and (6)(d); (1)(o), (5)(h), and (6)(e); (1)(o), (5)(h), and (6)(f); (1)(o), (5)(h), and (6)(g); (1)(o), (5)(h), and (6)(h); (1)(o), (5)(h), and (6)(i); (1)(o), (5)(h), and (6)(j); (1)(o), (5)(h), and (6)(k); (1)(o), (5)(h), and (6)(l); (1)(o), (5)(i), and (6)(a); (1)(o), (5)(i), and (6)(b); (1)(o), (5)(i), and (6)(c); (1)(o), (5)(i), and (6)(d); (1)(o), (5)(i), and (6)(e); (1)(o), (5)(i), and (6)(f); (1)(o), (5)(i), and (6)(g); (1)(o), (5)(i), and (6)(h); (1)(o), (5)(i), and (6)(i); (1)(o), (5)(i), and (6)(j); (1)(o), (5)(i), and (6)(k); (1)(o), (5)(i), and (6)(l); (1)(o), (5)(j), and (6)(a); (1)(o), (5)(j), and (6)(b); (1)(o), (5)(j), and (6)(c); (1)(o), (5)(j), and (6)(d); (1)(o), (5)(j), and (6)(e); (1)(o), (5)(j), and (6)(f); (1)(o), (5)(j), and (6)(g); (1)(o), (5)(j), and (6)(h); (1)(o), (5)(j), and (6)(i); (1)(o), (5)(j), and (6)(j); (1)(o), (5)(j), and (6)(k); (1)(o), (5)(j), and (6)(l); (1)(p), (5)(a), and (6)(a); (1)(p), (5)(a), and (6)(b); (1)(p), (5)(a), and (6)(c); (1)(p), (5)(a), and (6)(d); (1)(p), (5)(a), and (6)(e); (1)(p), (5)(a), and (6)(f); (1)(p), (5)(a), and (6)(g); (1)(p), (5)(a), and (6)(h); (1)(p), (5)(a), and (6)(i); (1)(p), (5)(a), and (6)(j); (1)(p), (5)(a), and (6)(k); (1)(p), (5)(a), and (6)(l); (1)(p), (5)(b), and (6)(a); (1)(p), (5)(b), and (6)(b); (1)(p), (5)(b), and (6)(c); (1)(p), (5)(b), and (6)(d); (1)(p), (5)(b), and (6)(e); (1)(p), (5)(b), and (6)(f); (1)(p), (5)(b), and (6)(g); (1)(p), (5)(b), and (6)(h); (1)(p), (5)(b), and (6)(i); (1)(p), (5)(b), and (6)(j); (1)(p), (5)(b), and (6)(k); (1)(p), (5)(b), and (6)(l); (1)(p), (5)(c), and (6)(a); (1)(p), (5)(c), and (6)(b); (1)(p), (5)(c), and (6)(c); (1)(p), (5)(c), and (6)(d); (1)(p), (5)(c), and (6)(e); (1)(p), (5)(c), and (6)(f); (1)(p), (5)(c), and (6)(g); (1)(p), (5)(c), and (6)(h); (1)(p), (5)(c), and (6)(i); (1)(p), (5)(c), and (6)(j); (1)(p), (5)(c), and (6)(k); (1)(p), (5)(c), and (6)(l); (1)(p), (5)(d), and (6)(a); (1)(p), (5)(d), and (6)(b); (1)(p), (5)(d), and (6)(c); (1)(p), (5)(d), and (6)(d); (1)(p), (5)(d), and (6)(e); (1)(p), (5)(d), and (6)(f); (1)(p), (5)(d), and (6)(g); (1)(p), (5)(d), and (6)(h); (1)(p), (5)(d), and (6)(i); (1)(p), (5)(d), and (6)(j); (1)(p), (5)(d), and (6)(k); (1)(p), (5)(d), and (6)(l); (1)(p), (5)(e), and (6)(a); (1)(p), (5)(e), and (6)(b); (1)(p), (5)(e), and (6)(c); (1)(p), (5)(e), and (6)(d); (1)(p), (5)(e), and (6)(e); (1)(p), (5)(e), and (6)(f); (1)(p), (5)(e), and (6)(g); (1)(p), (5)(e), and (6)(h); (1)(p), (5)(e), and (6)(i); (1)(p), (5)(e), and (6)(j); (1)(p), (5)(e), and (6)(k); (1)(p), (5)(e), and (6)(l); (1)(p), (5)(f), and (6)(a); (1)(p), (5)(f), and (6)(b); (1)(p), (5)(f), and (6)(c); (1)(p), (5)(f), and (6)(d); (1)(p), (5)(f), and (6)(e); (1)(p), (5)(f), and (6)(f); (1)(p), (5)(f), and (6)(g); (1)(p), (5)(f), and (6)(h); (1)(p), (5)(f), and (6)(i); (1)(p), (5)(f), and (6)(j); (1)(p), (5)(f), and (6)(k); (1)(p), (5)(f), and (6)(l); (1)(p), (5)(g), and (6)(a); (1)(p), (5)(g), and (6)(b); (1)(p), (5)(g), and (6)(c); (1)(p), (5)(g), and (6)(d); (1)(p), (5)(g), and (6)(e); (1)(p), (5)(g), and (6)(f); (1)(p), (5)(g), and (6)(g); (1)(p), (5)(g), and (6)(h); (1)(p), (5)(g), and (6)(i); (1)(p), (5)(g), and (6)(j); (1)(p), (5)(g), and (6)(k); (1)(p), (5)(g), and (6)(l); (1)(p), (5)(h), and (6)(a); (1)(p), (5)(h), and (6)(b); (1)(p), (5)(h), and (6)(c); (1)(p), (5)(h), and (6)(d); (1)(p), (5)(h), and (6)(e); (1)(p), (5)(h), and (6)(f); (1)(p), (5)(h), and (6)(g); (1)(p), (5)(h), and (6)(h); (1)(p), (5)(h), and (6)(i); (1)(p), (5)(h), and (6)(j); (1)(p), (5)(h), and (6)(k); (1)(p), (5)(h), and (6)(l); (1)(p), (5)(i), and (6)(a); (1)(p), (5)(i), and (6)(b); (1)(p), (5)(i), and (6)(c); (1)(p), (5)(i), and (6)(d); (1)(p), (5)(i), and (6)(e); (1)(p), (5)(i), and (6)(f); (1)(p), (5)(i), and (6)(g); (1)(p), (5)(i), and (6)(h); (1)(p), (5)(i), and (6)(i); (1)(p), (5)(i), and (6)(j); (1)(p), (5)(i), and (6)(k); (1)(p), (5)(i), and (6)(l); (1)(p), (5)(j), and (6)(a); (1)(p), (5)(j), and (6)(b); (1)(p), (5)(j), and (6)(c); (1)(p), (5)(j), and (6)(d); (1)(p), (5)(j), and (6)(e); (1)(p), (5)(j), and (6)(f); (1)(p), (5)(j), and (6)(g); (1)(p), (5)(j), and (6)(h); (1)(p), (5)(j), and (6)(i); (1)(p), (5)(j), and (6)(j); (1)(p), (5)(j), and (6)(k); (1)(p), (5)(j), and (6)(l); (1)(q), (5)(a), and (6)(a); (1)(q), (5)(a), and (6)(b); (1)(q), (5)(a), and (6)(c); (1)(q), (5)(a), and (6)(d); (1)(q), (5)(a), and (6)(e); (1)(q), (5)(a), and (6)(f); (1)(q), (5)(a), and (6)(g); (1)(q), (5)(a), and (6)(h); (1)(q), (5)(a), and (6)(i); (1)(q), (5)(a), and (6)(j); (1)(q), (5)(a), and (6)(k); (1)(q), (5)(a), and (6)(l); (1)(q), (5)(b), and (6)(a); (1)(q), (5)(b), and (6)(b); (1)(q), (5)(b), and (6)(c); (1)(q), (5)(b), and (6)(d); (1)(q), (5)(b), and (6)(e); (1)(q), (5)(b), and (6)(f); (1)(q), (5)(b), and (6)(g); (1)(q), (5)(b), and (6)(h); (1)(q), (5)(b), and (6)(i); (1)(q), (5)(b), and (6)(j); (1)(q), (5)(b), and (6)(k); (1)(q), (5)(b), and (6)(l); (1)(q), (5)(c), and (6)(a); (1)(q), (5)(c), and (6)(b); (1)(q), (5)(c), and (6)(c); (1)(q), (5)(c), and (6)(d); (1)(q), (5)(c), and (6)(e); (1)(q), (5)(c), and (6)(f); (1)(q), (5)(c), and (6)(g); (1)(q), (5)(c), and (6)(h); (1)(q), (5)(c), and (6)(i); (1)(q), (5)(c), and (6)(j); (1)(q), (5)(c), and (6)(k); (1)(q), (5)(c), and (6)(l); (1)(q), (5)(d), and (6)(a); (1)(q), (5)(d), and (6)(b);

(1)(q), (5)(d), and (6)(c); (1)(q), (5)(d), and (6)(d); (1)(q), (5)(d), and (6)(e); (1)(q), (5)(d), and (6)(f); (1)(q), (5)(d), and (6)(g); (1)(q), (5)(d), and (6)(h); (1)(q), (5)(d), and (6)(i); (1)(q), (5)(d), and (6)(j); (1)(q), (5)(d), and (6)(k); (1)(q), (5)(d), and (6)(l); (1)(q), (5)(e), and (6)(a); (1)(q), (5)(e), and (6)(b); (1)(q), (5)(e), and (6)(c); (1)(q), (5)(e), and (6)(d); (1)(q), (5)(e), and (6)(e); (1)(q), (5)(e), and (6)(f); (1)(q), (5)(e), and (6)(g); (1)(q), (5)(e), and (6)(h); (1)(q), (5)(e), and (6)(i); (1)(q), (5)(e), and (6)(j); (1)(q), (5)(e), and (6)(k); (1)(q), (5)(e), and (6)(l); (1)(q), (5)(f), and (6)(a); (1)(q), (5)(f), and (6)(b); (1)(q), (5)(f), and (6)(c); (1)(q), (5)(f), and (6)(d); (1)(q), (5)(f), and (6)(e); (1)(q), (5)(f), and (6)(f); (1)(q), (5)(f), and (6)(g); (1)(q), (5)(f), and (6)(h); (1)(q), (5)(f), and (6)(i); (1)(q), (5)(f), and (6)(j); (1)(q), (5)(f), and (6)(k); (1)(q), (5)(f), and (6)(l); (1)(q), (5)(g), and (6)(a); (1)(q), (5)(g), and (6)(b); (1)(q), (5)(g), and (6)(c); (1)(q), (5)(g), and (6)(d); (1)(q), (5)(g), and (6)(e); (1)(q), (5)(g), and (6)(f); (1)(q), (5)(g), and (6)(g); (1)(q), (5)(g), and (6)(h); (1)(q), (5)(g), and (6)(i); (1)(q), (5)(g), and (6)(j); (1)(q), (5)(g), and (6)(k); (1)(q), (5)(g), and (6)(l); (1)(q), (5)(h), and (6)(a); (1)(q), (5)(h), and (6)(b); (1)(q), (5)(h), and (6)(c); (1)(q), (5)(h), and (6)(d); (1)(q), (5)(h), and (6)(e); (1)(q), (5)(h), and (6)(f); (1)(q), (5)(h), and (6)(g); (1)(q), (5)(h), and (6)(h); (1)(q), (5)(h), and (6)(i); (1)(q), (5)(h), and (6)(j); (1)(q), (5)(h), and (6)(k); (1)(q), (5)(h), and (6)(l); (1)(q), (5)(i), and (6)(a); (1)(q), (5)(i), and (6)(b); (1)(q), (5)(i), and (6)(c); (1)(q), (5)(i), and (6)(d); (1)(q), (5)(i), and (6)(e); (1)(q), (5)(i), and (6)(f); (1)(q), (5)(i), and (6)(g); (1)(q), (5)(i), and (6)(h); (1)(q), (5)(i), and (6)(i); (1)(q), (5)(i), and (6)(j); (1)(q), (5)(i), and (6)(k); (1)(q), (5)(i), and (6)(l); (1)(q), (5)(j), and (6)(a); (1)(q), (5)(j), and (6)(b); (1)(q), (5)(j), and (6)(c); (1)(q), (5)(j), and (6)(d); (1)(q), (5)(j), and (6)(e); (1)(q), (5)(j), and (6)(f); (1)(q), (5)(j), and (6)(g); (1)(q), (5)(j), and (6)(h); (1)(q), (5)(j), and (6)(i); (1)(q), (5)(j), and (6)(j); (1)(q), (5)(j), and (6)(k); (1)(q), (5)(j), and (6)(l); (1)(r), (5)(a), and (6)(a); (1)(r), (5)(a), and (6)(b); (1)(r), (5)(a), and (6)(c); (1)(r), (5)(a), and (6)(d); (1)(r), (5)(a), and (6)(e); (1)(r), (5)(a), and (6)(f); (1)(r), (5)(a), and (6)(g); (1)(r), (5)(a), and (6)(h); (1)(r), (5)(a), and (6)(i); (1)(r), (5)(a), and (6)(j); (1)(r), (5)(a), and (6)(k); (1)(r), (5)(a), and (6)(l); (1)(r), (5)(b), and (6)(a); (1)(r), (5)(b), and (6)(b); (1)(r), (5)(b), and (6)(c); (1)(r), (5)(b), and (6)(d); (1)(r), (5)(b), and (6)(e); (1)(r), (5)(b), and (6)(f); (1)(r), (5)(b), and (6)(g); (1)(r), (5)(b), and (6)(h); (1)(r), (5)(b), and (6)(i); (1)(r), (5)(b), and (6)(j); (1)(r), (5)(b), and (6)(k); (1)(r), (5)(b), and (6)(l); (1)(r), (5)(c), and (6)(a); (1)(r), (5)(c), and (6)(b); (1)(r), (5)(c), and (6)(c); (1)(r), (5)(c), and (6)(d); (1)(r), (5)(c), and (6)(e); (1)(r), (5)(c), and (6)(f); (1)(r), (5)(c), and (6)(g); (1)(r), (5)(c), and (6)(h); (1)(r), (5)(c), and (6)(i); (1)(r), (5)(c), and (6)(j); (1)(r), (5)(c), and (6)(k); (1)(r), (5)(c), and (6)(l); (1)(r), (5)(d), and (6)(a); (1)(r), (5)(d), and (6)(b); (1)(r), (5)(d), and (6)(c); (1)(r), (5)(d), and (6)(d); (1)(r), (5)(d), and (6)(e); (1)(r), (5)(d), and (6)(f); (1)(r), (5)(d), and (6)(g); (1)(r), (5)(d), and (6)(h); (1)(r), (5)(d), and (6)(i); (1)(r), (5)(d), and (6)(j); (1)(r), (5)(d), and (6)(k); (1)(r), (5)(d), and (6)(l); (1)(r), (5)(e), and (6)(a); (1)(r), (5)(e), and (6)(b); (1)(r), (5)(e), and (6)(c); (1)(r), (5)(e), and (6)(d); (1)(r), (5)(e), and (6)(e); (1)(r), (5)(e), and (6)(f); (1)(r), (5)(e), and (6)(g); (1)(r), (5)(e), and (6)(h); (1)(r), (5)(e), and (6)(i); (1)(r), (5)(e), and (6)(j); (1)(r), (5)(e), and (6)(k); (1)(r), (5)(e), and (6)(l); (1)(r), (5)(f), and (6)(a); (1)(r), (5)(f), and (6)(b); (1)(r), (5)(f), and (6)(c); (1)(r), (5)(f), and (6)(d); (1)(r), (5)(f), and (6)(e); (1)(r), (5)(f), and (6)(f); (1)(r), (5)(f), and (6)(g); (1)(r), (5)(f), and (6)(h); (1)(r), (5)(f), and (6)(i); (1)(r), (5)(f), and (6)(j); (1)(r), (5)(f), and (6)(k); (1)(r), (5)(f), and (6)(l); (1)(r), (5)(g), and (6)(a); (1)(r), (5)(g), and (6)(b); (1)(r), (5)(g), and (6)(c); (1)(r), (5)(g), and (6)(d); (1)(r), (5)(g), and (6)(e); (1)(r), (5)(g), and (6)(f); (1)(r), (5)(g), and (6)(g); (1)(r), (5)(g), and (6)(h); (1)(r), (5)(g), and (6)(i); (1)(r), (5)(g), and (6)(j); (1)(r), (5)(g), and (6)(k); (1)(r), (5)(g), and (6)(l); (1)(r), (5)(h), and (6)(a); (1)(r), (5)(h), and (6)(b); (1)(r), (5)(h), and (6)(c); (1)(r), (5)(h), and (6)(d); (1)(r), (5)(h), and (6)(e); (1)(r), (5)(h), and (6)(f); (1)(r), (5)(h), and (6)(g); (1)(r), (5)(h), and (6)(h); (1)(r), (5)(h), and (6)(i); (1)(r), (5)(h), and (6)(j); (1)(r), (5)(h), and (6)(k); (1)(r), (5)(h), and (6)(l); (1)(r), (5)(i), and (6)(a); (1)(r), (5)(i), and (6)(b); (1)(r), (5)(i), and (6)(c); (1)(r), (5)(i), and (6)(d); (1)(r), (5)(i), and (6)(e); (1)(r), (5)(i), and (6)(f); (1)(r), (5)(i), and (6)(g); (1)(r), (5)(i), and (6)(h); (1)(r), (5)(i), and (6)(i); (1)(r), (5)(i), and (6)(j); (1)(r), (5)(i), and (6)(k); (1)(r), (5)(i), and (6)(l); (1)(r), (5)(j), and (6)(a); (1)(r), (5)(j), and (6)(b); (1)(r), (5)(j), and (6)(c); (1)(r), (5)(j), and (6)(d); (1)(r), (5)(j), and (6)(e); (1)(r), (5)(j), and (6)(f); (1)(r), (5)(j), and (6)(g); (1)(r), (5)(j), and (6)(h); (1)(r), (5)(j), and (6)(i); (1)(r), (5)(j), and (6)(j); (1)(r), (5)(j), and (6)(k); (1)(r), (5)(j), and (6)(l); (1)(s), (5)(a), and (6)(a); (1)(s), (5)(a), and (6)(b); (1)(s), (5)(a), and (6)(c); (1)(s), (5)(a), and (6)(d); (1)(s), (5)(a), and (6)(e); (1)(s), (5)(a), and (6)(f); (1)(s), (5)(a), and (6)(g); (1)(s), (5)(a), and (6)(h); (1)(s), (5)(a), and (6)(i); (1)(s), (5)(a), and (6)(j); (1)(s), (5)(a), and (6)(k); (1)(s), (5)(a), and (6)(l); (1)(s), (5)(b), and (6)(a); (1)(s), (5)(b), and (6)(b); (1)(s), (5)(b), and (6)(c); (1)(s), (5)(b), and (6)(d); (1)(s), (5)(b), and (6)(e); (1)(s), (5)(b), and (6)(f); (1)(s), (5)(b), and (6)(g); (1)(s), (5)(b), and (6)(h); (1)(s), (5)(b), and (6)(i); (1)(s), (5)(b), and (6)(j); (1)(s), (5)(b), and (6)(k); (1)(s), (5)(b), and (6)(l); (1)(s), (5)(c), and (6)(a); (1)(s), (5)(c), and (6)(b); (1)(s), (5)(c), and (6)(c); (1)(s), (5)(c), and (6)(d); (1)(s), (5)(c), and (6)(e); (1)(s), (5)(c), and (6)(f); (1)(s), (5)(c), and (6)(g); (1)(s), (5)(c), and (6)(h); (1)(s), (5)(c), and (6)(i); (1)(s), (5)(c), and (6)(j); (1)(s), (5)(c), and (6)(k); (1)(s), (5)(c), and (6)(l); (1)(s), (5)(d), and (6)(a); (1)(s), (5)(d), and (6)(b); (1)(s), (5)(d), and (6)(c); (1)(s), (5)(d), and (6)(d); (1)(s), (5)(d), and (6)(e); (1)(s), (5)(d), and (6)(f); (1)(s), (5)(d), and (6)(g); (1)(s), (5)(d), and (6)(h); (1)(s), (5)(d), and (6)(i); (1)(s), (5)(d), and (6)(j); (1)(s), (5)(d), and (6)(k); (1)(s), (5)(d), and (6)(l); (1)(s), (5)(e), and (6)(a); (1)(s), (5)(e), and (6)(b); (1)(s), (5)(e), and (6)(c); (1)(s), (5)(e), and (6)(d); (1)(s), (5)(e), and (6)(e); (1)(s), (5)(e), and (6)(f); (1)(s), (5)(e), and (6)(g); (1)(s), (5)(e), and (6)(h); (1)(s), (5)(e), and (6)(i); (1)(s), (5)(e), and (6)(j); (1)(s), (5)(e), and (6)(k); (1)(s), (5)(e), and (6)(l); (1)(s), (5)(f), and (6)(a); (1)(s), (5)(f), and (6)(b); (1)(s), (5)(f), and (6)(c); (1)(s), (5)(f), and (6)(d); (1)(s), (5)(f), and (6)(e); (1)(s), (5)(f), and (6)(f); (1)(s), (5)(f), and (6)(g); (1)(s), (5)(f), and (6)(h); (1)(s), (5)(f), and (6)(i); (1)(s), (5)(f), and (6)(j); (1)(s), (5)(f), and (6)(k); (1)(s), (5)(f), and (6)(l); (1)(s), (5)(g), and (6)(a); (1)(s), (5)(g), and (6)(b); (1)(s), (5)(g), and (6)(c); (1)(s), (5)(g), and (6)(d); (1)(s), (5)(g), and (6)(e); (1)(s), (5)(g), and (6)(f); (1)(s), (5)(g), and (6)(g); (1)(s), (5)(g), and (6)(h); (1)(s), (5)(g), and (6)(i); (1)(s), (5)(g), and (6)(j); (1)(s), (5)(g), and (6)(k); (1)(s), (5)(g), and (6)(l); (1)(s), (5)(h), and (6)(a); (1)(s), (5)(h), and (6)(b); (1)(s), (5)(h), and (6)(c); (1)(s), (5)(h), and (6)(d); (1)(s), (5)(h), and (6)(e); (1)(s), (5)(h), and (6)(f); (1)(s), (5)(h), and (6)(g); (1)(s), (5)(h), and (6)(h); (1)(s), (5)(h), and (6)(i); (1)(s), (5)(h), and (6)(j); (1)(s), (5)(h), and (6)(k); (1)(s), (5)(h), and (6)(l); (1)(s), (5)(i), and (6)(a); (1)(s), (5)(i), and (6)(b); (1)(s), (5)(i), and (6)(c); (1)(s), (5)(i), and (6)(d); (1)(s), (5)(i), and (6)(e); (1)(s), (5)(i), and (6)(f); (1)(s), (5)(i), and (6)(g); (1)(s), (5)(i), and (6)(h); (1)(s), (5)(i), and (6)(i); (1)(s), (5)(i), and (6)(j); (1)(s), (5)(i), and (6)(k); (1)(s), (5)(i), and (6)(l); (1)(s), (5)(j), and (6)(a); (1)(s), (5)(j), and (6)(b); (1)(s), (5)(j), and (6)(c); (1)(s), (5)(j), and (6)(d); (1)(s), (5)(j), and (6)(e); (1)(s), (5)(j), and (6)(f); (1)(s), (5)(j), and (6)(g); (1)(s), (5)(j), and (6)(h); (1)(s), (5)(j), and (6)(i); (1)(s), (5)(j), and (6)(j); (1)(s), (5)(j), and (6)(k); (1)(s), (5)(j), and (6)(l); (1)(t), (5)(a), and (6)(a); (1)(t), (5)(a), and (6)(b); (1)(t), (5)(a), and (6)(c); (1)(t), (5)(a), and (6)(d); (1)(t), (5)(a), and (6)(e); (1)(t), (5)(a), and (6)(f); (1)(t), (5)(a), and (6)(g); (1)(t), (5)(a), and (6)(h); (1)(t), (5)(a), and (6)(i); (1)(t), (5)(a), and (6)(j); (1)(t), (5)(a), and (6)(k); (1)(t), (5)(a), and (6)(l); (1)(t), (5)(b), and (6)(a); (1)(t), (5)(b), and (6)(b); (1)(t), (5)(b), and (6)(c); (1)(t), (5)(b), and (6)(d); (1)(t), (5)(b), and (6)(e); (1)(t), (5)(b), and (6)(f); (1)(t), (5)(b), and (6)(g); (1)(t), (5)(b), and (6)(h); (1)(t), (5)(b), and (6)(i); (1)(t), (5)(b), and (6)(j); (1)(t), (5)(b), and (6)(k); (1)(t), (5)(b), and (6)(l); (1)(t), (5)(c), and (6)(a); (1)(t), (5)(c), and (6)(b); (1)(t), (5)(c), and (6)(c); (1)(t), (5)(c), and (6)(d); (1)(t), (5)(c), and (6)(e); (1)(t), (5)(c), and (6)(f); (1)(t), (5)(c), and (6)(g); (1)(t), (5)(c), and (6)(h); (1)(t), (5)(c), and (6)(i); (1)(t), (5)(c), and (6)(j); (1)(t), (5)(c), and (6)(k); (1)(t), (5)(c), and (6)(l); (1)(t), (5)(d), and (6)(a); (1)(t), (5)(d), and (6)(b); (1)(t), (5)(d), and (6)(c); (1)(t), (5)(d), and (6)(d); (1)(t), (5)(d), and (6)(e); (1)(t), (5)(d), and (6)(f); (1)(t), (5)(d), and (6)(g); (1)(t), (5)(d), and (6)(h); (1)(t), (5)(d), and (6)(i); (1)(t), (5)(d), and (6)(j); (1)(t), (5)(d), and (6)(k); (1)(t), (5)(d), and (6)(l); (1)(t), (5)(e), and (6)(a); (1)(t), (5)(e), and (6)(b); (1)(t), (5)(e), and (6)(c); (1)(t), (5)(e), and (6)(d); (1)(t), (5)(e), and (6)(e); (1)(t), (5)(e), and (6)(f); (1)(t), (5)(e), and (6)(g); (1)(t), (5)(e), and (6)(h); (1)(t), (5)(e), and (6)(i); (1)(t), (5)(e), and (6)(j); (1)(t), (5)(e), and (6)(k); (1)(t), (5)(e), and (6)(l); (1)(t), (5)(f), and (6)(a); (1)(t), (5)(f), and (6)(b); (1)(t), (5)(f), and (6)(c); (1)(t), (5)(f), and (6)(d); (1)(t), (5)(f), and (6)(e); (1)(t), (5)(f), and (6)(f); (1)(t), (5)(f), and (6)(g); (1)(t), (5)(f), and (6)(h); (1)(t), (5)(f), and (6)(i); (1)(t), (5)(f), and (6)(j); (1)(t), (5)(f), and (6)(k); (1)(t), (5)(f), and (6)(l); (1)(t), (5)(g), and (6)(a); (1)(t), (5)(g), and (6)(b); (1)(t), (5)(g), and (6)(c); (1)(t), (5)(g), and (6)(d); (1)(t), (5)(g), and (6)(e); (1)(t), (5)(g), and (6)(f); (1)(t), (5)(g), and (6)(g); (1)(t), (5)(g), and (6)(h); (1)(t), (5)(g), and (6)(i); (1)(t), (5)(g), and (6)(j); (1)(t), (5)(g), and (6)(k); (1)(t), (5)(g), and (6)(l); (1)(t), (5)(h), and (6)(a); (1)(t), (5)(h), and (6)(b); (1)(t), (5)(h), and (6)(c); (1)(t), (5)(h), and (6)(d); (1)(t), (5)(h), and (6)(e); (1)(t), (5)(h), and (6)(f); (1)(t), (5)(h), and (6)(g); (1)(t), (5)(h), and (6)(h); (1)(t), (5)(h), and (6)(i); (1)(t), (5)(h), and (6)(j); (1)(t), (5)(h), and (6)(k); (1)(t), (5)(h), and (6)(l); (1)(t), (5)(i), and (6)(a); (1)(t), (5)(i), and (6)(b); (1)(t), (5)(i), and (6)(c); (1)(t), (5)(i), and (6)(d); (1)(t), (5)(i), and (6)(e); (1)(t), (5)(i), and (6)(f); (1)(t), (5)(i), and (6)(g); (1)(t), (5)(i), and (6)(h); (1)(t), (5)(i), and (6)(i); (1)(t), (5)(i), and (6)(j); (1)(t), (5)(i), and (6)(k); (1)(t), (5)(i), and (6)(l); (1)(t), (5)(j), and (6)(a); (1)(t), (5)(j), and (6)(b); (1)(t), (5)(j), and (6)(c); (1)(t), (5)(j), and (6)(d); (1)(t), (5)(j), and (6)(e); (1)(t), (5)(j), and (6)(f); (1)(t), (5)(j), and (6)(g); (1)(t), (5)(j), and (6)(h); (1)(t), (5)(j), and (6)(i); (1)(t), (5)(j), and (6)(j); (1)(t), (5)(j), and (6)(k); (1)(t), (5)(j), and (6)(l); (1)(u), (5)(a), and (6)(a); (1)(u), (5)(a), and (6)(b); (1)(u), (5)(a), and (6)(c); (1)(u), (5)(a), and (6)(d); (1)(u), (5)(a), and (6)(e); (1)(u), (5)(a), and (6)(f); (1)(u), (5)(a), and (6)(g); (1)(u), (5)(a), and (6)(h); (1)(u), (5)(a), and (6)(i); (1)(u), (5)(a), and (6)(j); (1)(u), (5)(a), and (6)(k); (1)(u), (5)(a), and (6)(l); (1)(u), (5)(b), and (6)(a); (1)(u), (5)(b), and (6)(b); (1)(u), (5)(b), and (6)(c); (1)(u), (5)(b), and (6)(d); (1)(u), (5)(b), and (6)(e); (1)(u), (5)(b), and (6)(f); (1)(u), (5)(b), and (6)(g); (1)(u), (5)(b), and (6)(h); (1)(u), (5)(b), and (6)(i); (1)(u), (5)(b), and (6)(j); (1)(u), (5)(b), and (6)(k); (1)(u), (5)(b), and (6)(l); (1)(u), (5)(c), and (6)(a); (1)(u), (5)(c), and (6)(b); (1)(u), (5)(c), and (6)(c); (1)(u), (5)(c), and (6)(d); (1)(u), (5)(c), and (6)(e); (1)(u), (5)(c), and (6)(f); (1)(u), (5)(c), and (6)(g); (1)(u), (5)(c), and (6)(h); (1)(u), (5)(c), and (6)(i); (1)(u), (5)(c), and (6)(j); (1)(u), (5)(c), and (6)(k); (1)(u), (5)(c), and (6)(l); (1)(u), (5)(d), and (6)(a); (1)(u), (5)(d), and (6)(b); (1)(u), (5)(d), and (6)(c); (1)(u), (5)(d), and (6)(d); (1)(u), (5)(d), and (6)(e); (1)(u), (5)(d), and (6)(f); (1)(u), (5)(d), and (6)(g); (1)(u), (5)(d), and (6)(h); (1)(u), (5)(d), and (6)(i); (1)(u), (5)(d), and (6)(j); (1)(u), (5)(d), and (6)(k); (1)(u), (5)(d), and (6)(l); (1)(u), (5)(e), and (6)(a); (1)(u), (5)(e), and (6)(b); (1)(u), (5)(e), and (6)(c); (1)(u), (5)(e), and (6)(d); (1)(u), (5)(e), and (6)(e); (1)(u), (5)(e), and (6)(f); (1)(u), (5)(e), and (6)(g); (1)(u), (5)(e), and (6)(h); (1)(u), (5)(e), and (6)(i); (1)(u), (5)(e), and (6)(j); (1)(u), (5)(e), and (6)(k); (1)(u), (5)(e), and (6)(l); (1)(u), (5)(f), and (6)(a); (1)(u), (5)(f), and (6)(b); (1)(u), (5)(f), and (6)(c); (1)(u), (5)(f), and (6)(d); (1)(u), (5)(f), and (6)(e); (1)(u), (5)(f), and (6)(f); (1)(u), (5)(f), and (6)(g); (1)(u), (5)(f), and (6)(h); (1)(u), (5)(f), and (6)(i); (1)(u), (5)(f), and (6)(j); (1)(u), (5)(f), and (6)(k); (1)(u), (5)(f), and (6)(l); (1)(u), (5)(g), and (6)(a); (1)(u), (5)(g), and (6)(b); (1)(u), (5)(g), and (6)(c); (1)(u), (5)(g), and (6)(d); (1)(u), (5)(g), and (6)(e); (1)(u), (5)(g), and (6)(f); (1)(u), (5)(g), and (6)(g); (1)(u), (5)(g), and (6)(h); (1)(u), (5)(g), and (6)(i); (1)(u), (5)(g), and (6)(j); (1)(u), (5)(g), and (6)(k); (1)(u), (5)(g), and (6)(l); (1)(u), (5)(h), and (6)(a); (1)(u), (5)(h), and (6)(b); (1)(u), (5)(h), and (6)(c); (1)(u), (5)(h), and (6)(d); (1)(u), (5)(h), and (6)(e); (1)(u), (5)(h), and (6)(f); (1)(u), (5)(h), and (6)(g); (1)(u), (5)(h), and (6)(h); (1)(u), (5)(h), and (6)(i); (1)(u), (5)(h), and (6)(j); (1)(u), (5)(h), and (6)(k); (1)(u), (5)(h), and (6)(l); (1)(u), (5)(i), and (6)(a); (1)(u), (5)(i), and (6)(b); (1)(u), (5)(i), and (6)(c); (1)(u), (5)(i), and (6)(d); (1)(u), (5)(i), and (6)(e); (1)(u), (5)(i), and (6)(f); (1)(u), (5)(i), and (6)(g); (1)(u), (5)(i), and (6)(h); (1)(u), (5)(i), and (6)(i); (1)(u), (5)(i), and (6)(j); (1)(u), (5)(i), and (6)(k); (1)(u), (5)(i), and (6)(l); (1)(u), (5)(j), and (6)(a); (1)(u), (5)(j), and (6)(b); (1)(u), (5)(j), and (6)(c); (1)(u), (5)(j), and (6)(d); (1)(u), (5)(j), and (6)(e); (1)(u), (5)(j), and (6)(f); (1)(u), (5)(j), and (6)(g); (1)(u), (5)(j), and (6)(h); (1)(u), (5)(j), and (6)(i); (1)(u), (5)(j), and (6)(j); (1)(u), (5)(j), and (6)(k); (1)(u), (5)(j), and (6)(l); (1)(v), (5)(a), and (6)(a); (1)(v), (5)(a), and (6)(b); (1)(v), (5)(a), and (6)(c); (1)(v), (5)(a), and (6)(d); (1)(v), (5)(a), and (6)(e); (1)(v), (5)(a), and (6)(f); (1)(v), (5)(a), and (6)(g); (1)(v), (5)(a), and (6)(h); (1)(v), (5)(a), and (6)(i); (1)(v), (5)(a), and (6)(j); (1)(v), (5)(a), and (6)(k); (1)(v), (5)(a), and (6)(l); (1)(v), (5)(b), and (6)(a); (1)(v), (5)(b), and (6)(b); (1)(v), (5)(b), and (6)(c); (1)(v), (5)(b), and (6)(d); (1)(v), (5)(b), and (6)(e); (1)(v), (5)(b), and (6)(f); (1)(v), (5)(b), and (6)(g); (1)(v), (5)(b), and (6)(h); (1)(v), (5)(b), and (6)(i); (1)(v), (5)(b), and (6)(j); (1)(v), (5)(b), and (6)(k); (1)(v), (5)(b), and (6)(l); (1)(v), (5)(c), and (6)(a); (1)(v), (5)(c), and (6)(b); (1)(v), (5)(c), and (6)(c); (1)(v), (5)(c), and (6)(d); (1)(v), (5)(c), and (6)(e); (1)(v), (5)(c), and (6)(f); (1)(v), (5)(c), and (6)(g); (1)(v), (5)(c), and (6)(h); (1)(v), (5)(c), and (6)(i); (1)(v), (5)(c), and (6)(j); (1)(v), (5)(c), and (6)(k); (1)(v), (5)(c), and (6)(l); (1)(v), (5)(d), and (6)(a); (1)(v), (5)(d), and (6)(b); (1)(v), (5)(d), and (6)(c); (1)(v), (5)(d), and (6)(d); (1)(v), (5)(d), and (6)(e); (1)(v), (5)(d), and (6)(f); (1)(v), (5)(d), and (6)(g); (1)(v), (5)(d), and (6)(h); (1)(v), (5)(d), and (6)(i); (1)(v), (5)(d), and (6)(j); (1)(v), (5)(d), and (6)(k); (1)(v), (5)(d), and (6)(l); (1)(v), (5)(e), and (6)(a); (1)(v), (5)(e), and (6)(b); (1)(v), (5)(e), and (6)(c); (1)(v), (5)(e), and (6)(d); (1)(v), (5)(e), and (6)(e); (1)(v), (5)(e), and (6)(f); (1)(v), (5)(e), and (6)(g); (1)(v), (5)(e), and (6)(h); (1)(v), (5)(e), and (6)(i); (1)(v), (5)(e), and (6)(j); (1)(v), (5)(e), and (6)(k); (1)(v), (5)(e), and (6)(l); (1)(v), (5)(f), and (6)(a); (1)(v), (5)(f), and (6)(b); (1)(v), (5)(f), and (6)(c); (1)(v), (5)(f), and (6)(d); (1)(v), (5)(f), and (6)(e); (1)(v), (5)(f), and (6)(f); (1)(v), (5)(f), and (6)(g); (1)(v), (5)(f), and (6)(h); (1)(v), (5)(f), and (6)(i); (1)(v), (5)(f), and (6)(j); (1)(v), (5)(f), and (6)(k); (1)(v), (5)(f), and (6)(l); (1)(v), (5)(g), and (6)(a); (1)(v), (5)(g), and (6)(b); (1)(v), (5)(g), and (6)(c); (1)(v), (5)(g), and (6)(d); (1)(v), (5)(g), and (6)(e); (1)(v), (5)(g), and (6)(f); (1)(v), (5)(g), and (6)(g); (1)(v), (5)(g), and (6)(h); (1)(v), (5)(g), and (6)(i); (1)(v), (5)(g), and (6)(j); (1)(v), (5)(g), and (6)(k); (1)(v), (5)(g), and (6)(l); (1)(v), (5)(h), and (6)(a); (1)(v), (5)(h), and (6)(b); (1)(v), (5)(h), and (6)(c); (1)(v), (5)(h), and (6)(d); (1)(v), (5)(h), and (6)(e); (1)(v), (5)(h), and (6)(f); (1)(v), (5)(h), and (6)(g); (1)(v), (5)(h), and (6)(h); (1)(v), (5)(h), and (6)(i); (1)(v), (5)(h), and (6)(j); (1)(v), (5)(h), and (6)(k); (1)(v), (5)(h), and (6)(l); (1)(v), (5)(i), and (6)(a); (1)(v), (5)(i), and (6)(b); (1)(v), (5)(i), and (6)(c); (1)(v), (5)(i), and (6)(d); (1)(v), (5)(i), and (6)(e); (1)(v), (5)(i), and (6)(f); (1)(v), (5)(i), and (6)(g); (1)(v), (5)(i), and (6)(h); (1)(v), (5)(i), and (6)(i); (1)(v), (5)(i), and (6)(j); (1)(v), (5)(i), and (6)(k); (1)(v), (5)(i), and (6)(l); (1)(v), (5)(j), and (6)(a); (1)(v), (5)(j), and (6)(b); (1)(v), (5)(j), and (6)(c); (1)(v), (5)(j), and (6)(d); (1)(v), (5)(j), and (6)(e); (1)(v), (5)(j), and (6)(f); (1)(v), (5)(j), and (6)(g); (1)(v), (5)(j), and (6)(h); (1)(v), (5)(j), and (6)(i); (1)(v), (5)(j), and (6)(j); (1)(v), (5)(j), and (6)(k); (1)(v), (5)(j), and (6)(l); and the like. In addition, any of the foregoing combinations of embodiments (1), (5),and (6) may be combined with any combination of one or more of embodiments (2), (3), (4), and/or (7) through (14).

DEFINITIONS

Except where the context clearly dictates otherwise, the following definitions shall apply herein:

The term "agglomerated drug particle" refers to a particle comprising one or more overlubricated drug particles and a hydrophobic binding layer comprising a hydrophobic binding material, wherein the one or more overlubricated drug particles are suspended in the hydrophobic binding material.

The term "core particle" refers to a drug particle forming the core of the sustained release granules described herein. The core particle may be a single crystal of the drug, a cluster of crystals of the drug, an amorphous solid particle of the drug, or any combination thereof.

The term "disintegrant material" refers to an agent used in pharmaceutical preparation of tablets, which causes the tablets to disintegrate and release their medicinal substances on contact with moisture. In other words, when the sustained release granules described herein are incorporated in a tablet, the disintegrant material prevents the sustained release granules from sticking together when the tablets are exposed to water. A disintegrant material preferably is water insoluble and exhibits high capillary activity and pronounced hydration capacity. Preferably, the term "disintegrant material" does not include materials that form gels. Suitable disintegrant materials are well-known in the art and include an amino acid, starch, corn starch, carmellose, carmellose sodium, carmellose calcium, croscarmellose sodium, crospovidone, low-substituted hydroxypropylcellulose, hydroxypropyl starch, or sodium carboxymethyl starch, preferably crospovidone or carmellose, and more preferably crospovidone.

The term "dissolution percentage" refers to the percentage of the original amount of a drug that has dissolved at a given time point in a dissolution test.

The term "dissolution test" refers to a test conducted to ascertain the release profile of a drug from a pharmaceutical formulation. All dissolution test results specified herein pertain to a dissolution test conducted according to the following procedure:
  i. Apparatus: USP Apparatus 2 (Rotating Paddle)
  ii. Dissolution Medium: 900 ml de-ionized water at 37° C.±0.5° C.
  iii. Paddle Speed: 75 rpm±4%

The term "drug" includes any active agent appropriate for oral administration, as well as any hydrate, solvate, prodrug, or pharmaceutically acceptable salt of the active agent. Suitable active agents include, but are not limited to, amoxicillin, acetaminophen, buproprion, cefaclor, clavulanic acid, diazepam, disopyramide, fexofenadine, hydrochlorothiazide, isosorbide mononitrate, metformin, methylphenidate, nifedipine, orphenadrine, oxprenolol, oxtriphylline, pentoxifylline, propranolol, pseudoephedrine, quinidine, and zolpidem.

The term "external phase" refers to a material in a pharmaceutical formulation in which the sustained release granules described herein are suspended. The external phase may include one or more pharmaceutically acceptable excipients. The external phase may also include one or more drugs.

The term "hydrophobic binding layer" refers to a layer of hydrophobic binding material in which one or more overlubricated drug particles are suspended in the sustained release granules described herein. Without wishing to be bound by any theory, it is believed that the hydrophobic nature of the hydrophobic binding layer contributes to the sustained release character of the sustained release granules. The hydrophobic binding layer also provides a plasticity to the surface of the drug particles, which facilitates the adhesion of the disintegrant particles.

The term "hydrophobic binding material" refers to a hydrophobic material in which the overlubricated drug particles are suspended. Preferably, the hydrophobic binding material is thermally melted, and then it is solidified by cooling down to cover and bind the overlubricated drug particles. The hydrophobic binding material preferably deforms plastically upon compression such that the formulation components can be molded into tablets. The hydrophobic binding material can be fine or course particles, preferably, superfine particles of less than 10 micron. Preferably, the hydrophobic binding material has a melting point of no more than about 70° C. Preferably, the melting point of the hydrophobic binding material is at least 30° C. lower than the melting point of the hydrophobic adherent material and at least 20° C. lower than the melting point of the drug.

In some embodiments, the hydrophobic binding material is a compound of formula (I) or (II):

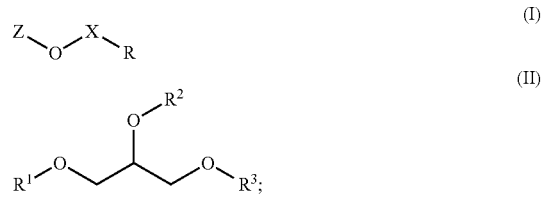

wherein:
R is $C_{11}$-$C_{19}$ alkyl, $C_{11}$-$C_{19}$ alkenyl, or $C_{11}$-$C_{19}$ alkynyl;
X is $CH_2$ or C(O);
Z is H, or $C_1$-$C_3$ alkyl; and
$R^1$, $R^2$, and $R^3$ are each independently H or —X—R, with the proviso that at least one of $R^1$, $R^2$, and $R^3$ is —X—R.

Suitable hydrophobic binding materials also include stearic acid, palmitic acid, stearyl alcohol, palmityl alcohol, glyceryl monostearate, glyceryl mono and distearate, glyceryl tristearate, glyceryl tripalmitate, glyceryl trimyristate, glyceryl tribehenate, and glyceryl palmito-stearic ester.

The term "alkyl" refers to a saturated, monovalent aliphatic hydrocarbon radical including straight chain, branched chain, and cyclic groups having the specified number of carbon atoms.

The term "alkenyl" refers to an unsaturated, monovalent hydrocarbon radical including straight chain, branched chain, and cyclic groups containing one or two carbon-carbon double bonds and having the specified number of carbon atoms.

The term "alkynyl" refers to an unsaturated, monovalent hydrocarbon radical including straight chain, branched chain, and cyclic groups containing one or two carbon-carbon triple bonds and having the specified number of carbon atoms.

The term "hydrophobic adherent layer" refers to a layer of hydrophobic adherent material posited over at least a portion of a core drug particle in the sustained release granules described herein. Without wishing to be bound by any theory, it is believed that the hydrophobic nature of the hydrophobic adherent layer contributes to the sustained release character of the sustained release granules. The hydrophobic adherent layer preferably comprises hydrophobic adherent particles.

The term "hydrophobic adherent material" refers to a hydrophobic material suitable to adhere to the surface of the core particles. Upon adherence, it preferably reduces the friction between the core particles and thereby enhances their flowability. The hydrophobic adherent material also reduces the friction between the core particles and the equipment used in the tableting process, thereby enhancing tablet formation and ejection. Preferably, the hydrophobic adherent material has a melting point at least 30° C. higher than the hydrophobic binding material. This difference in melting point allows the hydrophobic binding material to be melted without melting the hydrophobic adherent material and prevents translational molecular mobility of the hydrophobic adherent material, such that the hydrophobic adherent layer remains on the surface of the drug particle.

In some embodiments, the hydrophobic adherent material is a compound of the formula (III) or (IV):

$$M^+(^-OC(O)R) \qquad (III)$$

$$D^{2+}(^-OC(O)R)_2 \qquad (IV);$$

wherein:

M$^+$ is Li$^+$, Na$^+$, or K$^+$;

D$^{2+}$ is Mg$^{2+}$ or Ca$^{2+}$; and

R is C$_{11}$-C$_{19}$ alkyl, C$_{11}$-C$_{19}$ alkenyl, or C$_{11}$-C$_{19}$ alkynyl.

Suitable hydrophobic adherent materials also include stearic acid salts, such as magnesium stearate, aluminum stearate, calcium stearate, zinc stearate, and sodium stearate. Other suitable hydrophobic adherent materials include palmitic acid salts, such as magnesium palmitate.

The term "hydrophobic adherent particle" refers to a particle comprising hydrophobic adherent material. Preferably, hydrophobic adherent particles have a flake-like shape and a particle size less than 5 µm (projected area diameter). Without wishing to be bound by any theory, it is believed that hydrophobic adherent particles having a flake-like shape have an enhanced propensity to adhere to the surface of a drug particle. A hydrophobic adherent particle shall be understood to have a flake-like shape if its thickness is no more than 50% of the average of its length and width, preferably no more than 20% of the average of its length and width, more preferably no more than about 10% of the average of its length and width, and most preferably no more than 5% of the average of its length and width. Hydrophobic adherent particles have a high capacity to adhere to the surface of drug particles due to their ultra-fine size and flake-like shape, and due to the low level of cohesion between particles as a result of the hydrophobic nature of the hydrophobic adherent material.

The term "hydrophobic drug" refers to a drug having Log P (logarithm n-octanol/water partition coefficient) of at least about 1.

The term "hydrophilic drug" refers to a drug having Log P of less than about 1.

The term "immediate release formulation" refers to a formulation achieving a dissolution percentage greater than or equal to about 50% of a drug within about 2 hours in a dissolution test. Preferably, the dissolution percentage is greater than or equal to about 75% within about 2 hours, greater than 85% within about 2 hours, greater than 90% within about 2 hours, or greater than 95% within about 2 hours.

The term "overlubricated drug particle" refers to a particle comprising a core particle and a hydrophobic adherent layer posited over at least a portion of the core particle. In an overlubricated drug particle, the hydrophobic adherent layer covers substantially the entire surface of those portions of the core particle over which it is posited, such that the surface of those portions of the overlubricated drug particle have substantially the same hydrophobicity as the hydrophobic adherent material. As a result, an overlubricated drug particle generally resists water penetration, leading to delayed drug dissolution. In addition, by rendering the surface of the drug particle hydrophobic, the hydrophobic adherent layer promotes binding between the hydrophobic binding layer and the drug particle. By contrast, in a lubricated drug particle, the hydrophobic adherent layer covers only those regions of the core particle that have the highest surface free energy, leaving "clean surfaces" of the core particle that are not covered by the hydrophobic adherent layer. As a result, a lubricated drug particle generally allows water penetration, leading to rapid drug dissolution.

The term "over mix" (or "over mixed" or "over mixing") refers to the process by which a core drug particle and a hydrophobic adherent material are mixed until a hydrophobic adherent layer covers substantially the entire surface of those portions of the core particle over which it is posited, such that the surface of the drug particle has substantially the same hydrophobicity as the hydrophobic adherent material.

The term "pharmaceutically acceptable excipient" refers to an inert, pharmaceutically acceptable ingredient such as a) a filler or extender such as starches, lactose, sucrose, glucose, mannitol, and silicic acid, b) a binder such as, for example, carboxymethylcellulose, alginates, gelatin, polyvinylpyrrolidinone, sucrose, and *acacia, c)* a diluent such as microcrystalline cellulose, lactose, hydroxypropylcellulose, hydroxypropyl methylcellulose (HPMC), other cellulose derivatives, sucrose, sorbitol, mannitol, dextrins, calcium phosphate, calcium carbonate, sodium alginate, or collagen, d) a disintegrating agent such as agar—agar, calcium carbonate, potato or tapioca starch, alginic acid, certain silicates, and sodium carbonate, e) a solution retarding agent such as paraffin, f) an absorption accelerator such as a quaternary ammonium compound, g) a wetting agent such as, for example, cetyl alcohol and glycerol monostearate, h) an absorbent such as kaolin and bentonite clay, and i) a lubricant such as talc, calcium stearate, magnesium stearate, solid polyethylene glycol, sodium lauryl sulfate, and mixtures thereof.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The "projected area diameter" of a particle is defined as the diameter of a sphere having the same projected area as the particle, as measured using a microscope (e.g., a polarized microscope). The projected area diameter of a sample of particles shall be understood to be the average projected area diameter of the particles.

The term "providing," when used to refer to a material used in a method, means to obtain the material for use in the method, regardless of the means by which the material is obtained.

The terms "substantially isodiametric" and "substantially spherical" mean nearly, but not necessarily precisely spherical. In some embodiments a particle may be understood to have a substantially isodiametric or substantially spherical shape if it has a sphericity of at least 0.7 according to Sphericity-roundness comparison chart of Krumbein and Sloss. See Krumbein, W. C. and Sloss, L. L. (1963). Stratigraphy and Sedimentation, 2nd ed., W. H. Freeman, San Francisco.

The term "suspended" means heterogeneously mixed.

The term "sustained release" refers to the release of a drug over a prolonged period of time.

The term "ratio" refers to the weight-weight ratio of the specified components.

The term "wetting agent" is a compound that lowers the interfacial tension between different phases (e.g., a liquid and a solid). Exemplary wetting agents include, but are not limited to, sodium lauryl sulfate, docusate sodium, polyoxyethylene alkyl ethers, polyoxyl 60 hydrogenated castor oil, poloxamers (poloxamer 188, poloxamer 237, poloxamer 338, and poloxamer 4070), cetylpyridinium chloride, and the wetting agents listed in the Handbook of Pharmaceutical Excipients, Fifth Edition, edited by Raymond C. Rowe, Paul J. Sheskey and Sian C. Owen, Pharmaceutical Press and American Pharmacists Association 2006.

The modified release pharmaceutical formulation of the present invention is useful for the oral administration of a drug for which sustained release is desired. The formulation is particularly useful where it is desired to release one drug immediately and another drug sustainably.

The disintegrating monolithic tablets of the present invention are advantageous for, among other reasons, the reason that they disintegrate in aqueous media (such as the stomach) to small pieces (i.e., the sustained release granules) of less than 1 mm, which facilitates emptying from the stomach to the small intestine. The external phase dissolves or disintegrates immediately (releasing any drug disposed in the external phase immediately), allowing the sustained release granules to disperse in aqueous media. The drug disposed in the sustained release granules is released sustainably.

Preparation of Modified Release Pharmaceutical Formulations

The modified release pharmaceutical formulations of the present invention may be prepared by the following procedure:

Step 1. Core particles comprising the drug are treated with a hydrophobic adherent material to afford overlubricated drug particles. The ratio of the drug to the hydrophobic adherent material may be between about 2:1 and about 50:1, preferably between about 8:1 and about 40:1, more preferably between about 12:1 and about 20:1, and most preferably about 15:1. In some embodiments, the core particles are over mixed with the hydrophobic adherent material, e.g., in a V-mixer (twin-shell mixer). Preferably, in order to ensure suitable mixing, the combined volume of the core particles and the hydrophobic adherent material is no less than about one-third, and no more than about two-thirds of the volume of the V-mixer. The duration of mixing may be between about 10 minutes and about 60 minutes, preferably between about 20 minutes and about 40 minutes, more preferably between about 25 minutes and about 35 minutes, and most preferably about 30 minutes. The rotating speed of the V-mixer may be between about 5 rotations per minute (rpm) and about 50 rpm, preferably between about 10 rpm and about 30 rpm, more preferably between about 15 rpm and about 25 rpm, and most preferably about 20 rpm.

Step 2. The overlubricated drug particles obtained in Step 1 are mixed with a hydrophobic binding material. The ratio of the overlubricated drug particles to the hydrophobic binding material may be between about 2:1 and about 10:1, preferably between about 3:1 and about 8:1, more preferably between about 3.6:1 and about 6:1, and most preferably about 4.5:1. Preferably, the overlubricated drug particles are treated and mixed with the hydrophobic binding material in the same mixing vessel as was used in Step 1. Where Step 1 is conducted in a V-mixer, Step 2 preferably is conducted in the same V-mixer. Preferably, in order to ensure suitable mixing, the combined volume of the overlubricated drug particles and the hydrophobic binding material is no less than about one-third, and no more than about two-thirds of the volume of the V-mixer. The duration of mixing may be between about 10 minutes and about 60 minutes, preferably between about 20 minutes and about 40 minutes, more preferably between about 25 minutes and about 35 minutes, and most preferably about 30 minutes. The rotating speed of the V-mixer may be between about 5 rotations per minute (rpm) and about 50 rpm, preferably between about 10 rpm and about 30 rpm, more preferably between about 15 rpm and about 25 rpm, and most preferably about 20 rpm.

Step 3. The material obtained in Step 2 is granulated to afford agglomerated drug particles. The material may be subjected to hot melt granulation wherein the material is mixed and heated to a temperature suitable to melt the hydrophobic binding material without melting the hydrophobic adherent material. For example, where the hydrophobic adherent material is magnesium stearate and the hydrophobic binding material is stearic acid, the material may be heated to a temperature between about 60° C. and about 70° C., preferably between about 62° C. and about 68° C., more preferably between about 64° C. and about 66° C., and most preferably about 65° C. The material is then granulated, which may be conducted at the same temperature as the mixing.

Step 3 may be conducted in a rapid mixer granulator (RMG), such as a double jacket RMG, fitted with a chopper. Where Step 3 is conducted in an RMG, the material is mixed and granulated with heating at a mixing speed between about 500 rpm and about 2000 rpm, preferably between about 800 rpm and about 1700 rpm, more preferably between about 1100 rpm and about 1500 rpm, and most preferably about 1300 rpm. The duration of mixing may be between about 4 minutes and about 12 minutes, preferably between about 6 minutes and about 10 minutes, more preferably between about 7 minutes and about 9 minutes, and most preferably about 8 minutes. The temperature of mixing should be suitable to melt the hydrophobic binding material without melting the hydrophobic adherent material. For example, where the hydrophobic adherent material is magnesium stearate and the hydrophobic binding material is stearic acid, the material may be heated to a temperature between about 60° C. and about 70° C., preferably between about 62° C. and about 68° C., more preferably between about 64° C. and about 66° C., and most preferably about 65° C.

The chopper is then turned on at a chopper speed of between about 500 rpm and about 2500 rpm, preferably between about 1000 rpm and about 2000 rpm, more preferably between about 1300 rpm and about 1700 rpm, and most preferably about 1500 rpm. Mixing continues during chopping. Preferably, the chopper speed is greater than the mixing speed. The duration of chopping may be between about 1 minute and about 8 minutes, preferably between 2 minutes and about 5 minutes, more preferably between about 2.5 minutes and about 4 minutes, and most preferably about 3 minutes. The temperature during chopping may be the same as or different than the temperature during mixing. The temperature of chopping should be suitable to melt the hydrophobic binding material without melting the hydrophobic adherent material. For example, where the hydrophobic adherent material is magnesium stearate and the hydrophobic binding material is stearic acid, the material may be heated to a temperature between about 60° C. and about 70° C., preferably between about 62° C. and about 68° C., more preferably between about 64° C. and about 66° C., and most preferably about 65° C.

Hot melt granulation may be continued until agglomerated drug particles having an average particle size of about 1-1.5 mm appear, at which time the agglomerate is allowed to cool to room temperature, generally about 25° C. Where hot melt granulation is conducted in an RMG, the mixer and chopper are turned off. The duration of hot melt granulation may depend on the power capacity of the RMG.

Step 4. The agglomerated drug particles obtained from the hot melt granulation of Step 3 may be subject to further granulation, if desired, to afford agglomerated drug particles having a smaller average particle size. For example, the agglomerated drug particles may be sieved using an oscillating granulator. The sieve may have openings of between about 0.5 mm and about 2.0 mm, preferably between 0.7 mm and about 1.5 mm, more preferably between about 0.9 mm and 1.2 mm, and most preferably about 1.0 mm. The size distribution of the resulting agglomerated drug particles may be determined by screening the agglomerated drug particles through sieves having openings of various sizes. The resulting agglomerated drug particles may have a size distribution wherein between about 10% and about 80% of the particles have a size between about 90 µm and about 500 µm, and between about 20% and about 90% of the particles have a size between about 500 µm and about 1000 µm; preferably wherein between about 20% and about 40% of the particles have a size between about 90 µm and about 500 µm, and between about 60% and about 80% of the particles have a size between about 500 µm and about 1000 µm; more preferably wherein between about 25% and about 35% of the particles have a size between about 90 µm and about 500 µm, and between about 65% and about 75% of the particles have a size between about 500 µm and about 1000 µm; and most preferably wherein about 30% of the particles have a size between about 90 µm and about 500 µm, and about 70% of the particles have a size between about 500 µm and about 1000 µm. Other size distributions are also contemplated within the scope of the invention, depending on the desired dissolution characteristics of the formulation.

Step 5. The agglomerated drug particles obtained in Step 3 or 4 are treated with a disintegrant material to afford sustained release granules. The ratio of the agglomerated drug particles to the disintegrant material may be between about 5:1 and about 30:1, preferably between about 8:1 and about 20:1, more preferably between about 10:1 and about 17:1, and most preferably about 12.5:1. The agglomerated drug particles may also be treated with a wetting agent at the same time that they are treated with the disintegrant material. The ratio of the disintegrant material to the wetting agent may be between about 2:1 and about 5:1, preferably between about 2.5:1 and about 4:1, more preferably between about 2.8:1 and about 3.5:1, and most preferably about 3:1. In some embodiments, treating the agglomerated drug particles with a disintegrant material (with or without a wetting agent) may involve mixing the agglomerated drug particles with a disintegrant material (with or without a wetting agent) in a V-mixer. The duration of mixing may be between 5 minutes and about 50 minutes, preferably between about 10 minutes and about 30 minutes, more preferably between about 15 minutes and about 25 minutes, and most preferably about 20 minutes. The rotating speed of the V-mixer is selected to induce tumbling motion of the agglomerated drug particles and the disintegrant material and may be between about 5 rotations per minute (rpm) and about 50 rpm, preferably between about 10 rpm and about 30 rpm, more preferably between about 15 rpm and about 25 rpm, and most preferably about 20 rpm.

Step 6. The sustained release granules obtained in Step 5 may be formulated as disintegrating monolithic tablets in which the sustained release granules are suspended in an external phase comprising a pharmaceutically acceptable excipient. The disintegrating monolithic tablets may be obtained by mixing the sustained release granules with the pharmaceutically acceptable excipient, such as a direct compression diluent, and then compressing the resulting mixture to form the tablets. The pharmaceutically acceptable excipient may make up between about 2% and about 30% by weight of the tablet, preferably between about 5% and about 10% by weight of the tablet, more preferably between about 6% and about 8% by weight of the tablet, and most preferably about 7% by weight of the tablet.

In some embodiments, where the external phase comprises one or more drugs, the disintegrating monolithic tablets may be obtained by mixing the sustained release granules with a pharmaceutically acceptable excipient and one or more drugs, and then compressing the resulting mixture to form the tablets. The pharmaceutically acceptable excipient may make up between about 2% and about 30% by weight of the tablet, preferably between about 5% and about 10% by weight of the tablet, more preferably between about 6% and about 8% by weight of the tablet, and most preferably about 7% by weight of the tablet. The drug(s) mixed with the sustained release granules may be the same as or different than the drug contained in the sustained release granules. The dissolution profiles of the drug may be adjusted by adjusting the amount of the drug in the granules and the external phase.

Preparation of Modified Release
Amoxicillin/Clavulanic Acid Formulation

In a preferred embodiment, where the modified release pharmaceutical formulation is a disintegrating sustained-release amoxicillin/clavulanic acid tablet, the formulation may be prepared by the following procedure:

Step 1. Core particles comprising the amoxicillin trihydrate are treated with magnesium stearate to afford overlubricated amoxicillin trihydrate particles. The ratio of the amoxicillin trihydrate to magnesium stearate may be between about 2:1 and about 50:1, preferably between about 8:1 and about 40:1, more preferably between about 12:1 and about 20:1, and most preferably about 15:1. In some embodiments, the core particles are over mixed with the magnesium stearate, e.g., in a V-mixer (twin-shell mixture). Preferably, in order to ensure suitable mixing, the combined volume of the core particles and the magnesium stearate is no less than about one-third, and no more than about two-thirds of the volume of the V-mixer. The duration of mixing may be between about 10 minutes and about 60 minutes, preferably between about 20 minutes and about 40 minutes, more preferably between about 25 minutes and about 35 minutes, and most preferably about 30 minutes. The rotating speed of the V-mixer may be between about 5 rotations per minute (rpm) and about 50 rpm, preferably between about 10 rpm and about 30 rpm, more preferably between about 15 rpm and about 25 rpm, and most preferably about 20 rpm.

Step 2. The overlubricated amoxicillin trihydrate particles obtained in Step 1 are mixed with stearic acid (e.g., Hystrene 9718). The ratio of the overlubricated amoxicillin trihydrate particles to the stearic acid may be between about 2:1 and about 10:1, preferably between about 3:1 and about 8:1, more preferably between about 3.6:1 and about 6:1, and most preferably about 4.5:1. Preferably, the overlubricated amoxicillin trihydrate particles are treated and mixed with the stearic acid in the same mixing vessel as was used in Step 1. Where Step 1 is conducted in a V-mixer, Step 2 preferably is conducted in the same V-mixer. Preferably, in order to ensure suitable mixing, the combined volume of the overlubricated amoxicillin trihydrate particles and the stearic acid is no less than about one-third, and no more than about two-thirds of the volume of the V-mixer. The duration of mixing may be between about 10 minutes and about 60 minutes, preferably between about 20 minutes and about 40 minutes, more preferably between about 25 minutes and about 35 minutes, and most preferably about 30 minutes. The rotating speed of the V-mixer may be between about 5 rotations per minute (rpm) and about 50 rpm, preferably between about 10 rpm and about 30 rpm, more preferably between about 15 rpm and about 25 rpm, and most preferably about 20 rpm.

Step 3. The material obtained in Step 2 is granulated to afford agglomerated amoxicillin trihydrate particles. The material may be subjected to hot melt granulation wherein the material is mixed and heated to a temperature suitable to melt the stearic acid without melting the magnesium stearate. For example, the material may be heated to a temperature between about 60° C. and about 70° C., preferably between about 62° C. and about 68° C., more preferably between about 64° C. and about 66° C., and most preferably about 65° C. The material is then granulated, which may be conducted at the same temperature as the mixing.

Step 3 may be conducted in a rapid mixer granulator (RMG), such as a double jacket RMG, fitted with a chopper. Where Step 3 is conducted in an RMG, the material is mixed and granulated with heating at a mixing speed between about 500 rpm and about 2000 rpm, preferably between about 800 rpm and about 1700 rpm, more preferably between about 1100 rpm and about 1500 rpm, and most preferably about 1300 rpm. The duration of mixing may be between about 4 minutes and about 12 minutes, preferably between about 6 minutes and about 10 minutes, more preferably between about 7 minutes and about 9 minutes, and most preferably about 8 minutes. The temperature of mixing should be suitable to melt the stearic acid without melting the magnesium stearate. For example, the material may be heated to a temperature between about 60° C. and about 70° C., preferably between about 62° C. and about 68° C., more preferably between about 64° C. and about 66° C., and most preferably about 65° C.

The chopper is then turned on at a chopper speed of between about 500 rpm and about 2500 rpm, preferably between about 1000 rpm and about 2000 rpm, more preferably between about 1300 rpm and about 1700 rpm, and most preferably about 1500 rpm. Mixing continues during chopping. Preferably, the chopper speed is greater than the mixing speed. The duration of chopping may be between about 1 minute and about 8 minutes, preferably between 2 minutes and about 5 minutes, more preferably between about 2.5 minutes and about 4 minutes, and most preferably about 3 minutes. The temperature during chopping may be the same as or different than the temperature during mixing. The temperature of chopping should be suitable to melt the hydrophobic binding material without melting the hydrophobic adherent material. For example, the material may be heated to a temperature between about 60° C. and about 70°

C., preferably between about 62° C. and about 68° C., more preferably between about 64° C. and about 66° C., and most preferably about 65° C.

Hot melt granulation may be continued until agglomerated drug particles having an average particle size of about 1-1.5 mm appear, at which time the agglomerate is allowed to cool to room temperature, generally about 25° C. Where hot melt granulation is conducted in an RMG, the mixer and chopper are turned off. The duration of hot melt granulation may depend on the power capacity of the RMG.

Step 4. The agglomerated amoxicillin trihydrate particles obtained from the hot melt granulation of Step 3 may be subject to further granulation, if desired, to afford agglomerated amoxicillin trihydrate particles having a smaller average particle size. For example, the agglomerated amoxicillin trihydrate particles may be sieved using an oscillating granulator. The sieve may have openings of between about 0.5 mm and about 2.0 mm, preferably between 0.7 mm and about 1.5 mm, more preferably between about 0.9 mm and 1.2 mm, and most preferably about 1.0 mm. The size distribution of the resulting agglomerated amoxicillin trihydrate particles may be determined by screening the agglomerated amoxicillin trihydrate particles through sieves having openings of various sizes. The resulting agglomerated amoxicillin trihydrate particles may have a size distribution wherein between about 10% and about 80% of the particles have a size between about 90 µm and about 500 µm, and between about 20% and about 90% of the particles have a size between about 500 µm and about 1000 µm; preferably wherein between about 20% and about 40% of the particles have a size between about 90 µm and about 500 µm, and between about 60% and about 80% of the particles have a size between about 500 µm and about 1000 µm; more preferably wherein between about 25% and about 35% of the particles have a size between about 90 µm and about 500 µm, and between about 65% and about 75% of the particles have a size between about 500 µm and about 1000 µm; and most preferably wherein about 30% of the particles have a size between about 90 µm and about 500 µm, and about 70% of the particles have a size between about 500 µm and about 1000 µm. Other size distributions are also contemplated within the scope of the invention, depending on the desired dissolution characteristics of the formulation.

Step 5. The agglomerated amoxicillin trihydrate particles obtained in Step 3 or 4 are treated with crosspovidone (e.g., Polyplasdone XL) to afford sustained release amoxicillin trihydrate granules. The ratio of the agglomerated amoxicillin trihydrate particles to the crospovidone may be between about 5:1 and about 30:1, preferably between about 8:1 and about 20:1, more preferably between about 10:1 and about 17:1, and most preferably about 12.5:1. The agglomerated amoxicillin trihydrate particles may also be treated with a wetting agent, such a sodium lauryl sulfate, at the same time that they are treated with the crospovidone. The ratio of the crosspovidone to the wetting agent may be between about 2:1 and about 5:1, preferably between about 2.5:1 and about 4:1, more preferably between about 2.8:1 and about 3.5:1, and most preferably about 3:1. In some embodiments, treating the agglomerated amoxicillin trihydrate particles with crosspovidone (with or without a wetting agent) may involve mixing the agglomerated drug particles with crosspovidone (with or without a wetting agent) in a V-mixer. The duration of mixing may be between 5 minutes and about 50 minutes, preferably between about 10 minutes and about 30 minutes, more preferably between about 15 minutes and about 25 minutes, and most preferably about 20 minutes. The rotating speed of the V-mixer is selected to induce tumbling motion of the agglomerated drug particles and the disintegrant material and may be between about 5 rotations per minute (rpm) and about 50 rpm, preferably between about 10 rpm and about 30 rpm, more preferably between about 15 rpm and about 25 rpm, and most preferably about 20 rpm.

Step 6. The sustained release amoxicillin trihydrate granules obtained in Step 5 may be formulated as disintegrating monolithic tablets in which the sustained release amoxicillin trihydrate granules are suspended in an external phase comprising microcrystalline cellulose (e.g., Avicel). The disintegrating monolithic tablets may be obtained by mixing the sustained release amoxicillin trihydrate granules with the microcrystalline cellulose, and then compressing the resulting mixture to form the tablets. The microcrystalline cellulose may make up between about 2% and about 30% by weight of the tablet, preferably between about 5% and about 10% by weight of the tablet, more preferably between about 6% and about 8% by weight of the tablet, and most preferably about 7% by weight of the tablet.

In some embodiments, where the external phase comprises one or more drugs, the disintegrating monolithic tablets may be obtained by mixing the sustained release amoxicillin trihydrate granules with microcrystalline cellulose and one or more drugs, and then compressing the resulting mixture to form the tablets. The microcrystalline cellulose may make up between about 2% and about 30% by weight of the tablet, preferably between about 5% and about 10% by weight of the tablet, more preferably between about 6% and about 8% by weight of the tablet, and most preferably about 7% by weight of the tablet.

In some embodiments, the sustained release amoxicillin trihydrate granules, which are covered by the required amount of the disintegrant, are mixed with amoxicillin trihydrate and potassium clavulanate/microcrystalline cellulose (1:1). The amount of amoxicillin trihydrate within external phase is about 10 to about 20 wt. %, preferably about 12 to about 18 wt. %, more preferably about 14 to about 16 wt. %, and most preferably about 15 wt. %, of total amoxicillin trihydrate. The total amount of amoxicillin trihydrate in this invented tablet is equivalent to 1,000 mg of amoxicillin and the amount of clavulanate potassium in this invented tablet equivalent to 62.5 mg of clavulanic acid. The final mixture is compressed on rotary press machine using oblong punches (8×22) mm to obtain tablets whose weight ranging from 1600 mg±2% to 1700 mg±2%, hardness 16-20 kg, friability less than 1%. These tablets can be uncoated or coated according to procedures described in the Examples.

EXAMPLES

The following abbreviations are used throughout the Examples:

kg kilograms
g grams
mg milligrams
rpm rotations per minute
° C. degrees Celsius
w/w % percentage by weight
ml milliliters
mm millimeters
gm micrometers (microns)
min minute(s)
CV % coefficient of variation
NMT no more than
h hour(s)

Example 1

Manufacture of Agglomerated Amoxicillin Particles

Agglomerated amoxicillin particles having the following quantitative composition were prepared:

| Component | w/w % |
|---|---|
| Amoxicillin trihydrate | 76.3 |
| Magnesium stearate | 5.1 |
| Stearic acid | 18.6 |
| Total | 100 |

The agglomerated amoxicillin particles having the foregoing quantitative composition were prepared according to the following procedure:

Step 1: Amoxicillin trihydrate (Purimox® Compacted Grade P, DSM Sinochem Pharmaceuticals) (2295.76 g) and magnesium stearate (Palmstar Magnesium Stearate, Peter Greven Asia Sdn Bhd) (153.18 g) were combined in a V-mixer (twin-shell mixer) (V/Y Blender, Jaguar, Mumbai, India) and mixed at 20 rpm for 30 minutes at 25° C.

The particle size distribution of the amoxicillin trihydrate was as follows:

| Particle size (μm) | Frequency % |
|---|---|
| 45-63 | 0.2 |
| 63-90 | 0.4 |
| 90-125 | 1.2 |
| 125-180 | 4.3 |
| 180-250 | 13.6 |
| 250-355 | 34.1 |
| 355-500 | 26.8 |
| 500-600 | 19.5 |
| Total | 100.0 |

The particle size distribution of the magnesium stearate was as follows:

| Particle size (μm) | Frequency % | Cumulative % |
|---|---|---|
| 2-1 | 30.0 | 30.0 |
| 3-2 | 25.2 | 55.2 |
| 4-3 | 14.7 | 69.9 |
| 5-4 | 10.1 | 80.0 |
| 6-5 | 5.4 | 85.4 |
| 7-6 | 4.2 | 89.7 |
| 8-7 | 3.3 | 93.0 |
| 9-8 | 1.2 | 94.2 |
| 10-9 | 1.3 | 95.4 |
| 11-10 | 1.2 | 96.6 |
| 12-11 | 0.8 | 97.5 |
| 13-12 | 0.5 | 98.0 |
| 14-13 | 0.4 | 98.4 |
| 15-14 | 0.5 | 98.9 |
| 16-15 | 0.6 | 99.5 |
| 17-16 | 0.1 | 99.6 |
| 18-17 | 0.4 | 100.0 |
| Total | 100.0 | |

Step 2: Stearic acid (Kortacid PHO5C, Pacific Oleochemicals Sdn Bhd) (560.00 g) was added to the V-mixer, and mixing was continued for 30 additional minutes at 25° C.

The particle size distribution of the stearic acid was as follows:

| Particle size (μm) | Frequency % | Cumulative % |
|---|---|---|
| 2-1 | 19.5 | 19.5 |
| 3-2 | 31.1 | 50.6 |
| 4-3 | 20.3 | 71.0 |
| 5-4 | 12.9 | 83.8 |
| 6-5 | 8.0 | 91.8 |
| 7-6 | 4.1 | 95.9 |
| 8-7 | 1.3 | 97.2 |
| 9-8 | 1.8 | 99.0 |
| 10-9 | 1.0 | 100.0 |
| Total | 100.0 | |

Step 3: The resulting mixture was discharged from the V-mixer into a 10 liter double-jacket rapid mixer granulator (High Speed Mixer Granulator, 10 L Standard & GMP, Jaguar, Mumbai, India) and was mixed according to the following program:

| Mixing step | Mixer | Chopper | Temperature (° C.) | Time (minutes) |
|---|---|---|---|---|
| First mixing | on | off | 65 | 8 |
| Second mixing | on | on | 65 | 3 |

Step 4: The resulting material was allowed to cool to 25° C. and then was sieved on a 1 mm sieve using an oscillating granulator (Jaguar, Mumbai, India) to remove any particles having a diameter in excess of 1 mm. The size distribution of the resulting particles was determined by screening the agglomerated amoxicillin particles using 90 μm, 500 μm, and 1000 μm screens, sequentially. The following size distribution was determined:

| Particle Size (μm) | Percent (%) |
|---|---|
| smaller than 90 | 1 |
| 90-500 | 36 |
| 500-1000 | 60 |
| Larger than 1000 | 3 |

Example 2

Manufacture of Disintegrating Sustained-Release Amoxicillin/Clavulanic Acid Tablets (without Sodium Lauryl Sulfate)

Disintegrating sustained-release amoxicillin/clavulanic acid tablets having the following quantitative composition, which corresponds to a 1000:62.5 ratio of amoxicillin: clavulanic acid, were prepared:

| Component | Mass (mg/tablet) |
|---|---|
| Agglomerated amoxicillin particles | 1278.8 |
| Sodium lauryl sulfate | 00.00 |
| Crospovidone | 100.00 |

| Component | Mass (mg/tablet) |
| --- | --- |
| Amoxicillin trihydrate | 172.20 |
| Potassium clavulanate:Microcrystalline cellulose (1:1) | 149.00 |
| Total weight of tablet | 1700.00 |

The disintegrating sustained-release amoxicillin/clavulanic acid tablets having the foregoing quantitative composition were prepared according to the following procedure:

Step 1: Crospovidone (Polyplasdone XL 10, Ashland, Inc.) (176.47 g) and agglomerated amoxicillin particles (2256.71 g), prepared as described in Example 1, were combined in a V-mixer (twin-shell mixer) (V/Y Blender, Jaguar, Mumbai, India) and mixed at 20 rpm for 20 minutes at 25° C.

The particle size distribution of the crospovidone was as follows:

| Particle size (μm) | Frequency % |
| --- | --- |
| 5-0 | 23.8 |
| 10-5 | 36.6 |
| 15-10 | 15.1 |
| 20-15 | 8.7 |
| 25-20 | 9.3 |
| 30-25 | 4.1 |
| 35-30 | 1.7 |
| 40-35 | 0.6 |
| Total | 100.0 |

Step 2: Amoxicillin trihydrate (303.88 g) and potassium clavulanate/microcrystalline cellulose 1:1 (Sandoz) (262.94 g) were combined in another V-mixer (V/Y Blender, Jaguar, Mumbai, India) and mixed at 20 rpm for 20 minutes at 25° C. to afford an immediate release external phase.

The particle size distribution of the potassium clavulanate/microcrystalline cellulose 1:1 was as follows:

| Particle size (μm) | Frequency % |
| --- | --- |
| 10-0 | 59.7 |
| 20-10 | 23.3 |
| 30-20 | 10.2 |
| 40-30 | 3.9 |
| 50-40 | 1.9 |
| 60-50 | 1.0 |
| Total | 100.0 |

Step 3: The immediate release external phase prepared in Step 2 was transferred to the V-mixer from Step 1, and the resulting mixture was mixed at 20 rpm for 20 minutes at 25° C.

Step 4: The mixture obtained in step 3 was compressed on a rotary press machine (Rotary Tabletting Machine 6 to 71. Model 1, Jaguar, Mumbai, India) using oblong punches to obtain 8 mm×22 mm tablets.

The tablets obtained in Step 4 fulfilled the required properties in quality control testing:

| Test | Property |
| --- | --- |
| Weight | 1701 mg ± 0.5% |
| Hardness | 17.9 ± 1.1 kg |
| Thickness | 7.9 ± 0.1 mm |
| Friability | 0.08% |

Example 3

Manufacture of Disintegrating Sustained-Release Amoxicillin/Clavulanic Acid Tablets (with Sodium Lauryl Sulfate)

Disintegrating sustained-release amoxicillin/clavulanic acid tablets having the following quantitative composition, which corresponds to a 1000:62.5 ratio of amoxicillin:clavulanic acid, were prepared:

| Component | Mass (mg/tablet) |
| --- | --- |
| Sustained-release amoxicillin granules | 1278.8 |
| Sodium lauryl sulfate | 15.00 |
| Crospovidone | 40.50 |
| Amoxicillin trihydrate | 172.20 |
| Potassium clavulanate:Microcrystalline cellulose (1:1) | 149.00 |
| Total weight of tablet | 1655.5 |

The disintegrating sustained-release amoxicillin/clavulanic acid tablets having the foregoing quantitative composition were prepared according to the following procedure:

Step 1: Crospovidone (Polyplasdone XL 10, Ashland, Inc.) (15.85 g), sodium lauryl sulfate (Kolliphor® SLS Fine, BASF) (5.87 g), and agglomerated amoxicillin particles (500.55 g), prepared as described in Example 1, were combined in a V-mixer (twin-shell mixer) (V/Y Blender, Jaguar, Mumbai, India) and mixed at 20 rpm for 20 minutes at 25° C.

Step 2: Amoxicillin trihydrate (67.40 g) and potassium clavulanate/microcrystalline cellulose 1:1 (58.32 g) were combined in another V-mixer (V/Y Blender, Jaguar, Mumbai, India) and mixed at 20 rpm for 20 minutes at 25° C. to afford an immediate release external phase.

Step 3: The immediate release external phase prepared in Step 2 was transferred to the V-mixer from Step 1, and the resulting mixture was mixed at 20 rpm for 20 minutes at 25° C.

Step 4: The mixture obtained in step 3 was compressed on rotary press machine (Rotary Tabletting Machine 6 to 71. Model 1, Jaguar, Mumbai, India) using oblong punches to obtain 8 mm×22 mm tablets.

The tablets obtained in Step 4 displayed the following properties in quality control testing:

| Test | Property |
| --- | --- |
| Weight | 1658 mg ± 0.6% |
| Hardness | 17.1 ± 0.9 kg |
| Thickness | 7.8 ± 0.1 mm |
| Friability | 0.09% |

Example 4

Manufacture of Coated Disintegrating Sustained-Release Amoxicillin/Clavulanic Acid Tablets Preparation of Film Coating Liquid Step 1: Mixture A was prepared as follows. Hypromellose 6 cp (60 g) was gradually added to absolute Alcohol (Ethanol) (900 g) with stirring over 15 minutes at 25° C. Triacetin (18 g) was then gradually added with stirring over 10 minutes at 25° C.

Step 2: Mixture B was prepared as follows. Titanium dioxide (18 g) and de-ionized water (50 g) were mixed for 15 minutes at 25° C. to obtain a homogenous suspension.

Step 3: Mixtures A and B were combined, and the resulting mixture was stirred for 20 minutes at 25° C. to obtain a homogenous suspension, and to afford the film coating liquid.

Coating of Tablets

Disintegrating Sustained-Release Amoxicillin/Clavulanic Acid Tablets (3 kg), prepared as described in Example 2, were coated with about 1 liter of the film coating liquid using a coater (Sugar/Film Coating Auto Coater, GMP model, size 12) set to the following parameters:

| | |
|---|---|
| Outlet temp (° C.) | 37 |
| Inlet temp (° C.) | 55 |
| Flow air (ml/min) | 120 |
| Pump rate (rpm) | 1.5 |
| Drum revolution (rpm) | 9.1 |

The coated tablets had a weight of about 1748 mg±2%.

Example 5

Manufacture of Polished Disintegrating Sustained-Release Amoxicillin/Clavulanic Acid Tablets Preparation of Polishing Solution Polyethylene glycol 6000 (4 g) was dissolved in de-ionized water (6 g).

Absolute ethanol (90 g), and the resulting mixture was stirred to afford the polishing solution.

Polishing of Tablets

Coated Disintegrating Sustained-Release Amoxicillin/Clavulanic Acid Tablets (3.096 kg), prepared as described in Example 4, were polished with the polishing solution using a coater set to the following parameters:

| | |
|---|---|
| Outlet temp (° C.) | 45 |
| Inlet temp (° C.) | 60 |
| Flow air (ml/min) | 110 |
| Pump rate (rpm) | 2 |
| Drum revolution (rpm) | 12 |

The polished tablets had a weight of about 1750 mg±2%.

Example 6

Dissolution Testing of Disintegrating Sustained-Release Amoxicillin/Clavulanic Acid Tablets and Reference Products The release profiles of the disintegrating sustained-release amoxicillin/clavulanic acid tablets described herein (Examples 2, 3, and 4) and several commercially available amoxicillin/clavulanic acid reference products were determined by in vitro dissolution testing. See Center for Drug Evaluation and Research, Clinical Pharmacology and Biopharmaceutics Review, New Drug Application No. 50-785, at *8-9 (Sep. 25, 2002). Dissolution testing was conducted according to the following procedure:

i. Apparatus: USP Apparatus 2 (Rotating Paddle)
  ii. Dissolution Medium: 900 ml de-ionized water at 37° C.±0.5° C.
  iii. Paddle Speed: 75 rpm±4%

Twelve tablets of each of the following amoxicillin/clavulanic acid products were employed in the dissolution testing:

i. Disintegrating Sustained-Release Amoxicillin/Clavulanic Acid Tablets (without sodium lauryl sulfate) (Example 2)
  ii. Disintegrating Sustained-Release Amoxicillin/Clavulanic Acid Tablets (with sodium lauryl sulfate) (Example 3)
  iii. Coated Disintegrating Sustained-Release Amoxicillin/Clavulanic Acid Tablets (Example 4)
  iv. Dr. Reddy's Laboratories generic amoxicillin/clavulanate potassium tablets (1000 mg/62.5 mg)
  v. Sandoz generic amoxicillin/clavulanate potassium tablets (1000 mg/62.5 mg)
  vi. GlaxoSmithKline (Augmentin XR®) amoxicillin/clavulanate potassium tablets (1000 mg/62.5 mg)

A standard solution was prepared by the following procedure: 127.5 mg of amoxicillin trihydrate and 16.5 mg of clavulanate potassium:avicel (1:1) were weighed into a 100 mL volumetric flask. 80 mL of deionized water was added, and the mixture was sonicated at 40° C. for 15 minutes. After the solution cooled to room temperature, deionized water was added to increase the volume of the mixture to 100 mL. A portion of the mixture was filtered through filter paper, and the first 10 mL was discarded. The remaining filtrate was used as the standard solution.

Test solutions were obtained by withdrawing 5 mL from the relevant sample vessels at the sampling time points. The samples were filtered through filter paper prior to analysis.

The quantities of the active ingredients amoxicillin and clavulanic acid released at each point in time were determined by HPLC (HPLC system, Agilent technologies 1260 infinity series) at wave length of UV 220 nm (according to USP 30). The stated values are means values from in each case 12 samples.

The mean release and (CV %) of amoxicillin at 1, 2, 3, and 5 hours and the mean release of clavulanate and (CV %) at 1 hour are shown in the following table:

| | | Example 2 | Example 3 | Example 4 | Dr. Reddy's | Sandoz | GlaxoSmithKline* |
|---|---|---|---|---|---|---|---|
| Amoxicillin | 1 h | 50.82 (1.92) | 50.08 (2.06) | 43.00 (2.52) | 58.74 (5.10) | 65.12 (4.04) | 58.81 |
| | 2 h | 68.19 (1.19) | 69.99 (1.04) | 71.06 (1.48) | 70.25 (7.63) | 71.75 (2.63) | 61.88 |
| | 3 h | 77.85 (0.91) | 80.15 (1.20) | 82.10 (0.86) | 87.29 (7.89) | 80.14 (4.53) | 75.76 |

|  | | Example 2 | Example 3 | Example 4 | Dr. Reddy's | Sandoz | GlaxoSmith Kline* |
|---|---|---|---|---|---|---|---|
| Clavulanic Acid | 5 h | 88.60 (0.69) | 90.26 (1.04) | 92.76 (0.48) | 103.19 (8.25) | 102.06 (1.37) | 96.67 |
|  | 1 h | 95.11 (6.04) | 91.51 (5.75) | 103.01 (0.17) | 100.01 (2.69) | 85.07 (3.20) |  |

*The mean release percentages reported for the GlaxoSmithKline Augmentin XR® product reflect the average of the mean release percentages reported for Batch 99012, Batch 99015, and Batch 99017 in the Clinical Pharmacology & Biopharmaceutics Review for Augmentin XR®. See Center for Drug Evaluation and Research, Clinical Pharmacology and Biopharmaceutics Review, New Drug Application No. 50-785, at *9 (Sep. 25, 2002).

The similarity between the dissolution profiles of the disintegrating sustained-release amoxicillin/clavulanic acid tablets described herein (Examples 2, 3, and 4) and the dissolution profiles of GlaxoSmithKline (Augmentin XR®) amoxicillin/clavulanate potassium tablets, Sandoz generic amoxicillin/clavulanate potassium tablets, and Dr. Reddy's Laboratories generic amoxicillin/clavulanate potassium tablets were evaluated by calculating the similarity factors F2 and F1. The similarity factors F2 and F1 were calculated using the following equations:

$$F1 = \left\{\left[\sum_{t=1}^{n} |R_t - T_t|\right] / \left[\sum_{t=1}^{n} R_t\right]\right\} \times 100$$

$$F2 = 50 \times \log\left\{\left[(1 + 1/n)\sum_{t=1}^{n}(R_t - T_t)^2\right]^{-0.5} \times 100\right\}$$

In the foregoing equations, n is the number of time points, $R_t$ is the mean percent drug dissolved of a reference product at a given time point, and $T_t$ is the mean percent drug dissolved of the test product at a given time point.

The U.S. Food & Drug Administration ("FDA") and the European Medicines Agency ("EMEA") consider two dissolution profiles to be similar if F2 is 50 or more and F1 is 15 or less.

Similarity factors describing the similarity between the dissolution profiles of various test products and the dissolution profile of GlaxoSmithKline's Augmentin XR® are provided in the following table:

| Test Product | F1 | F2 |
|---|---|---|
| Example 2 | 3 | 59 |
| Example 3 | 1 | 57 |
| Example 4 | 1 | 50 |
| Dr. Reddy's | 9 | 55 |
| Sandoz | 9 | 58 |

Similarity factors describing the similarity between the dissolution profiles of various test products and the dissolution profile of Sandoz's generic amoxicillin/clavulanate potassium tablets are provided in the following table:

| Test Product | F1 | F2 |
|---|---|---|
| Example 2 | 11 | 50 |
| Example 3 | 9 | 51 |
| Example 4 | 9 | 46 |

Similarity factors describing the similarity between the dissolution profiles of various test products and the dissolution profile of Dr. Reddy's generic amoxicillin/clavulanate potassium tablets are provided in the following table:

| Test Product | F1 | F2 |
|---|---|---|
| Example 2 | 11 | 51 |
| Example 3 | 9 | 53 |
| Example 4 | 10 | 50 |

As a person of ordinary skill in the art will appreciate, many modifications and variations of the embodiments described herein may be made without departing from the scope of the invention, which is defined by the following claims. The specific embodiments described herein are offered by way of example only.

What is claimed is:

1. A modified release pharmaceutical formulation, comprising one or more sustained release granules, each sustained release granule comprising:
    an agglomerated drug particle comprising:
        a plurality of overlubricated drug particles each comprising:
            a core particle comprising a drug; and
            a hydrophobic adherent layer comprising a hydrophobic adherent material posited over at least a portion of the core particle, wherein the hydrophobic adherent material is a compound of formula (III) or (IV):

$$M^+(^-OC(O)R) \qquad (III)$$

$$D^{2+}(^-OC(O)R)_2 \qquad (IV);$$

wherein:
        $M^+$ is $Li^+$, $Na^+$, or $K^+$;
        $D^{2+}$ is $Mg^{2+}$ or $Ca^{2+}$; and
        R is $C_{11}$-$C_{19}$ alkyl, $C_{11}$-$C_{19}$ alkenyl, or $C_{11}$-$C_{19}$ alkynyl, wherein the hydrophobic adherent material has a melting point of at least about 100° C.; and
    a hydrophobic binding layer consisting of a hydrophobic binding material that has been applied to the plurality of overlubricated drug particles in a molten state, wherein the plurality of overlubricated drug particles are suspended in the hydrophobic binding material, wherein the hydrophobic binding material has a melting point of no more than about 70° C. and is a compound of formula (II):

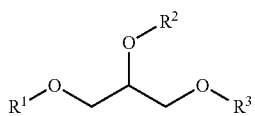 (II)

wherein
R¹, R², and R³ are each independently H or —X—R⁴, with the proviso that at least one of R¹, R², and R³ is —X—R⁴;
R⁴ is $C_{11}$-$C_{19}$ alkenyl or $C_{11}$-$C_{19}$ alkynyl;
X is $CH_2$; and
a disintegrant layer comprising a disintegrant material posited over at least a portion of the hydrophobic binding layer of the agglomerated drug particle.

2. The modified release pharmaceutical formulation of claim 1, wherein the core particle has a substantially isodiametric shape and a diameter of between about 200 μm and about 600 μm.

3. The modified release pharmaceutical formulation of claim 1, wherein the hydrophobic adherent layer comprises a plurality of hydrophobic adherent particles, the hydrophobic adherent particles comprising the hydrophobic adherent material and having a projected area diameter of no more than about 5 μm.

4. The modified release pharmaceutical formulation of claim 1, wherein the hydrophobic adherent material is magnesium stearate.

5. The modified release pharmaceutical formulation of claim 1, wherein the disintegrant layer comprises a wetting agent.

6. The modified release pharmaceutical formulation of claim 1, wherein the drug is amoxicillin or a pharmaceutically acceptable salt thereof.

7. The modified release pharmaceutical formulation of claim 1, further comprising an external phase, wherein the one or more sustained release granules are suspended in the external phase.

8. The modified release pharmaceutical formulation of claim 7, wherein the drug is a first drug, and wherein the external phase comprises a second drug.

9. The modified release pharmaceutical formulation of claim 8, wherein the external phase is an immediate release formulation.

10. The modified release pharmaceutical formulation of claim 7, wherein the drug is amoxicillin or a pharmaceutically acceptable salt thereof, wherein between about 80% and about 90% of the total amoxicillin content is disposed in the sustained release granules, and wherein between about 10% and about 20% of the total amoxicillin content is disposed in the external phase.

11. The modified release pharmaceutical formulation of claim 10, wherein the dissolution percentage of amoxicillin during the first hour of a dissolution test is between about 40% and about 60%.

12. The modified release pharmaceutical formulation of claim 8, wherein the second drug is clavulanic acid or a pharmaceutically acceptable salt thereof.

13. The modified release pharmaceutical formulation of claim 12, wherein the dissolution percentage of clavulanic acid during the first hour of a dissolution test is at least about 85%.

14. A method of preparing sustained release granules for use in a modified release pharmaceutical formulation, the method comprising the steps of:
providing a plurality of agglomerated drug particles each comprising:
a plurality of overlubricated drug particles each comprising:
a core particle comprising a drug; and
a hydrophobic adherent material posited over at least a portion of the core particle, wherein the hydrophobic adherent material is a compound of formula (III) or (IV):

 (III)

 (IV);

wherein:
$M^+$ is $Li^+$, $Na^+$, or $K^+$;
$D^{2+}$ is $Mg^{2+}$ or $Ca^{2+}$; and
R is $C_{11}$-$C_{19}$ alkyl, $C_{11}$-$C_{19}$ alkenyl, or $C_{11}$-$C_{19}$ alkynyl; and
a hydrophobic binding layer consisting of a hydrophobic binding material that has been applied to the plurality of overlubricated drug particles in a molten state, wherein the plurality of overlubricated drug particles are suspended in the hydrophobic binding material, wherein the hydrophobic binding material is a compound of formula (II):

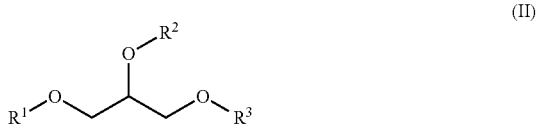 (II)

wherein:
R¹, R², and R³ are each independently H or —X—R⁴, with the proviso that at least one of R¹, R², and R³ is —X—R⁴;
R⁴ is $C_{11}$-$C_{19}$ alkenyl or $C_{11}$-$C_{19}$ alkynyl;
X is $CH_2$; and
treating the agglomerated drug particles with a disintegrant material to afford the sustained release granules.

15. The method of claim 14, wherein the ratio of the agglomerated drug particles to the disintegrant material is between about 10:1 and about 17:1.

16. The method of claim 14, wherein said providing agglomerated drug particles comprises:
providing overlubricated drug particles, each comprising:
a core particle comprising a drug; and
a hydrophobic adherent layer comprising the hydrophobic adherent material posited over at least a portion of the core particle; and
treating the overlubricated drug particles with the hydrophobic binding material to afford the agglomerated drug particles.

17. The method of claim 16, wherein the ratio of the overlubricated drug particles to the hydrophobic binding material is between about 3.6:1 and about 6:1.

18. The method of claim 16, wherein said treating the overlubricated drug particles with a hydrophobic binding material comprises:
mixing the overlubricated drug particles with the hydrophobic binding material;
granulating the resulting mixture at a temperature of between about 60° C. and about 70° C.; and sieving the resulting granules to afford the agglomerated drug particles, wherein between about 10% and about 80% of the agglomerated drug particles have a diameter of between about 90 µm and about 500 µm, and wherein between about 20% and about 90% of the agglomerated drug particles have a diameter of between about 500 µm and about 100 µm.

19. The method of claim 16, wherein said providing overlubricated drug particles comprises treating a plurality of core particles with the hydrophobic adherent material, the core particles comprising the drug, wherein the ratio of the drug to the hydrophobic adherent material is between about 12:1 and about 20:1.

20. The modified release pharmaceutical formulation of claim 1, wherein the ratio of the drug to the hydrophobic adherent material is between about 12:1 and about 20:1.

* * * * *

UNITED STATES PATENT AND TRADEMARK OFFICE
CERTIFICATE OF CORRECTION

PATENT NO. : 11,813,361 B2
APPLICATION NO. : 14/678546
DATED : November 14, 2023
INVENTOR(S) : Mohammad Amin Mohammad It is certified that error appears in the above-identified patent and that said Letters Patent is hereby corrected as shown below:

In the Specification

Column 34, Line 63, delete "gm" and insert in its place --µm--.

Column 35, Line 62, delete "PHO5C" and insert in its place --PH05C--.

In the Claims

Column 44, Claim 17, Line 58, after "16", delete "." and insert in its place --,--.

Column 45, Claim 18, Line 7, delete "100" and insert in its place --1000--.

Signed and Sealed this
Thirteenth Day of February, 2024

Katherine Kelly Vidal
*Director of the United States Patent and Trademark Office*